(12) United States Patent
Tsuchiya et al.

(10) Patent No.: US 7,176,320 B2
(45) Date of Patent: Feb. 13, 2007

(54) BENZIMIDAZOLE DERIVATIVE

(75) Inventors: Naoki Tsuchiya, Hino (JP); Yoshiyuki Matsumoto, Hino (JP); Hiroshi Saitou, Hino (JP); Tsuyoshi Mizuno, Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/777,067

(22) Filed: Feb. 13, 2004

(65) Prior Publication Data

US 2004/0162311 A1  Aug. 19, 2004

Related U.S. Application Data

(63) Continuation of application No. 10/169,866, filed as application No. PCT/JP01/00271 on Jan. 17, 2001, now abandoned.

(30) Foreign Application Priority Data

Jan. 17, 2000 (JP) ............................. 2000-007533
Dec. 25, 2000 (JP) ............................. 2000-392303

(51) Int. Cl.
*C07D 403/12* (2006.01)
*C07D 409/12* (2006.01)
*A61K 31/4184* (2006.01)

(52) U.S. Cl. .................... 548/305.1; 514/387

(58) Field of Classification Search ............. 548/305.1; 514/387

See application file for complete search history.

(56) References Cited

FOREIGN PATENT DOCUMENTS

| | | | |
|---|---|---|---|
| CA | 2336909 A1 | 1/2000 | |
| EP | 1 097 926 A1 | 5/2001 | |
| FR | 2 430 950 A | 2/1980 | |
| JP | 62-212386 A | 9/1987 | |
| JP | 1-265089 A | 10/1989 | |
| WO | WO 99/26932 A1 | 6/1999 | |
| WO | WO 00/03997 A1 | 1/2000 | |
| WO | WO 01/00615 A1 | 1/2001 | |

OTHER PUBLICATIONS

Golub et al., Science, vol. 286, Oct. 15, 1999, pp. 531-537.*

* cited by examiner

*Primary Examiner*—Laura L. Stockton
(74) *Attorney, Agent, or Firm*—Sughrue Mion, PLLC

(57) ABSTRACT

A benzimidazole derivative or its medically acceptable salt, represented by the following formula (1), that is a human chymase activity inhibitor capable of being applied clinically:

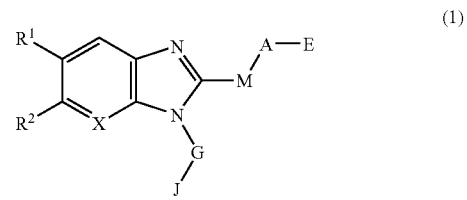

(1)

wherein, $R^1$ and $R^2$ represent a hydrogen atom, an alkyl group or an alkoxy group, etc., A represents an alkylene group or an alkenylene group, E represents —$COOR^3$, —$SO_3R^3$, —$CONHR^3$ or —$SO_2NHR^3$, etc., G represents an alkylene group, M represents a single bond or —$S(O)_m$—, J represents a heterocyclic group, and X represents —CH= or a nitrogen atom.

2 Claims, No Drawings

BENZIMIDAZOLE DERIVATIVE

This is a continuation of application Ser. No. 10/777,067, filed Feb. 13, 2004, which is a continuation of application Ser. No. 10/169,866, filed Jul. 10, 2002, now abandoned which is a 371 of PCT/JP01/00271, filed Jan. 17, 2001.

TECHNICAL FIELD

The present invention relates to a benzimidazole derivative, and more particularly, to a benzimidazole derivative useful as an inhibitor of human chymase activity.

BACKGROUND ART

Chymase is a neutral protease present in mast cell granules, and is intimately involved in various biological reactions participated in by mast cells. For example, chymase has been reported to have various actions, including the promotion of degranulation from mast cells, activation of Interleukin-1β (IL-1β), activation of matrix protease, decomposition of fibronectin and type IV collagen, promotion of the liberation of transforming growth factor-β (TGF-β), activation of substance P and vasoactive intestinal polypeptide (VIP), conversion from angiotensin I (Ang I) to angiotensin II (Ang II), and conversion of endothelin.

On the basis of the above, inhibitors of said chymase activity are considered to be promising as preventive and/or therapeutic agents against respiratory diseases such as bronchial asthma, inflammatory and allergic diseases such as allergic rhinitis, atopic dermatitis and urticaria, cardiovascular diseases such as sclerosing vascular lesions, vasoconstriction, peripheral circulatory disorders, renal insufficiency and cardiac insufficiency, and bone and cartilage metabolic diseases such as rheumatoid arthritis and osteoarthritis.

Although known examples of chymase activity inhibitors of the prior art include a triazine derivative (Japanese Unexamined Patent Publication No. 8-208654), hydantoin derivative (Japanese Unexamined Patent Publication No. 9-31061), imidazolidine derivative (International Publication No. WO96/04248), quinazoline derivative (International Publication No. WO97/11941), heterocyclic amide derivative (International Patent Publication No. WO96/33974), cefam compound (Japanese Unexamined Patent Publication No. 10-087493), phenol derivative (Japanese Unexamined Publication No. 10-087567), heterocyclic amide compound (International Publication No. WO98/18794), acetoamide derivative (International Publication No. WO98/09949), heterocyclic amide compound (Japanese Unexamined Publication No. 10-007661), acid anhydride derivative (Japanese Unexamined Patent Publication No. 11-049739), heterocyclic amide compound (International Publication No. WO99/32459) and acetoamide derivative (International Publication No. WO99/41277), these compounds and the compound of the present invention are completely different structurally.

The chymase inhibitor compounds disclosed thus far have lacked usefulness as a result of having inadequate activity or being structurally unstable. However, the compound of the present invention has extremely high activity and demonstrates superior kinetics in the blood, making it highly useful as a drug.

On the other hand, an example of a technology related to the compound of the present invention is described in the specification of U.S. Pat. No. 5,124,336. A benzimidazole derivative is described in said specification as a compound that has thromboxane receptor antagonistic activity. However, the compound described in said specification is not disclosed as having a heteroaryl group substituted in the benzimidazole skeleton, and there is also no description of human chymase activity of said compound. In addition, although a benzimidazole compound is also described as an antitumor agent in Japanese Unexamined Patent Publication No. 01-265089, there is no mention of human chymase inhibitory activity.

DISCLOSURE OF THE INVENTION

The object of the present invention is to provide a novel compound capable of being a human chymase activity inhibitor that can be applied clinically.

As a result of repeated and earnest research to achieve the above object, the inventors of the present invention found a benzimidazole derivative or its medically acceptable salt, represented by the following formula (1), that has a structure that is completely different from known compounds, thereby leading to completion of the present invention:

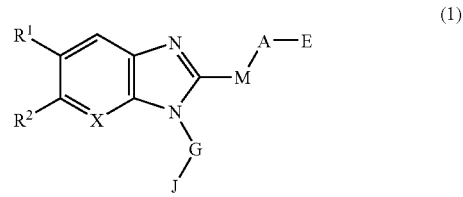

(1)

wherein, $R^1$ and $R^2$ may be the same or different and each independently represents a hydrogen atom, a halogen atom, a trihalomethyl group, a cyano group, a hydroxyl group, an alkyl group having 1–4 carbon atoms, an alkoxy group having 1–4 carbon atoms, or $R^1$ and $R^2$ together represent —O—CH$_2$—O—, —O—CH$_2$CH$_2$—O— or —CH$_2$CH$_2$CH$_2$— (these groups may be substituted by one or more alkyl groups having 1–4 carbon atoms);

A represents a substituted or unsubstituted, linear, cyclic or branched alkylene or alkenylene group having 1–7 carbon atoms which may be interrupted by one or more of —O—, —S—, —SO$_2$— and —NR$^3$— (where $R^3$ represents a hydrogen atom or linear or branched alkyl group having 1–6 carbon atoms); the substituent that can be possessed by these groups is selected from a halogen atom, hydroxyl group, nitro group, cyano group, linear or branched alkyl group having 1–6 carbon atoms, linear or branched alkoxy group having 1–6 carbon atoms (including the case in which two adjacent groups form an acetal bond, namely including the case in which the alkyl portions of geminal two alkoxy groups are connected to form a ring), a linear or branched alkylthio group having 1–6 carbon atoms, a linear or branched alkylsulfonyl group having 1–6 carbon atoms, a linear or branched acyl group having 1–6 carbon atoms, a linear or branched acylamino group having 1–6 carbon atoms, a trihalomethyl group, a trihalomethoxy group, a phenyl group, an oxo group, and a phenoxy group that may be substituted by one or more halogen atoms; and, one or more of these substituents may each independently be bonded to optional positions of the alkylene or alkenylene group, with the proviso that the case in which M is a single bond and a hydroxyl group and a phenyl group are simultaneously bonded as substituents to those carbons of A that are bonded to M is excluded;

E represents a —COOR$^3$, —SO$_3$R$^3$, —CONHR$^3$, —SO$_2$NHR$^3$, tetrazole-5-yl group, a 5-oxo-1,2,4-oxadiazole-3-yl group or a 5-oxo-1,2,4-thiadiazole-3-yl group (where $R^3$ is as defined above);

G represents a substituted or unsubstituted, linear or branched alkylene group having 1–6 carbon atoms which may be interrupted by one or more of —O—, —S—, —SO$_2$— and —NR$^3$— (where, $R^3$ is as defined above. Where these atoms or atomic groups exist, they are not bonded directly to the benzimidazole ring.); and, the substituent that can be possessed by said alkylene group is selected from a halogen atom, a hydroxyl group, a nitro group, a cyano group, a linear or branched alkyl group having 1–6 carbon atoms, a linear or branched alkoxy group having 1–6 carbon atoms (including the case in which two adjacent groups form an acetal bond), a trihalomethyl group, a trihalomethoxy group, a phenyl group, and an oxo group;

M represents a single bond or —S(O)$_m$—, where m is an integer of 0–2;

J represents a substituted or unsubstituted heterocyclic group having 4–10 carbon atoms and containing one or more hetero atoms selected from the group consisting of an oxygen atom, a nitrogen atom and a sulfur atom on its ring, with the proviso that an imidazole ring and an unsubstituted pyridine ring are excluded; the substituent that can be possessed by said aromatic hetetrocyclic group is selected from a halogen atom, a hydroxyl group, a nitro group, a cyano group, a linear or branched alkyl group having 1–6 carbon atoms, a linear or branched alkoxy group having 1–6 carbon atoms (including the case in which two adjacent groups form an acetal bond), a linear or branched alkylthio group having 1–6 carbon atoms, a linear or branched alkylsulfonyl group having 1–6 carbon atoms, a linear or branched acyl group having 1–6 carbon atoms, a linear or branched acylamino group having 1–6 carbon atoms, a substituted or unsubstituted anilide group, a trihalomethyl group, a trihalomethoxy group, a phenyl group, an oxo group, a COOR$^3$ group, and a phenoxy group that may be substituted by one or more halogen atoms; and, one or more of these substitutents may be substituted at optional positions on the ring; and, X represents a methine group (—CH=) or nitrogen atom.

BEST MODE FOR CARRYING OUT THE INVENTION

The substituents in the compound of the present invention represented by the above formula (1) are as indicated below.

$R^1$ and $R^2$ may be the same or different and each independently represents a hydrogen atom, a halogen atom, trihalomethyl group, a cyano group, a hydroxyl group, an alkyl group having 1–4 carbon atoms, an alkoxy group having 1–4 carbon atoms. Alternatively, $R^1$ and $R^2$ together represent —O—CH$_2$—O—, —O—CH$_2$CH$_2$—O— or —CH$_2$CH$_2$CH$_2$—, and in this case, these groups may be substituted by one or more alkyl groups having 1–4 carbon atoms.

Specific examples of the alkyl groups having 1–4 carbon atoms as $R^1$ and $R^2$ include a methyl group, an ethyl group, an n- or i-propyl group and an n-, i-, s- or t-butyl group. A preferable example is a methyl group. Specific examples of alkoxy groups having 1–4 carbon atoms include a methoxy group, an ethoxy group, an n- or i-propoxy group and an n-, i-, s- or t-butoxy group.

Preferable examples of $R^1$ and $R^2$ include a hydrogen atom, a halogen atom, a trihalomethyl group, a cyano group, a hydroxyl group, an alkyl group having 1–4 carbon atoms and an alkoxy group having 1–4 carbon atoms. More preferable examples include a hydrogen atom, a halogen atom, a trihalomethyl group, a cyano group, an alkyl group having 1–4 carbon atoms and an alkoxy group having 1–4 carbon atoms, still more preferable examples include a hydrogen atom, chlorine atom, a fluorine atom, a trifluoromethyl group, methyl group, a methoxy group and an ethoxy group, while particularly preferable examples include a hydrogen atom, a methyl group and a methoxy group.

A represents a substituted or unsubstituted, linear, cyclic or branched alkylene or alkenylene group having 1–7 carbon atoms. Examples of the unsubstituted, linear, cyclic or branched alkylene group having 1–7 carbon atoms include a methylene group, an ethylene group, an n- or i-propylene group, a 2,2-dimethylpropylene group, an n-, i- or t-butylene group, a 1,1-dimethylbutylene group, an n-pentylene group and a cyclohexylene group. More preferable examples include an ethylene group, an n-propylene group, a 2,2-dimethylpropylene group and an n- or t-butylene group. Still more preferable examples include an n-propylene group and a 2,2-dimethylpropylene group. A particularly preferable example is an n-propylene group. Examples of the unsubstituted linear or branched alkenylene group having 1–7 carbon atoms include a vinylene group, a propenylene group, a butenylene group and a pentenylene group.

Although said alkylene group or alkenylene group may be interrupted by one or more of —O—, —S—, —SO$_2$— and —NR$^3$— (where $R^3$ represents a hydrogen atom or linear or branched alkyl group having 1–6 carbon atoms), these atoms or atomic groups are not bonded directly to M. Specific examples include interrupted ethylene groups, n-propylene groups or n- or t-butylene groups. More specific examples include —CH$_2$OCH$_2$—, —CH$_2$OCH$_2$CH$_2$—, —CH$_2$SCH$_2$—, —CH$_2$SCH$_2$CH$_2$—, —CH$_2$SO$_2$CH$_2$—, —CH$_2$SO$_2$CH$_2$CH$_2$—, —CH$_2$NR$^4$CH$_2$— and —CH$_2$NR$^4$CH$_2$CH$_2$—. Preferable examples include —CH$_2$OCH$_2$—, —CH$_2$SCH$_2$— and —CH$_2$SO$_2$CH$_2$—.

The substituent groups that can be possessed by said alkylene group is selected from a halogen atom, a hydroxyl group, a nitro group, a cyano group, a linear or branched alkyl group having 1–6 carbon atoms, a linear or branched alkoxy group having 1–6 carbon atoms (including the case in which two adjacent groups form an acetal bond), a linear or branched alkylthio group having 1–6 carbon atoms, a linear or branched alkylsulfonyl group having 1–6 carbon atoms, linear or branched acyl group having 1–6 carbon atoms, a linear or branched acylamino group having 1–6 carbon atoms, a trihalomethyl group, a trihalomethoxy group, a phenyl group, an oxo group, and a phenoxy group that may be substituted by one or more halogen atoms. One or more of these substituents may each be independently bonded to optional positions of the alkylene group or alkenylene group, with the proviso that the case in which M is a single bond and a hydroxyl group and a phenyl group are simultaneously bonded as substituents to those carbons of A that are bonded to M is excluded.

Examples of the halogen atom include a fluorine atom, a chlorine atom, a bromine atom and an iodine atom. Preferable examples are a fluorine atom and a chlorine atom.

Specific examples of the linear or branched alkyl group having 1–6 carbon atoms include a methyl group, an ethyl group, an n- or i-propyl group and an n-, i-, s- or t-butyl group, while preferable examples are a methyl group and an ethyl group. A more preferable example is a methyl group.

Specific examples of the linear or branched alkoxy group having 1–6 carbon atoms include a methoxy group, an ethoxy group, an n- or i-propoxy group and an n-, i-, s- or t-butoxy group, while preferable examples are a methoxy group and an ethoxy group. A more preferable example is a methoxy group.

Specific examples of the linear or branched alkylthio group having 1–6 carbon atoms include a methylthio group, an ethylthio group, an n- or i-propylthio group, and an n-, i-, s- or t-butylthio group, and preferable examples are a methylthio group and an ethylthio group. A more preferable example is a methylthio group.

Specific examples of the linear or branched alkylsulfonyl group having 1–6 carbon atoms include a methylsulfonyl group, an ethylsulfonyl group, an n- or i-propylsulfonyl group and an n-, i-, s- or t-butylsulfonyl group, and preferable examples are a methylsulfonyl group and an ethylsulfonyl group. A more preferable example is a methylsulfonyl group.

Examples of the linear or branched acyl group having 1–6 carbon atoms include an acetyl group, an ethylcarbonyl group, an n- or i-propylcarbonyl group and an n-, i-, s- or t-butylcarbonyl group, and preferable examples are an acetyl group and an ethylcarbonyl group. A more preferable example is an acetyl group.

Specific examples of the linear or branched acylamino group having 1–6 carbon atoms include an acetylamino group, an ethylcarbonylamino group, an n- or i-propylcarbonylamino group and an n-, i-, s- or t-butylcarbonylamino group, and preferable examples are an acetylamino group and an ethylcarbonylamino group. A more preferable example is an acetylamino group.

Specific examples of the trihalomethyl group are a trifluoromethyl group, a tribromomethyl group and a trichloromethyl group. A preferable example is a trifluoromethyl group.

In particular, A is preferably a substituted or unsubstituted, linear, cyclic or branched alkylene group having 1–7 carbon atoms {although it may be interrupted by one or more of —O—, —S—, —$SO_2$— and —$NR^3$— (where $NR^3$ is as defined above), these atoms or atomic groups not being bonded directly to M}. Preferable examples include —$CH_2CH_2$—, —$CH_2CH_2CH_2$—, —$CH_2C(=O)CH_2$—, —$CH_2OCH_2$—, —$CH_2SCH_2$—, —$CH_2S(=O)CH_2$—, —$CH_2CF_2CH_2$—, —$CH_2SO_2CH_2$—, —$CH_2CH_2CH_2CH_2$—, —$CH_2C(CH_3)_2CH_2$—, —$CH_2SO_2CH_2CH_2$—, —$CH_2C(=O)CH_2CH_2$—, —$CH_2C(=O)(CH_3)_2CH_2$—, and —$CH_2C(=O)C(=O)CH_2$—. More preferable examples are —$CH_2CH_2$—, —$CH_2CH_2CH_2$—, —$CH_2C(=O)CH_2$—, —$CH_2OCH_2$—, $CH_2SCH_2$—, —$CH_2S(=O)CH_2$—, —$CH_2CF_2CH_2$—, —$CH_2SO_2CH_2$— and —$CH_2C(CH_3)_2CH_2$—. Still more preferable examples are —$CH_2CH_2$—, —$CH_2CH_2CH_2$— and —$CH_2C(CH_3)_2CH_2$—. A particularly preferable example is —$CH_2CH_2CH_2$.

E represents a —$COOR^3$, —$SO_3R^3$, —$CONHR^3$, —$SO_2NHR^3$, tetrazole-5-yl, 5-oxo-1,2,4-oxadiazole-3-yl or 5-oxo-1,2,4-thiadiazole-3-yl group (where, $R^3$ represents a hydrogen atom or linear or branched alkyl group having 1–6 carbon atoms).

Examples of $R^3$ include a hydrogen atom, a methyl group, an ethyl group, an n- or i-propyl group and an n-, i-, s- or t-butyl group. Preferable examples are a hydrogen atom, a methyl group and an ethyl group. A particularly preferable example is a hydrogen atom.

In particular, preferable examples of E are —$COOR^3$, —$SO_3R^3$, and tetrazole-5-yl groups. A more preferable example is a —$COOR^3$ group. A particularly preferable example is a —COOH group.

G represents a substituted or unsubstituted, linear or branched alkylene group having 1–6 carbon atoms which may be interrupted by one or more of —O—, —S—, —$SO_2$— and —$NR^3$—. Here, $R^3$ is as defined above. In addition, in the case of containing these hetero atoms or atomic groups, they are not directly bonded to the benzimidazole ring. The substituent that can be possessed by the alkylene group is selected from a halogen atom, a hydroxyl group, a nitro group, a cyano group, a linear or branched alkyl group having 1–6 carbon atoms, a linear or branched alkoxy group having 1–6 carbon atoms (including the case in which two adjacent groups form an acetal bond), a trihalomethyl group, a trihalomethoxy group, a phenyl group and an oxo group. Specific examples of G include —$CH_2$—, —$CH_2CH_2$—, —$CH_2CO$—, —$CH_2CH_2O$—, —$CH_2CONH$—, —CO—, —$SO_2$—, —$CH_2SO_2$—, —$CH_2S$— and —$CH_2CH_2S$—, while preferable examples are —$CH_2$—, —$CH_2CH_2$—, —$CH_2CO$— and —$CH_2CH_2O$—. More preferable examples are —$CH_2$— and —$CH_2CH_2$—, and a particularly preferable example is —$CH_2$—. These groups are bonded on the left hand side to position 1 (N atom) of the benzimidazole ring, while on the right hand side to J.

M represents a single bond or —$S(O)_m$—, where m represents an integer of 0–2. Preferable examples of M are —S— and —$SO_2$—. A particularly preferable example is —S—.

J represents a substituted or unsubstituted heterocyclic group having 4–10 carbon atoms and containing one or more hetero atoms selected from the group consisting of an oxygen atom, a nitrogen atom and a sulfur atom on its ring. However, an imidazole ring and an unsubstituted pyridine ring are excluded. In addition, J is limited to that which can be chemically synthesized.

Specific examples of the unsubstituted heterocyclic groups having 4–10 carbon atoms and containing one or more hetero atoms on its ring selected from the group consisting of an oxygen atom, a nitrogen atom and a sulfur atom include a furyl group, a thienyl group, a thiazolyl group, a pyrimidinyl group, an oxazolyl group, an isooxazolyl group, a benzofuryl group, a benzimidazolyl group, a quinolyl group, an isoquinolyl group, a quinoxalinyl group, a benzoxadiazolyl group, a benzothiaziazolyl group, an indolyl group, a benzothiazolyl group, a benzothienyl group and a benzoisooxazolyl group. A preferable example is a bicyclic heterocyclic ring. More preferable examples are a benzofuryl group, a benzoimidazolyl group, a quinolyl group, an isoquinolyl group, a quinoxalinyl group, a benzoxadiazolyl group, a benzothiazolyl group, an indolyl group, a benzothiazolyl group, a benzothienyl group and a benzoisooxazolyl group, while a particularly preferable example is a benzothienyl group or an indolyl group.

The substituent groups that can be possessed by the aromatic heterocyclic group is selected from a halogen atom, a hydroxyl group, a nitro group, a cyano group, a linear or branched alkyl group having 1–6 carbon atoms, a linear or branched alkoxy group having 1–6 carbon atoms (including the case in which two adjacent groups form an acetal bond), a linear or branched alkylthio group having 1–6 carbon atoms, a linear or branched alkylsulfonyl group having 1–6 carbon atoms, a linear or branched acyl group having 1–6 carbon atoms, a linear or branched acylamino group having 1–6 carbon atoms, a substituted or unsubstituted anilide group, a trihalomethyl group, a trihalomethoxy group, a phenyl group, and a phenoxy group that may be substituted by one or more halogen atoms. One or more of these substituents groups may each independently be bonded to optional positions of the ring.

Examples of the halogen atom are a fluorine atom, a chlorine atom, a bromine atom and an iodine atom. Preferable examples are a fluorine atom and a chlorine atom.

Specific examples of the linear or branched alkyl groups having 1–6 carbon atoms include a methyl group, an ethyl group, an n- or i-propyl group and an n-, i-, s- or t-butyl group, and preferable examples are a methyl group and an ethyl group. A more preferable example is a methyl group.

Specific examples of the linear or branched alkoxy groups having 1–6 carbon atoms include a methoxy group, an ethoxy group, an n- or i-propyloxy group, an n-, i-, s- or t-butyloxy group and a methylenedioxy group, and preferable examples are a methoxy group and an ethoxy group. A more preferable example is a methoxy group.

Specific examples of the linear or branched alkylthio group having 1–6 carbon atoms include a methylthio group, an ethylthio group, an n- or i-propylthio group and an n-, i-, s- or t-butylthio group, and preferable examples are a methylthio group and an ethylthio group. A more preferable example is a methylthio group.

Specific examples of the linear or branched alkylsulfonyl group having 1–6 carbon atoms include a methylsulfonyl group, an ethylsulfonyl group, an n- or i-propylsulfonyl group and an n-, i-, s- or t-butylsulfonyl group, and preferable examples are a methylsulfonyl group and an ethylsulfonyl group. A more preferable example is a methylsulfonyl group.

Specific examples of the linear or branched acyl group having 1–6 carbon atoms include an acetyl group, an ethylcarbonyl group, an n- or i-propylcarbonyl group and an n-, i-, s- or t-butylcarbonyl group, and preferable examples are an acetyl group and an ethylcarbonyl group. A more preferable example is an acetyl group.

Specific examples of the linear or branched acylamino group having 1–6 carbon atoms include an acetylamino group, an ethylcarbonylamino group, an n- or i-propylcarbonylamino group and an n-, i-, s- or t-butylcarbonylamino group, and preferable examples are an acetylamino group and an ethylcarbonylamino group. A more preferable example is an acetylamino group.

Specific examples of the trihalomethyl group include a trifluoromethyl group, a tribromomethyl group and a trichloromethyl group.

X represents a —CH═ group or nitrogen atom, and a preferable example is a —CH═ group.

Preferable examples of the compounds represented by the above formula (1) include various groups of compounds composed by combining each of the groups previously described as preferable examples. Although there is no intention of limiting these groups, those described in the following table are particularly preferable. In particular, preferable examples of those compounds in the table include compound Nos. 34, 38, 39, 41, 42, 52, 54, 56, 58, 59, 63, 135, 137, 148, 152, 154, 244, 340, 436, 514, 519, 521, 532, 534, 536, 538, 615, 628, 1112 and 1114.

Furthermore, A1 through A3 and J1 through J32 in the following table are groups represented with the following formulas. In the formulas, although E, G, M, m and X are as defined above, they are described hereinbelow using representative examples, namely E is COOH, G is $CH_2$, M is S (m being 0) or a single bond (indicated with "—" in the table) and X is —CH═. However, it is not intended that the present invention is limited to these compounds.

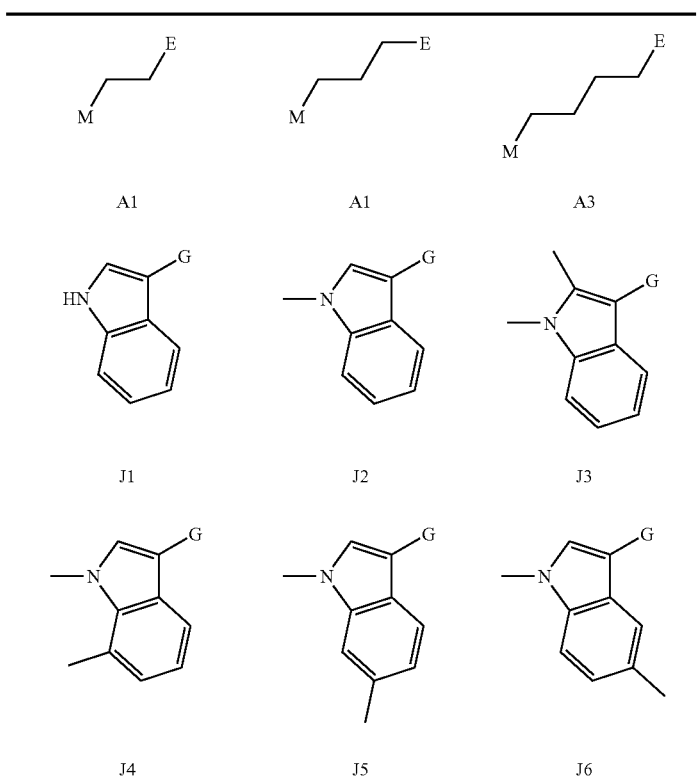

-continued
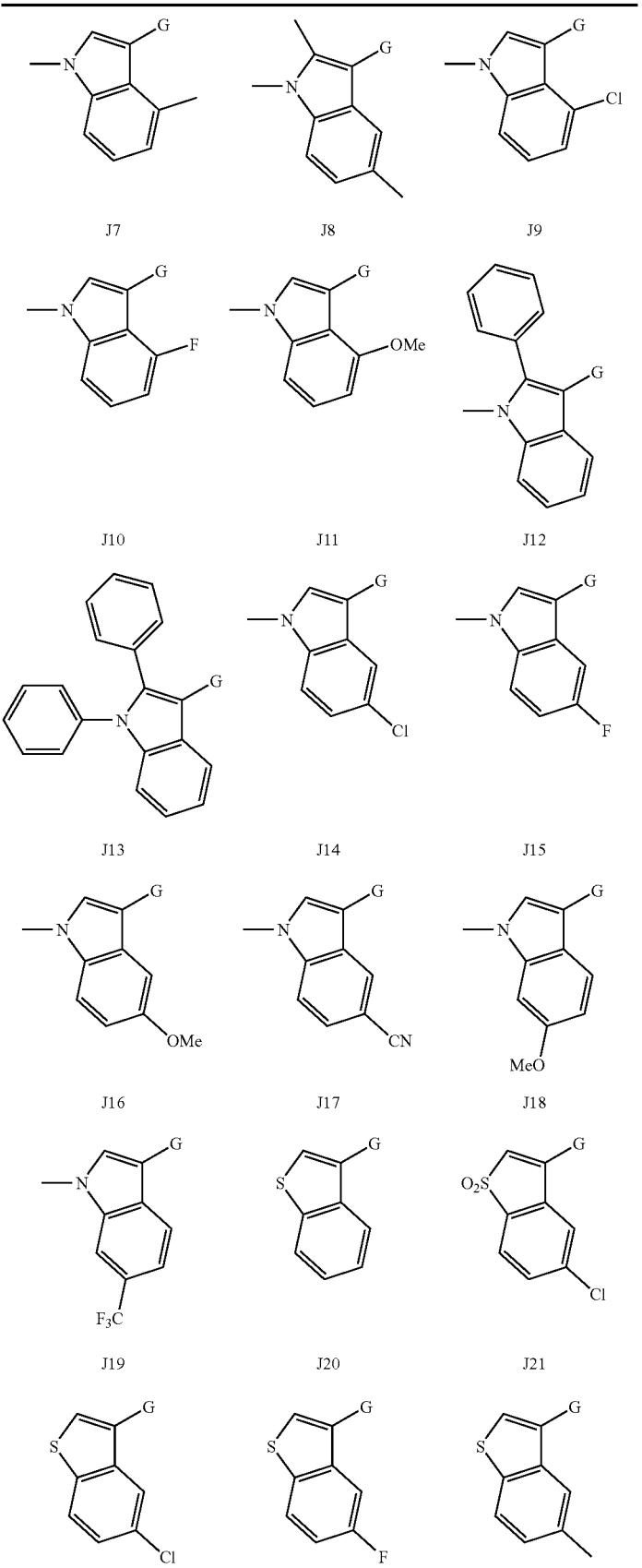

-continued
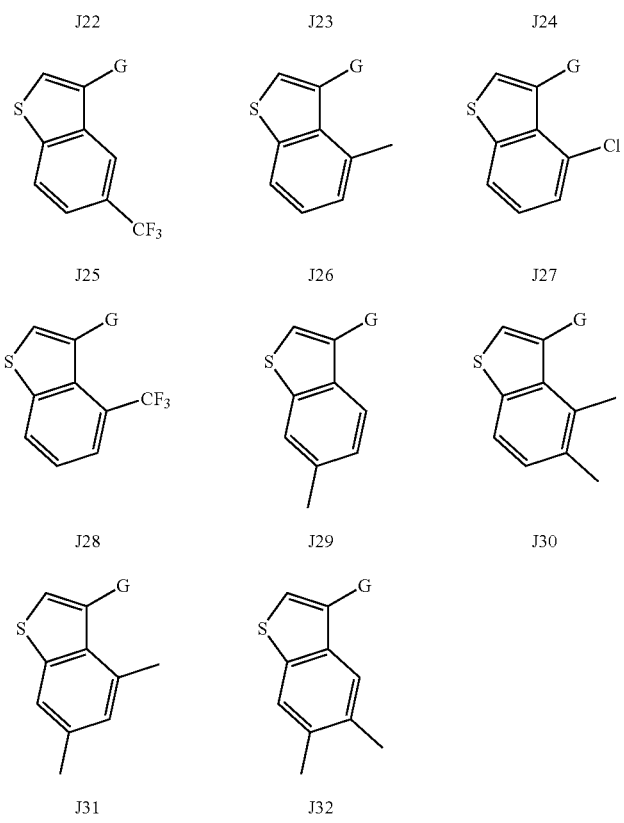
| Compound No. | R₁ | R₂ | A | J | M |
|---|---|---|---|---|---|
| 1 | H | H | A1 | J1 | S |
| 2 | H | H | A1 | J2 | S |
| 3 | H | H | A1 | J3 | S |
| 4 | H | H | A1 | J4 | S |
| 5 | H | H | A1 | J5 | S |
| 6 | H | H | A1 | J6 | S |
| 7 | H | H | A1 | J7 | S |
| 8 | H | H | A1 | J8 | S |
| 9 | H | H | A1 | J9 | S |
| 10 | H | H | A1 | J10 | S |
| 11 | H | H | A1 | J11 | S |
| 12 | H | H | A1 | J12 | S |
| 13 | H | H | A1 | J13 | S |
| 14 | H | H | A1 | J14 | S |
| 15 | H | H | A1 | J15 | S |
| 16 | H | H | A1 | J16 | S |
| 17 | H | H | A1 | J17 | S |
| 18 | H | H | A1 | J18 | S |
| 19 | H | H | A1 | J19 | S |
| 20 | H | H | A1 | J20 | S |
| 21 | H | H | A1 | J21 | S |
| 22 | H | H | A1 | J22 | S |
| 23 | H | H | A1 | J23 | S |
| 24 | H | H | A1 | J24 | S |
| 25 | H | H | A1 | J25 | S |
| 26 | H | H | A1 | J26 | S |
| 27 | H | H | A1 | J27 | S |
| 28 | H | H | A1 | J28 | S |
| 29 | H | H | A1 | J29 | S |
| 30 | H | H | A1 | J30 | S |
| 31 | H | H | A1 | J31 | S |
| 32 | H | H | A1 | J32 | S |
| 33 | H | H | A2 | J1 | S |
| 34 | H | H | A2 | J2 | S |
| 35 | H | H | A2 | J3 | S |
| 36 | H | H | A2 | J4 | S |
| 37 | H | H | A2 | J5 | S |

-continued

| | | | | | |
|---|---|---|---|---|---|
| 38 | H | H | A2 | J6 | S |
| 39 | H | H | A2 | J7 | S |
| 40 | H | H | A2 | J8 | S |
| 41 | H | H | A2 | J9 | S |
| 42 | H | H | A2 | J10 | S |
| 43 | H | H | A2 | J11 | S |
| 44 | H | H | A2 | J12 | S |
| 45 | H | H | A2 | J13 | S |
| 46 | H | H | A2 | J14 | S |
| 47 | H | H | A2 | J15 | S |
| 48 | H | H | A2 | J16 | S |
| 49 | H | H | A2 | J17 | S |
| 50 | H | H | A2 | J18 | S |
| 51 | H | H | A2 | J19 | S |
| 52 | H | H | A2 | J20 | S |
| 53 | H | H | A2 | J21 | S |
| 54 | H | H | A2 | J22 | S |
| 55 | H | H | A2 | J23 | S |
| 56 | H | H | A2 | J24 | S |
| 57 | H | H | A2 | J25 | S |
| 58 | H | H | A2 | J26 | S |
| 59 | H | H | A2 | J27 | S |
| 60 | H | H | A2 | J28 | S |
| 61 | H | H | A2 | J29 | S |
| 62 | H | H | A2 | J30 | S |
| 63 | H | H | A2 | J31 | S |
| 64 | H | H | A2 | J32 | S |
| 65 | H | H | A3 | J1 | S |
| 66 | H | H | A3 | J2 | S |
| 67 | H | H | A3 | J3 | S |
| 68 | H | H | A3 | J4 | S |
| 69 | H | H | A3 | J5 | S |
| 70 | H | H | A3 | J6 | S |
| 71 | H | H | A3 | J7 | S |
| 72 | H | H | A3 | J8 | S |
| 73 | H | H | A3 | J9 | S |
| 74 | H | H | A3 | J10 | S |
| 75 | H | H | A3 | J11 | S |
| 76 | H | H | A3 | J12 | S |
| 77 | H | H | A3 | J13 | S |
| 78 | H | H | A3 | J14 | S |
| 79 | H | H | A3 | J15 | S |
| 80 | H | H | A3 | J16 | S |
| 81 | H | H | A3 | J17 | S |
| 82 | H | H | A3 | J18 | S |
| 83 | H | H | A3 | J19 | S |
| 84 | H | H | A3 | J20 | S |
| 85 | H | H | A3 | J21 | S |
| 86 | H | H | A3 | J22 | S |
| 87 | H | H | A3 | J23 | S |
| 88 | H | H | A3 | J24 | S |
| 89 | H | H | A3 | J25 | S |
| 90 | H | H | A3 | J26 | S |
| 91 | H | H | A3 | J27 | S |
| 92 | H | H | A3 | J28 | S |
| 93 | H | H | A3 | J29 | S |
| 94 | H | H | A3 | J30 | S |
| 95 | H | H | A3 | J31 | S |
| 96 | H | H | A3 | J32 | S |
| 97 | MeO | H | A1 | J1 | S |
| 98 | MeO | H | A1 | J2 | S |
| 99 | MeO | H | A1 | J3 | S |
| 100 | MeO | H | A1 | J4 | S |
| 101 | MeO | H | A1 | J5 | S |
| 102 | MeO | H | A1 | J6 | S |
| 103 | MeO | H | A1 | J7 | S |
| 104 | MeO | H | A1 | J8 | S |
| 105 | MeO | H | A1 | J9 | S |
| 106 | MeO | H | A1 | J10 | S |
| 107 | MeO | H | A1 | J11 | S |
| 108 | MeO | H | A1 | J12 | S |
| 109 | MeO | H | A1 | J13 | S |
| 110 | MeO | H | A1 | J14 | S |
| 111 | MeO | H | A1 | J15 | S |
| 112 | MeO | H | A1 | J16 | S |
| 113 | MeO | H | A1 | J17 | S |
| 114 | MeO | H | A1 | J18 | S |
| 115 | MeO | H | A1 | J19 | S |
| 116 | MeO | H | A1 | J20 | S |

-continued

| | | | | | |
|---|---|---|---|---|---|
| 117 | MeO | H | A1 | J21 | S |
| 118 | MeO | H | A1 | J22 | S |
| 119 | MeO | H | A1 | J23 | S |
| 120 | MeO | H | A1 | J24 | S |
| 121 | MeO | H | A1 | J25 | S |
| 122 | MeO | H | A1 | J26 | S |
| 123 | MeO | H | A1 | J27 | S |
| 124 | MeO | H | A1 | J28 | S |
| 125 | MeO | H | A1 | J29 | S |
| 126 | MeO | H | A1 | J30 | S |
| 127 | MeO | H | A1 | J31 | S |
| 128 | MeO | H | A1 | J32 | S |
| 129 | MeO | H | A2 | J1 | S |
| 130 | MeO | H | A2 | J2 | S |
| 131 | MeO | H | A2 | J3 | S |
| 132 | MeO | H | A2 | J4 | S |
| 133 | MeO | H | A2 | J5 | S |
| 134 | MeO | H | A2 | J6 | S |
| 135 | MeO | H | A2 | J7 | S |
| 136 | MeO | H | A2 | J8 | S |
| 137 | MeO | H | A2 | J9 | S |
| 138 | MeO | H | A2 | J10 | S |
| 139 | MeO | H | A2 | J11 | S |
| 140 | MeO | H | A2 | J12 | S |
| 141 | MeO | H | A2 | J13 | S |
| 142 | MeO | H | A2 | J14 | S |
| 143 | MeO | H | A2 | J15 | S |
| 144 | MeO | H | A2 | J16 | S |
| 145 | MeO | H | A2 | J17 | S |
| 146 | MeO | H | A2 | J18 | S |
| 147 | MeO | H | A2 | J19 | S |
| 148 | MeO | H | A2 | J20 | S |
| 149 | MeO | H | A2 | J21 | S |
| 150 | MeO | H | A2 | J22 | S |
| 151 | MeO | H | A2 | J23 | S |
| 152 | MeO | H | A2 | J24 | S |
| 153 | MeO | H | A2 | J25 | S |
| 154 | MeO | H | A2 | J26 | S |
| 155 | MeO | H | A2 | J27 | S |
| 156 | MeO | H | A2 | J28 | S |
| 157 | MeO | H | A2 | J29 | S |
| 158 | MeO | H | A2 | J30 | S |
| 159 | MeO | H | A2 | J31 | S |
| 160 | MeO | H | A2 | J32 | S |
| 161 | MeO | H | A3 | J1 | S |
| 162 | MeO | H | A3 | J2 | S |
| 163 | MeO | H | A3 | J3 | S |
| 164 | MeO | H | A3 | J4 | S |
| 165 | MeO | H | A3 | J5 | S |
| 166 | MeO | H | A3 | J6 | S |
| 167 | MeO | H | A3 | J7 | S |
| 168 | MeO | H | A3 | J8 | S |
| 169 | MeO | H | A3 | J9 | S |
| 170 | MeO | H | A3 | J10 | S |
| 171 | MeO | H | A3 | J11 | S |
| 172 | MeO | H | A3 | J12 | S |
| 173 | MeO | H | A3 | J13 | S |
| 174 | MeO | H | A3 | J14 | S |
| 175 | MeO | H | A3 | J15 | S |
| 176 | MeO | H | A3 | J16 | S |
| 177 | MeO | H | A3 | J17 | S |
| 178 | MeO | H | A3 | J18 | S |
| 179 | MeO | H | A3 | J19 | S |
| 180 | MeO | H | A3 | J20 | S |
| 181 | MeO | H | A3 | J21 | S |
| 182 | NeO | H | A3 | J22 | S |
| 183 | MeO | H | A3 | J23 | S |
| 184 | MeO | H | A3 | J24 | S |
| 185 | MeO | H | A3 | J25 | S |
| 186 | MeO | H | A3 | J26 | S |
| 187 | MeO | H | A3 | J27 | S |
| 188 | MeO | H | A3 | J28 | S |
| 189 | MeO | H | A3 | J29 | S |
| 190 | MeO | H | A3 | J30 | S |
| 191 | MeO | H | A3 | J31 | S |
| 192 | MeO | H | A3 | J32 | S |
| 193 | CN | H | A1 | J1 | S |
| 194 | CN | H | A1 | J2 | S |
| 195 | CN | H | A1 | J3 | S |

-continued

| | | | | | |
|---|---|---|---|---|---|
| 196 | CN | H | A1 | J4 | S |
| 197 | CN | H | A1 | J5 | S |
| 198 | CN | H | A1 | J6 | S |
| 199 | CN | H | A1 | J7 | S |
| 200 | CN | H | A1 | J8 | S |
| 201 | CN | H | A1 | J9 | S |
| 202 | CN | H | A1 | J10 | S |
| 203 | CN | H | A1 | J11 | S |
| 204 | CN | H | A1 | J12 | S |
| 205 | CN | H | A1 | J13 | S |
| 206 | CN | H | A1 | J14 | S |
| 207 | CN | H | A1 | J15 | S |
| 208 | CN | H | A1 | J16 | S |
| 209 | CN | H | A1 | J17 | S |
| 210 | CN | H | A1 | J18 | S |
| 211 | CN | H | A1 | J19 | S |
| 212 | CN | H | A1 | J20 | S |
| 213 | CN | H | A1 | J21 | S |
| 214 | CN | H | A1 | J22 | S |
| 215 | CN | H | A1 | J23 | S |
| 216 | CN | H | A1 | J24 | S |
| 217 | CN | H | A1 | J25 | S |
| 218 | CN | H | A1 | J26 | S |
| 219 | CN | H | A1 | J27 | S |
| 220 | CN | H | A1 | J28 | S |
| 221 | CN | H | A1 | J29 | S |
| 222 | CN | H | A1 | J30 | S |
| 223 | CN | H | A1 | J31 | S |
| 224 | CN | H | A1 | J32 | S |
| 225 | CN | H | A2 | J1 | S |
| 226 | CN | H | A2 | J2 | S |
| 227 | CN | H | A2 | J3 | S |
| 228 | CN | H | A2 | J4 | S |
| 229 | CN | H | A2 | J5 | S |
| 230 | CN | H | A2 | J6 | S |
| 231 | CN | H | A2 | J7 | S |
| 232 | CN | H | A2 | J8 | S |
| 233 | CN | H | A2 | J9 | S |
| 234 | CN | H | A2 | J10 | S |
| 235 | CN | H | A2 | J11 | S |
| 236 | CN | H | A2 | J12 | S |
| 237 | CN | H | A2 | J13 | S |
| 238 | CN | H | A2 | J14 | S |
| 239 | CN | H | A2 | J15 | S |
| 240 | CN | H | A2 | J16 | S |
| 241 | CN | H | A2 | J17 | S |
| 242 | CN | H | A2 | J18 | S |
| 243 | CN | H | A2 | J19 | S |
| 244 | CN | H | A2 | J20 | S |
| 245 | CN | H | A2 | J21 | S |
| 246 | CN | H | A2 | J22 | S |
| 247 | CN | H | A2 | J23 | S |
| 248 | CN | H | A2 | J24 | S |
| 249 | CN | H | A2 | J25 | S |
| 250 | CN | H | A2 | J26 | S |
| 251 | CN | H | A2 | J27 | S |
| 252 | CN | H | A2 | J28 | S |
| 253 | CN | H | A2 | J29 | S |
| 254 | CN | H | A2 | J30 | S |
| 255 | CN | H | A2 | J31 | S |
| 256 | CN | H | A2 | J32 | S |
| 257 | CN | H | A3 | J1 | S |
| 258 | CN | H | A3 | J2 | S |
| 259 | CN | H | A3 | J3 | S |
| 260 | CN | H | A3 | J4 | S |
| 261 | CN | H | A3 | J5 | S |
| 262 | CN | H | A3 | J6 | S |
| 263 | CN | H | A3 | J7 | S |
| 264 | CN | H | A3 | J8 | S |
| 265 | CN | H | A3 | J9 | S |
| 266 | CN | H | A3 | J10 | S |
| 267 | CN | H | A3 | J11 | S |
| 268 | CN | H | A3 | J12 | S |
| 269 | CN | H | A3 | J13 | S |
| 270 | CN | H | A3 | J14 | S |
| 271 | CN | H | A3 | J15 | S |
| 272 | CN | H | A3 | J16 | S |
| 273 | CN | H | A3 | J17 | S |
| 274 | CN | H | A3 | J18 | S |

-continued

| | | | | | |
|---|---|---|---|---|---|
| 275 | CN | H | A3 | J19 | S |
| 276 | CN | H | A3 | J20 | S |
| 277 | CN | H | A3 | J21 | S |
| 278 | CN | H | A3 | J22 | S |
| 279 | CN | H | A3 | J23 | S |
| 280 | CN | H | A3 | J24 | S |
| 281 | CN | H | A3 | J25 | S |
| 282 | CN | H | A3 | J26 | S |
| 283 | CN | H | A3 | J27 | S |
| 284 | CN | H | A3 | J28 | S |
| 285 | CN | H | A3 | J29 | S |
| 286 | CN | H | A3 | J30 | S |
| 287 | CN | H | A3 | J31 | S |
| 288 | CN | H | A3 | J32 | S |
| 289 | Me | H | A1 | J1 | S |
| 290 | Me | H | A1 | J2 | S |
| 291 | Me | H | A1 | J3 | S |
| 292 | Me | H | A1 | J4 | S |
| 293 | Me | H | A1 | J5 | S |
| 294 | Me | H | A1 | J6 | S |
| 295 | Me | H | A1 | J7 | S |
| 296 | Me | H | A1 | J8 | S |
| 297 | Me | H | A1 | J9 | S |
| 298 | Me | H | A1 | J10 | S |
| 299 | Me | H | A1 | J11 | S |
| 300 | Me | H | A1 | J12 | S |
| 301 | Me | H | A1 | J13 | S |
| 302 | Me | H | A1 | J14 | S |
| 303 | Me | H | A1 | J15 | S |
| 304 | Me | H | A1 | J16 | S |
| 305 | Me | H | A1 | J17 | S |
| 306 | Me | H | A1 | J18 | S |
| 307 | Me | H | A1 | J19 | S |
| 308 | Me | H | A1 | J20 | S |
| 309 | Me | H | A1 | J21 | S |
| 310 | Me | H | A1 | J22 | S |
| 311 | Me | H | A1 | J23 | S |
| 312 | Me | H | A1 | J24 | S |
| 313 | Me | H | A1 | J25 | S |
| 314 | Me | H | A1 | J26 | S |
| 315 | Me | H | A1 | J27 | S |
| 316 | Me | H | A1 | J28 | S |
| 317 | Me | H | A1 | J29 | S |
| 318 | Me | H | A1 | J30 | S |
| 319 | Me | H | A1 | J31 | S |
| 320 | Me | H | A1 | J32 | S |
| 321 | Me | H | A2 | J1 | S |
| 322 | Me | H | A2 | J2 | S |
| 323 | Me | H | A2 | J3 | S |
| 324 | Me | H | A2 | J4 | S |
| 325 | Me | H | A2 | J5 | S |
| 326 | Me | H | A2 | J6 | S |
| 327 | Me | H | A2 | J7 | S |
| 328 | Me | H | A2 | J8 | S |
| 329 | Me | H | A2 | J9 | S |
| 330 | Me | H | A2 | J10 | S |
| 331 | Me | H | A2 | J11 | S |
| 332 | Me | H | A2 | J12 | S |
| 333 | Me | H | A2 | J13 | S |
| 334 | Me | H | A2 | J14 | S |
| 335 | Me | H | A2 | J15 | S |
| 336 | Me | H | A2 | J16 | S |
| 337 | Me | H | A2 | J17 | S |
| 338 | Me | H | A2 | J18 | S |
| 339 | Me | H | A2 | J19 | S |
| 340 | Me | H | A2 | J20 | S |
| 341 | Me | H | A2 | J21 | S |
| 342 | Me | H | A2 | J22 | S |
| 343 | Me | H | A2 | J23 | S |
| 344 | Me | H | A2 | J24 | S |
| 345 | Me | H | A2 | J25 | S |
| 346 | Me | H | A2 | J26 | S |
| 347 | Me | H | A2 | J27 | S |
| 348 | Me | H | A2 | J28 | S |
| 349 | Me | H | A2 | J29 | S |
| 350 | Me | H | A2 | J30 | S |
| 351 | Me | H | A2 | J31 | S |
| 352 | Me | H | A2 | J32 | S |
| 353 | Me | H | A3 | J1 | S |

-continued

| | | | | | |
|---|---|---|---|---|---|
| 354 | Me | H | A3 | J2 | S |
| 355 | Me | H | A3 | J3 | S |
| 356 | Me | H | A3 | J4 | S |
| 357 | Me | H | A3 | J5 | S |
| 358 | Me | H | A3 | J6 | S |
| 359 | Me | H | A3 | J7 | S |
| 360 | Me | H | A3 | J8 | S |
| 361 | Me | H | A3 | J9 | S |
| 362 | Me | H | A3 | J10 | S |
| 363 | Me | H | A3 | J11 | S |
| 364 | Me | H | A3 | J12 | S |
| 365 | Me | H | A3 | J13 | S |
| 366 | Me | H | A3 | J14 | S |
| 367 | Me | H | A3 | J15 | S |
| 368 | Me | H | A3 | J16 | S |
| 369 | Me | H | A3 | J17 | S |
| 370 | Me | H | A3 | J18 | S |
| 371 | Me | H | A3 | J19 | S |
| 372 | Me | H | A3 | J20 | S |
| 373 | Me | H | A3 | J21 | S |
| 374 | Me | H | A3 | J22 | S |
| 375 | Me | H | A3 | J23 | S |
| 376 | Me | H | A3 | J24 | S |
| 377 | Me | H | A3 | J25 | S |
| 378 | Me | H | A3 | J26 | S |
| 379 | Me | H | A3 | J27 | S |
| 380 | Me | H | A3 | J28 | S |
| 381 | Me | H | A3 | J29 | S |
| 382 | Me | H | A3 | J30 | S |
| 383 | Me | H | A3 | J31 | S |
| 384 | Me | H | A3 | J32 | S |
| 385 | H | Me | A1 | J1 | S |
| 386 | H | Me | A1 | J2 | S |
| 387 | H | Me | A1 | J3 | S |
| 388 | H | Me | A1 | J4 | S |
| 389 | H | Me | A1 | J5 | S |
| 390 | H | Me | A1 | J6 | S |
| 391 | H | Me | A1 | J7 | S |
| 392 | H | Me | A1 | J8 | S |
| 393 | H | Me | A1 | J9 | S |
| 394 | H | Me | A1 | J10 | S |
| 395 | H | Me | A1 | J11 | S |
| 396 | H | Me | A1 | J12 | S |
| 397 | H | Me | A1 | J13 | S |
| 398 | H | Me | A1 | J14 | S |
| 399 | H | Me | A1 | J15 | S |
| 400 | H | Me | A1 | J16 | S |
| 401 | H | Me | A1 | J17 | S |
| 402 | H | Me | A1 | J18 | S |
| 403 | H | Me | A1 | J19 | S |
| 404 | H | Me | A1 | J20 | S |
| 405 | H | Me | A1 | J21 | S |
| 406 | H | Me | A1 | J22 | S |
| 407 | H | Me | A1 | J23 | S |
| 408 | H | Me | A1 | J24 | S |
| 409 | H | Me | A1 | J25 | S |
| 410 | H | Me | A1 | J26 | S |
| 411 | H | Me | A1 | J27 | S |
| 412 | H | Me | A1 | J28 | S |
| 413 | H | Me | A1 | J29 | S |
| 414 | H | Me | A1 | J30 | S |
| 415 | H | Me | A1 | J31 | S |
| 416 | H | Me | A1 | J32 | S |
| 417 | H | Me | A2 | J1 | S |
| 418 | H | Me | A2 | J2 | S |
| 419 | H | Me | A2 | J3 | S |
| 420 | H | Me | A2 | J4 | S |
| 421 | H | Me | A2 | J5 | S |
| 422 | H | Me | A2 | J6 | S |
| 423 | H | Me | A2 | J7 | S |
| 424 | H | Me | A2 | J8 | S |
| 425 | H | Me | A2 | J9 | S |
| 426 | H | Me | A2 | J10 | S |
| 427 | H | Me | A2 | J11 | S |
| 428 | H | Me | A2 | J12 | S |
| 429 | H | Me | A2 | J13 | S |
| 430 | H | Me | A2 | J14 | S |
| 431 | H | Me | A2 | J15 | S |
| 432 | H | Me | A2 | J16 | S |

| | | | | | |
|---|---|---|---|---|---|
| 433 | H | Me | A2 | J17 | S |
| 434 | H | Me | A2 | J18 | S |
| 435 | H | Me | A2 | J19 | S |
| 436 | H | Me | A2 | J20 | S |
| 437 | H | Me | A2 | J21 | S |
| 438 | H | Me | A2 | J22 | S |
| 439 | H | Me | A2 | J23 | S |
| 440 | H | Me | A2 | J24 | S |
| 441 | H | Me | A3 | J25 | S |
| 442 | H | Me | A2 | J26 | S |
| 443 | H | Me | A2 | J27 | S |
| 444 | H | Me | A2 | J28 | S |
| 445 | H | Me | A2 | J29 | S |
| 446 | H | Me | A2 | J30 | S |
| 447 | H | Me | A2 | J31 | S |
| 448 | H | Me | A2 | J32 | S |
| 449 | H | Me | A3 | J1 | S |
| 450 | H | Me | A3 | J2 | S |
| 451 | H | Me | A3 | J3 | S |
| 452 | H | Me | A3 | J4 | S |
| 453 | H | Me | A3 | J5 | S |
| 454 | H | Me | A3 | J6 | S |
| 455 | H | Me | A3 | J7 | S |
| 456 | H | Me | A3 | J8 | S |
| 457 | H | Me | A3 | J9 | S |
| 458 | H | Me | A3 | J10 | S |
| 459 | H | Me | A3 | J11 | S |
| 460 | H | Me | A3 | J12 | S |
| 461 | H | Me | A3 | J13 | S |
| 462 | H | Me | A3 | J14 | S |
| 463 | H | Me | A3 | J15 | S |
| 464 | H | Me | A3 | J16 | S |
| 465 | H | Me | A3 | J17 | S |
| 466 | H | Me | A3 | J18 | S |
| 467 | H | Me | A3 | J19 | S |
| 468 | H | Me | A3 | J20 | S |
| 469 | H | Me | A3 | J21 | S |
| 470 | H | Me | A3 | J22 | S |
| 471 | H | Me | A3 | J23 | S |
| 472 | H | Me | A3 | J24 | S |
| 473 | H | Me | A3 | J25 | S |
| 474 | H | Me | A3 | J26 | S |
| 475 | H | Me | A3 | J27 | S |
| 476 | H | Me | A3 | J28 | S |
| 477 | H | Me | A3 | J29 | S |
| 478 | H | Me | A3 | J30 | S |
| 479 | H | Me | A3 | J31 | S |
| 480 | H | Me | A3 | J32 | S |
| 481 | Me | Me | A1 | J1 | S |
| 482 | Me | Me | A1 | J2 | S |
| 483 | Me | Me | A1 | J3 | S |
| 484 | Me | Me | A1 | J4 | S |
| 485 | Me | Me | A1 | J5 | S |
| 486 | Me | Me | A1 | J6 | S |
| 487 | Me | Me | A1 | J7 | S |
| 488 | Me | Me | A1 | J8 | S |
| 489 | Me | Me | A1 | J9 | S |
| 490 | Me | Me | A1 | J10 | S |
| 491 | Me | Me | A1 | J11 | S |
| 492 | Me | Me | A1 | J12 | S |
| 493 | Me | Me | A1 | J13 | S |
| 494 | Me | Me | A1 | J14 | S |
| 495 | Me | Me | A1 | J15 | S |
| 496 | Me | Me | A1 | J16 | S |
| 497 | Me | Me | A1 | J17 | S |
| 498 | Me | Me | A1 | J18 | S |
| 499 | Me | Me | A1 | J19 | S |
| 500 | Me | Me | A1 | J20 | S |
| 501 | Me | Me | A1 | J21 | S |
| 502 | Me | Me | A1 | J22 | S |
| 503 | Me | Me | A1 | J23 | S |
| 504 | Me | Me | A1 | J24 | S |
| 505 | Me | Me | A1 | J25 | S |
| 506 | Me | Me | A1 | J26 | S |
| 507 | Me | Me | A1 | J27 | S |
| 508 | Me | Me | A1 | J28 | S |
| 509 | Me | Me | A1 | J29 | S |
| 510 | Me | Me | A1 | J30 | S |
| 511 | Me | Me | A1 | J31 | S |

-continued

| | | | | | |
|---|---|---|---|---|---|
| 512 | Me | Me | A1 | J32 | S |
| 513 | Me | Me | A2 | J1 | S |
| 514 | Me | Me | A2 | J2 | S |
| 515 | Me | Me | A2 | J3 | S |
| 516 | Me | Me | A2 | J4 | S |
| 517 | Ne | Me | A2 | J5 | S |
| 518 | Me | Me | A2 | J6 | S |
| 519 | Me | Me | A2 | J7 | S |
| 520 | Me | Me | A2 | J8 | S |
| 521 | Me | Me | A2 | J9 | S |
| 522 | Me | Me | A2 | J10 | S |
| 523 | Me | Me | A2 | J11 | S |
| 524 | Me | Me | A2 | J12 | S |
| 525 | Me | Me | A2 | J13 | S |
| 526 | Me | Me | A2 | J14 | S |
| 257 | Me | Me | A2 | J15 | S |
| 528 | Me | Me | A2 | J16 | S |
| 529 | Me | Me | A2 | J17 | S |
| 530 | Me | Me | A2 | J18 | S |
| 531 | Me | Me | A2 | J19 | S |
| 532 | Me | Me | A2 | J20 | S |
| 533 | Me | Me | A2 | J21 | S |
| 534 | Me | Me | A2 | J22 | S |
| 535 | Me | Me | A2 | J23 | S |
| 536 | Me | Me | A2 | J24 | S |
| 537 | Me | Me | A2 | J25 | S |
| 538 | Me | Me | A2 | J26 | S |
| 539 | Me | Me | A2 | J27 | S |
| 540 | Me | Me | A2 | J28 | S |
| 541 | Me | Me | A2 | J29 | S |
| 542 | Me | Me | A2 | J30 | S |
| 543 | Me | Me | A2 | J31 | S |
| 544 | Me | Me | A2 | J32 | S |
| 545 | Me | Me | A3 | J1 | S |
| 546 | Me | Me | A3 | J2 | S |
| 547 | Me | Me | A3 | J3 | S |
| 548 | Me | Me | A3 | J4 | S |
| 549 | Me | Me | A3 | J5 | S |
| 550 | Me | Me | A3 | J6 | S |
| 551 | Me | Me | A3 | J7 | S |
| 552 | Me | Me | A3 | J8 | S |
| 553 | Me | Me | A3 | J9 | S |
| 554 | Me | Me | A3 | J10 | S |
| 555 | Me | Me | A3 | J11 | S |
| 556 | Me | Me | A3 | J12 | S |
| 557 | Me | Me | A3 | J13 | S |
| 558 | Me | Me | A3 | J14 | S |
| 559 | Me | Me | A3 | J15 | S |
| 560 | Me | Me | A3 | J16 | S |
| 561 | Me | Me | A3 | J17 | S |
| 562 | Me | Me | A3 | J18 | S |
| 563 | Me | Me | A3 | J19 | S |
| 564 | Me | Me | A3 | J20 | S |
| 565 | Me | Me | A3 | J21 | S |
| 566 | Me | Me | A3 | J22 | S |
| 567 | Me | Me | A3 | J23 | S |
| 568 | Me | Me | A3 | J24 | S |
| 569 | Me | Me | A3 | J25 | S |
| 570 | Me | Me | A3 | J26 | S |
| 571 | Me | Me | A3 | J27 | S |
| 572 | Me | Me | A3 | J28 | S |
| 573 | Me | Me | A3 | J29 | S |
| 574 | Me | Me | A3 | J30 | S |
| 575 | Me | Me | A3 | J31 | S |
| 576 | Me | Me | A3 | J32 | S |
| 577 | Cl | Cl | A1 | J1 | S |
| 578 | Cl | Cl | A1 | J2 | S |
| 579 | Cl | Cl | A1 | J3 | S |
| 580 | Cl | Cl | A1 | J4 | S |
| 581 | Cl | Cl | A1 | J5 | S |
| 582 | Cl | Cl | A1 | J6 | S |
| 583 | Cl | Cl | A1 | J7 | S |
| 584 | Cl | Cl | A1 | J8 | S |
| 585 | Cl | Cl | A1 | J9 | S |
| 586 | Cl | Cl | A1 | J10 | S |
| 587 | Cl | Cl | A1 | J11 | S |
| 588 | Cl | Cl | A1 | J12 | S |
| 589 | Cl | Cl | A1 | J13 | S |
| 590 | Cl | Cl | A1 | J14 | S |

|     |    |    |    |     |   |
|-----|----|----|----|-----|---|
| 591 | Cl | Cl | A1 | J15 | S |
| 592 | Cl | Cl | A1 | J16 | S |
| 593 | Cl | Cl | A1 | J17 | S |
| 594 | Cl | Cl | A1 | J18 | S |
| 595 | Cl | Cl | A1 | J19 | S |
| 596 | Cl | Cl | A1 | J20 | S |
| 597 | Cl | Cl | A1 | J21 | S |
| 598 | Cl | Cl | A1 | J22 | S |
| 599 | Cl | Cl | A1 | J23 | S |
| 600 | Cl | Cl | A1 | J24 | S |
| 601 | Cl | Cl | A1 | J25 | S |
| 602 | Cl | Cl | A1 | J26 | S |
| 603 | Cl | Cl | A1 | J27 | S |
| 604 | Cl | Cl | A1 | J28 | S |
| 605 | Cl | Cl | A1 | J29 | S |
| 606 | Cl | Cl | A1 | J30 | S |
| 607 | Cl | Cl | A1 | J31 | S |
| 608 | Cl | Cl | A1 | J32 | S |
| 609 | Cl | Cl | A2 | J1  | S |
| 610 | Cl | Cl | A2 | J2  | S |
| 611 | Cl | Cl | A2 | J3  | S |
| 612 | Cl | Cl | A2 | J4  | S |
| 613 | Cl | Cl | A2 | J5  | S |
| 614 | Cl | Cl | A2 | J6  | S |
| 615 | Cl | Cl | A2 | J7  | S |
| 616 | Cl | Cl | A2 | J8  | S |
| 617 | Cl | Cl | A2 | J9  | S |
| 618 | Cl | Cl | A2 | J10 | S |
| 619 | Cl | Cl | A2 | J11 | S |
| 620 | Cl | Cl | A2 | J12 | S |
| 621 | Cl | Cl | A2 | J13 | S |
| 622 | Cl | Cl | A2 | J14 | S |
| 623 | Cl | Cl | A2 | J15 | S |
| 624 | Cl | Cl | A2 | J16 | S |
| 625 | Cl | Cl | A2 | J17 | S |
| 626 | Cl | Cl | A2 | J18 | S |
| 627 | Cl | Cl | A2 | J19 | S |
| 628 | Cl | Cl | A2 | J20 | S |
| 629 | Cl | Cl | A2 | J21 | S |
| 630 | Cl | Cl | A2 | J22 | S |
| 631 | Cl | Cl | A2 | J23 | S |
| 632 | Cl | Cl | A2 | J24 | S |
| 633 | Cl | Cl | A2 | J25 | S |
| 634 | Cl | Cl | A2 | J26 | S |
| 635 | Cl | Cl | A2 | J27 | S |
| 636 | Cl | Cl | A2 | J28 | S |
| 637 | Cl | Cl | A2 | J29 | S |
| 638 | Cl | Cl | A2 | J30 | S |
| 639 | Cl | Cl | A2 | J31 | S |
| 640 | Cl | Cl | A2 | J32 | S |
| 641 | Cl | Cl | A3 | J1  | S |
| 642 | Cl | Cl | A3 | J2  | S |
| 643 | Cl | Cl | A3 | J3  | S |
| 644 | Cl | Cl | A3 | J4  | S |
| 645 | Cl | Cl | A3 | J5  | S |
| 646 | Cl | Cl | A3 | J6  | S |
| 647 | Cl | Cl | A3 | J7  | S |
| 648 | Cl | Cl | A3 | J8  | S |
| 649 | Cl | Cl | A3 | J9  | S |
| 650 | Cl | Cl | A3 | J10 | S |
| 651 | Cl | Cl | A3 | J11 | S |
| 652 | Cl | Cl | A3 | J12 | S |
| 653 | Cl | Cl | A3 | J13 | S |
| 654 | Cl | Cl | A3 | J14 | S |
| 655 | Cl | Cl | A3 | J15 | S |
| 656 | Cl | Cl | A3 | J16 | S |
| 657 | Cl | Cl | A3 | J17 | S |
| 658 | Cl | Cl | A3 | J18 | S |
| 659 | Cl | Cl | A3 | J19 | S |
| 660 | Cl | Cl | A3 | J20 | S |
| 661 | Cl | Cl | A3 | J21 | S |
| 662 | Cl | Cl | A3 | J22 | S |
| 663 | Cl | Cl | A3 | J23 | S |
| 664 | Cl | Cl | A3 | J24 | S |
| 665 | Cl | Cl | A3 | J25 | S |
| 666 | Cl | Cl | A3 | J26 | S |
| 667 | Cl | Cl | A3 | J27 | S |
| 668 | Cl | Cl | A3 | J28 | S |
| 669 | Cl | Cl | A3 | J29 | S |

-continued

| | | | | | |
|---|---|---|---|---|---|
| 670 | Cl | Cl | A3 | J30 | S |
| 671 | Cl | Cl | A3 | J31 | S |
| 672 | Cl | Cl | A3 | J32 | S |
| 673 | H | H | A1 | J1 | — |
| 674 | H | H | A1 | J2 | — |
| 675 | H | H | A1 | J3 | — |
| 676 | H | H | A1 | J4 | — |
| 677 | H | H | A1 | J5 | — |
| 678 | H | H | A1 | J6 | — |
| 679 | H | H | A1 | J7 | — |
| 680 | H | H | A1 | J8 | — |
| 681 | H | H | A1 | J9 | — |
| 682 | H | H | A1 | J10 | — |
| 683 | H | H | A1 | J11 | — |
| 684 | H | H | A1 | J12 | — |
| 685 | H | H | A1 | J13 | — |
| 686 | H | H | A1 | J14 | — |
| 687 | H | H | A1 | J15 | — |
| 688 | H | H | A1 | J16 | — |
| 689 | H | H | A1 | J17 | — |
| 690 | H | H | A1 | J18 | — |
| 691 | H | H | A1 | J19 | — |
| 692 | H | H | A1 | J20 | — |
| 693 | H | H | A1 | J21 | — |
| 694 | H | H | A1 | J22 | — |
| 695 | H | H | A1 | J23 | — |
| 696 | H | H | A1 | J24 | — |
| 697 | H | H | A1 | J25 | — |
| 698 | H | H | A1 | J26 | — |
| 699 | H | H | A1 | J27 | — |
| 700 | H | H | A1 | J28 | — |
| 701 | H | H | A1 | J29 | — |
| 702 | H | H | A1 | J30 | — |
| 703 | H | H | A1 | J31 | — |
| 704 | H | H | A1 | J32 | — |
| 705 | H | H | A2 | J1 | — |
| 706 | H | H | A2 | J2 | — |
| 707 | H | H | A2 | J3 | — |
| 708 | H | H | A2 | J4 | — |
| 709 | H | H | A2 | J5 | — |
| 710 | H | H | A2 | J6 | — |
| 711 | H | H | A2 | J7 | — |
| 712 | H | H | A2 | J8 | — |
| 713 | H | H | A2 | J9 | — |
| 714 | H | H | A2 | J10 | — |
| 715 | H | H | A2 | J11 | — |
| 716 | H | H | A2 | J12 | — |
| 717 | H | H | A2 | J13 | — |
| 718 | H | H | A2 | J14 | — |
| 719 | H | H | A2 | J15 | — |
| 720 | H | H | A2 | J16 | — |
| 721 | H | H | A2 | J17 | — |
| 722 | H | H | A2 | J18 | — |
| 723 | H | H | A2 | J19 | — |
| 724 | H | H | A2 | J20 | — |
| 725 | H | H | A2 | J21 | — |
| 726 | H | H | A2 | J22 | — |
| 727 | H | H | A2 | J23 | — |
| 728 | H | H | A2 | J24 | — |
| 729 | H | H | A2 | J25 | — |
| 730 | H | H | A2 | J26 | — |
| 731 | H | H | A2 | J27 | — |
| 732 | H | H | A2 | J28 | — |
| 733 | H | H | A2 | J29 | — |
| 734 | H | H | A2 | J30 | — |
| 735 | H | H | A2 | J31 | — |
| 736 | H | H | A2 | J32 | — |
| 737 | H | H | A3 | J1 | — |
| 738 | H | H | A3 | J2 | — |
| 739 | H | H | A3 | J3 | — |
| 740 | H | H | A3 | J4 | — |
| 741 | H | H | A3 | J5 | — |
| 742 | H | H | A3 | J6 | — |
| 743 | H | H | A3 | J7 | — |
| 744 | H | H | A3 | J8 | — |
| 745 | H | H | A3 | J9 | — |
| 746 | H | H | A3 | J10 | — |
| 747 | H | H | A3 | J11 | — |
| 748 | H | H | A3 | J12 | — |

-continued

| | | | | | |
|---|---|---|---|---|---|
| 749 | H | H | A3 | J13 | — |
| 750 | H | H | A3 | J14 | — |
| 751 | H | H | A3 | J15 | — |
| 752 | H | H | A3 | J16 | — |
| 753 | H | H | A3 | J17 | — |
| 754 | H | H | A3 | J18 | — |
| 755 | H | H | A3 | J19 | — |
| 756 | H | H | A3 | J20 | — |
| 757 | H | H | A3 | J21 | — |
| 758 | H | H | A3 | J22 | — |
| 759 | H | H | A3 | J23 | — |
| 760 | H | H | A3 | J24 | — |
| 761 | H | H | A3 | J25 | — |
| 762 | H | H | A3 | J26 | — |
| 763 | H | H | A3 | J27 | — |
| 764 | H | H | A3 | J28 | — |
| 765 | H | H | A3 | J29 | — |
| 766 | H | H | A3 | J30 | — |
| 767 | H | H | A3 | J31 | — |
| 768 | H | H | A3 | J32 | — |
| 769 | MeO | H | A1 | J1 | — |
| 770 | MeO | H | A1 | J2 | — |
| 771 | MeO | H | A1 | J3 | — |
| 772 | MeO | H | A1 | J4 | — |
| 773 | MeO | H | A1 | J5 | — |
| 774 | MeO | H | A1 | J6 | — |
| 775 | MeO | H | A1 | J7 | — |
| 776 | MeO | H | A1 | J8 | — |
| 777 | MeO | H | A1 | J9 | — |
| 778 | MeO | H | A1 | J10 | — |
| 779 | MeO | H | A1 | J11 | — |
| 780 | MeO | H | A1 | J12 | — |
| 781 | MeO | H | A1 | J13 | — |
| 782 | MeO | H | A1 | J14 | — |
| 783 | MeO | H | A1 | J15 | — |
| 784 | MeO | H | A1 | J16 | — |
| 785 | MeO | H | A1 | J17 | — |
| 786 | MeO | H | A1 | J18 | — |
| 787 | MeO | H | A1 | J19 | — |
| 788 | MeO | H | A1 | J20 | — |
| 789 | MeO | H | A1 | J21 | — |
| 790 | MeO | H | A1 | J22 | — |
| 791 | MeO | H | A1 | J23 | — |
| 792 | MeO | H | A1 | J24 | — |
| 793 | MeO | H | A1 | J25 | — |
| 794 | MeO | H | A1 | J26 | — |
| 795 | MeO | H | A1 | J27 | — |
| 796 | MeO | H | A1 | J28 | — |
| 797 | MeO | H | A1 | J29 | — |
| 798 | MeO | H | A1 | J30 | — |
| 799 | MeO | H | A1 | J31 | — |
| 800 | MeO | H | A1 | J32 | — |
| 801 | MeO | H | A2 | J1 | — |
| 802 | MeO | H | A2 | J2 | — |
| 803 | MeO | H | A2 | J3 | — |
| 804 | MeO | H | A2 | J4 | — |
| 805 | MeO | H | A2 | J5 | — |
| 806 | MeO | H | A2 | J6 | — |
| 807 | MeO | H | A2 | J7 | — |
| 808 | MeO | H | A2 | J8 | — |
| 809 | MeO | H | A2 | J9 | — |
| 810 | MeO | H | A2 | J10 | — |
| 811 | MeO | H | A2 | J11 | — |
| 812 | MeO | H | A2 | J12 | — |
| 813 | MeO | H | A2 | J13 | — |
| 814 | MeO | H | A2 | J14 | — |
| 815 | MeO | H | A2 | J15 | — |
| 816 | MeO | H | A2 | J16 | — |
| 817 | MeO | H | A2 | J17 | — |
| 818 | MeO | H | A2 | J18 | — |
| 819 | MeO | H | A2 | J19 | — |
| 820 | NeO | H | A2 | J20 | — |
| 821 | MeO | H | A2 | J21 | — |
| 822 | MeO | H | A2 | J22 | — |
| 823 | MeO | H | A2 | J23 | — |
| 824 | MeO | H | A2 | J24 | — |
| 825 | MeO | H | A2 | J25 | — |
| 826 | MeO | H | A2 | J26 | — |
| 827 | MeO | H | A2 | J27 | — |

-continued

| | | | | | |
|---|---|---|---|---|---|
| 828 | MeO | H | A2 | J28 | — |
| 829 | MeO | H | A2 | J29 | — |
| 830 | MeO | H | A2 | J30 | — |
| 931 | MeO | H | A2 | J31 | — |
| 832 | MeO | H | A2 | J32 | — |
| 833 | MeO | H | A3 | J1 | — |
| 834 | MeO | H | A3 | J2 | — |
| 835 | MeO | H | A3 | J3 | — |
| 836 | MeO | H | A3 | J4 | — |
| 837 | MeO | H | A3 | J5 | — |
| 838 | MeO | H | A3 | J6 | — |
| 839 | MeO | H | A3 | J7 | — |
| 840 | MeO | H | A3 | J8 | — |
| 841 | MeO | H | A3 | J9 | — |
| 842 | MeO | H | A3 | J10 | — |
| 843 | MeO | H | A3 | J11 | — |
| 844 | MeO | H | A3 | J12 | — |
| 845 | MeO | H | A3 | J13 | — |
| 846 | MeO | H | A3 | J14 | — |
| 847 | MeO | H | A3 | J15 | — |
| 848 | MeO | H | A3 | J16 | — |
| 849 | MeO | H | A3 | J17 | — |
| 850 | MeO | H | A3 | J18 | — |
| 851 | MeO | H | A3 | J19 | — |
| 852 | MeO | H | A3 | J20 | — |
| 853 | MeO | H | A3 | J21 | — |
| 854 | MeO | H | A3 | J22 | — |
| 855 | MeO | H | A3 | J23 | — |
| 856 | MeO | H | A3 | J24 | — |
| 857 | MeO | H | A3 | J25 | — |
| 858 | MeO | H | A3 | J26 | — |
| 859 | MeO | H | A3 | J27 | — |
| 860 | MeO | H | A3 | J28 | — |
| 861 | MeO | H | A3 | J29 | — |
| 862 | MeO | H | A3 | J30 | — |
| 863 | MeO | H | A3 | J31 | — |
| 864 | MeO | H | A3 | J32 | — |
| 865 | CN | H | A1 | J1 | — |
| 866 | CN | H | A1 | J2 | — |
| 867 | CN | H | A1 | J3 | — |
| 868 | CN | H | A1 | J4 | — |
| 869 | CN | H | A1 | J5 | — |
| 870 | CN | H | A1 | J6 | — |
| 871 | CN | H | A1 | J7 | — |
| 872 | CN | H | A1 | J8 | — |
| 873 | CN | H | A1 | J9 | — |
| 874 | CN | H | A1 | J10 | — |
| 875 | CN | H | A1 | J11 | — |
| 876 | CN | H | A1 | J12 | — |
| 877 | CN | H | A1 | J13 | — |
| 878 | CN | H | A1 | J14 | — |
| 879 | CN | H | A1 | J15 | — |
| 880 | CN | H | A1 | J16 | — |
| 881 | CN | H | A1 | J17 | — |
| 882 | CN | H | A1 | J18 | — |
| 883 | CN | H | A1 | J19 | — |
| 884 | CN | H | A1 | J20 | — |
| 885 | CN | H | A1 | J21 | — |
| 886 | CN | H | A1 | J22 | — |
| 887 | CN | H | A1 | J23 | — |
| 888 | CN | H | A1 | J24 | — |
| 889 | CN | H | A1 | J25 | — |
| 890 | CN | H | A1 | J26 | — |
| 891 | CN | H | A1 | J27 | — |
| 892 | CN | H | A1 | J28 | — |
| 893 | CN | H | A1 | J29 | — |
| 894 | CN | H | A1 | J30 | — |
| 895 | CN | H | A1 | J31 | — |
| 896 | CN | H | A1 | J32 | — |
| 897 | CN | H | A2 | J1 | — |
| 898 | CN | H | A2 | J2 | — |
| 899 | CN | H | A2 | J3 | — |
| 900 | CN | H | A2 | J4 | — |
| 901 | CN | H | A2 | J5 | — |
| 902 | CN | H | A2 | J6 | — |
| 903 | CN | H | A2 | J7 | — |
| 904 | CN | H | A2 | J8 | — |
| 905 | CN | H | A2 | J9 | — |
| 906 | CN | H | A2 | J10 | — |

-continued

| | | | | | |
|---|---|---|---|---|---|
| 907 | CN | H | A2 | J11 | — |
| 908 | CN | H | A2 | J12 | — |
| 909 | CN | H | A2 | J13 | — |
| 910 | CN | H | A2 | J14 | — |
| 911 | CN | H | A2 | J15 | — |
| 912 | CN | H | A2 | J16 | — |
| 913 | CN | H | A2 | J17 | — |
| 914 | CN | H | A2 | J18 | — |
| 915 | CN | H | A2 | J19 | — |
| 916 | CN | H | A2 | J20 | — |
| 917 | CN | H | A2 | J21 | — |
| 918 | CN | H | A2 | J22 | — |
| 919 | CN | H | A2 | J23 | — |
| 920 | CN | H | A2 | J24 | — |
| 921 | CN | H | A3 | J25 | — |
| 922 | CN | H | A2 | J26 | — |
| 923 | CN | H | A2 | J27 | — |
| 924 | CN | H | A2 | J28 | — |
| 925 | CN | H | A2 | J29 | — |
| 926 | CN | H | A2 | J30 | — |
| 927 | CN | H | A2 | J31 | — |
| 928 | CN | H | A2 | J32 | — |
| 929 | CN | H | A3 | J1 | — |
| 930 | CN | H | A3 | J2 | — |
| 931 | CN | H | A3 | J3 | — |
| 932 | CN | H | A3 | J4 | — |
| 933 | CN | H | A3 | J5 | — |
| 934 | CN | H | A3 | J6 | — |
| 935 | CN | H | A3 | J7 | — |
| 936 | CN | H | A3 | J8 | — |
| 937 | CN | H | A3 | J9 | — |
| 938 | CN | H | A3 | J10 | — |
| 939 | CN | H | A3 | J11 | — |
| 940 | CN | H | A3 | J12 | — |
| 941 | CN | H | A3 | J13 | — |
| 942 | CN | H | A3 | J14 | — |
| 943 | CN | H | A3 | J15 | — |
| 944 | CN | H | A3 | J16 | — |
| 945 | CN | H | A3 | J17 | — |
| 946 | CN | H | A3 | J18 | — |
| 947 | CN | H | A3 | J19 | — |
| 948 | CN | H | A3 | J20 | — |
| 949 | CN | H | A3 | J21 | — |
| 950 | CN | H | A3 | J22 | — |
| 951 | CN | H | A3 | J23 | — |
| 952 | CN | H | A3 | J24 | — |
| 953 | CN | H | A3 | J25 | — |
| 954 | CN | H | A3 | J26 | — |
| 955 | CN | H | A3 | J27 | — |
| 956 | CN | H | A3 | J28 | — |
| 957 | CN | H | A3 | J29 | — |
| 958 | CN | H | A3 | J30 | — |
| 959 | CN | H | A3 | J31 | — |
| 960 | CN | H | A3 | J32 | — |
| 961 | Me | Me | A1 | J1 | — |
| 962 | Me | Me | A1 | J2 | — |
| 963 | Me | Me | A1 | J3 | — |
| 964 | Me | Me | A1 | J4 | — |
| 965 | Me | Me | A1 | J5 | — |
| 966 | Me | Me | A1 | J6 | — |
| 967 | Me | Me | A1 | J7 | — |
| 968 | Me | Me | A1 | J8 | — |
| 969 | Me | Me | A1 | J9 | — |
| 970 | Me | Me | A1 | J10 | — |
| 971 | Me | Me | A1 | J11 | — |
| 972 | Me | Me | A1 | J12 | — |
| 973 | Me | Me | A1 | J13 | — |
| 974 | Me | Me | A1 | J14 | — |
| 975 | Me | Me | A1 | J15 | — |
| 976 | Me | Me | A1 | J16 | — |
| 977 | Me | Me | A1 | J17 | — |
| 978 | Me | Me | A1 | J18 | — |
| 979 | Me | Me | A1 | J19 | — |
| 980 | Me | Me | A1 | J20 | — |
| 981 | Me | Me | A1 | J21 | — |
| 982 | Me | Me | A1 | J22 | — |
| 983 | Me | Me | A1 | J23 | — |
| 984 | Me | Me | A1 | J24 | — |
| 985 | Me | Me | A1 | J25 | — |

-continued

| | | | | | |
|---|---|---|---|---|---|
| 986 | Me | Me | A1 | J26 | — |
| 987 | Me | Me | A1 | J27 | — |
| 988 | Me | Me | A1 | J28 | — |
| 989 | Me | Me | A1 | J29 | — |
| 990 | Me | Me | A1 | J30 | — |
| 991 | Me | Me | A1 | J31 | — |
| 992 | Me | Me | A1 | J32 | — |
| 993 | Me | Me | A2 | J1 | — |
| 994 | Me | Me | A2 | J2 | — |
| 995 | Me | Me | A2 | J3 | — |
| 996 | Me | Me | A2 | J4 | — |
| 997 | Me | Me | A2 | J5 | — |
| 998 | Me | Me | A2 | J6 | — |
| 999 | Me | Me | A2 | J7 | — |
| 1000 | Me | Me | A2 | J8 | — |
| 1001 | Me | Me | A2 | J9 | — |
| 1002 | Me | Me | A2 | J10 | — |
| 1003 | Me | Me | A2 | J11 | — |
| 1004 | Me | Me | A2 | J12 | — |
| 1005 | Me | Me | A2 | J13 | — |
| 1006 | Me | Me | A2 | J14 | — |
| 1007 | Me | Me | A2 | J15 | — |
| 1008 | Me | Me | A2 | J16 | — |
| 1009 | Me | Me | A2 | J17 | — |
| 1010 | Me | Me | A2 | J18 | — |
| 1011 | Me | Me | A2 | J19 | — |
| 1012 | Me | Me | A2 | J20 | — |
| 1013 | Me | Me | A2 | J21 | — |
| 1014 | Me | Me | A2 | J22 | — |
| 1015 | Me | Me | A2 | J23 | — |
| 1016 | Me | Me | A2 | J24 | — |
| 1017 | Me | Me | A3 | J25 | — |
| 1018 | Me | Me | A2 | J26 | — |
| 1019 | Me | Me | A2 | J27 | — |
| 1020 | Me | Me | A2 | J28 | — |
| 1021 | Me | Me | A2 | J29 | — |
| 1022 | Me | Me | A2 | J30 | — |
| 1023 | Me | Me | A2 | J31 | — |
| 1024 | Me | Me | A2 | J32 | — |
| 1025 | Me | Me | A3 | J1 | — |
| 1026 | Me | Me | A3 | J2 | — |
| 1027 | Me | Me | A3 | J3 | — |
| 1028 | Me | Me | A3 | J4 | — |
| 1029 | Me | Me | A3 | J5 | — |
| 1030 | Me | Me | A3 | J6 | — |
| 1031 | Me | Me | A3 | J7 | — |
| 1032 | Me | Me | A3 | J8 | — |
| 1033 | Me | Me | A3 | J9 | — |
| 1034 | Me | Me | A3 | J10 | — |
| 1035 | Me | Me | A3 | J11 | — |
| 1036 | Me | Me | A3 | J12 | — |
| 1037 | Me | Me | A3 | J13 | — |
| 1038 | Me | Me | A3 | J14 | — |
| 1039 | Me | Me | A3 | J15 | — |
| 1040 | Me | Me | A3 | J16 | — |
| 1041 | Me | Me | A3 | J17 | — |
| 1042 | Me | Me | A3 | J18 | — |
| 1043 | Me | Me | A3 | J19 | — |
| 1044 | Me | Me | A3 | J20 | — |
| 1045 | Me | Me | A3 | J21 | — |
| 1046 | Me | Me | A3 | J22 | — |
| 1047 | Me | Me | A3 | J23 | — |
| 1048 | Me | Me | A3 | J24 | — |
| 1049 | Me | Me | A3 | J25 | — |
| 1050 | Me | Me | A3 | J26 | — |
| 1051 | Me | Me | A3 | J27 | — |
| 1052 | Me | Me | A3 | J28 | — |
| 1053 | Me | Me | A3 | J29 | — |
| 1054 | Me | Me | A3 | J30 | — |
| 1055 | Me | Me | A3 | J31 | — |
| 1056 | Me | Me | A3 | J32 | — |
| 1057 | H | MeO | A1 | J1 | S |
| 1058 | H | MeO | A1 | J2 | S |
| 1059 | H | MeO | A1 | J3 | S |
| 1060 | H | MeO | A1 | J4 | S |
| 1061 | H | MeO | A1 | J5 | S |
| 1062 | H | MeO | A1 | J6 | S |
| 1063 | H | MeO | A1 | J7 | S |
| 1064 | H | MeO | A1 | J8 | S |

-continued

| | | | | | |
|---|---|---|---|---|---|
| 1065 | H | MeO | A1 | J9 | S |
| 1066 | H | MeO | A1 | J10 | S |
| 1067 | H | MeO | A1 | J11 | S |
| 1068 | H | MeO | A1 | J12 | S |
| 1069 | H | MeO | A1 | J13 | S |
| 1070 | H | MeO | A1 | J14 | S |
| 1071 | H | MeO | A1 | J15 | S |
| 1072 | H | MeO | A1 | J16 | S |
| 1073 | H | MeO | A1 | J17 | S |
| 1074 | H | MeO | A1 | J18 | S |
| 1075 | H | MeO | A1 | J19 | S |
| 1076 | H | MeO | A1 | J20 | S |
| 1077 | H | MeO | A1 | J21 | S |
| 1078 | H | MeO | A1 | J22 | S |
| 1079 | H | MeO | A1 | J23 | S |
| 1080 | H | MeO | A1 | J24 | S |
| 1081 | H | MeO | A1 | J25 | S |
| 1082 | H | NeO | A1 | J26 | S |
| 1083 | H | MeO | A1 | J27 | S |
| 1084 | H | MeO | A1 | J28 | S |
| 1085 | H | MeO | A1 | J29 | S |
| 1086 | H | MeO | A1 | J30 | S |
| 1087 | H | MeO | A1 | J31 | S |
| 1088 | H | MeO | A1 | J32 | S |
| 1089 | H | MeO | A2 | J1 | S |
| 1090 | H | MeO | A2 | J2 | S |
| 1091 | H | MeO | A2 | J3 | S |
| 1092 | H | MeO | A2 | J4 | S |
| 1093 | H | MeO | A2 | J5 | S |
| 1094 | H | MeO | A2 | J6 | S |
| 1095 | H | MeO | A2 | J7 | S |
| 1096 | H | MeO | A2 | J8 | S |
| 1097 | H | MeO | A2 | J9 | S |
| 1098 | H | MeO | A2 | J10 | S |
| 1099 | H | MeO | A2 | J11 | S |
| 1100 | H | MeO | A2 | J12 | S |
| 1101 | H | MeO | A2 | J13 | S |
| 1102 | H | MeO | A2 | J14 | S |
| 1103 | H | MeO | A2 | J15 | S |
| 1104 | H | MeO | A2 | J16 | S |
| 1105 | H | MeO | A2 | J17 | S |
| 1106 | H | MeO | A2 | J18 | S |
| 1107 | H | MeO | A2 | J19 | S |
| 1108 | H | MeO | A2 | J20 | S |
| 1109 | H | MeO | A2 | J21 | S |
| 1110 | H | MeO | A2 | J22 | S |
| 1111 | H | MeO | A2 | J23 | S |
| 1112 | H | MeO | A2 | J24 | S |
| 1113 | H | MeO | A3 | J25 | S |
| 1114 | H | MeO | A2 | J26 | S |
| 1115 | H | MeO | A2 | J27 | S |
| 1116 | H | MeO | A2 | J28 | S |
| 1117 | H | MeO | A2 | J29 | S |
| 1118 | H | MeO | A2 | J30 | S |
| 1119 | H | MeO | A2 | J31 | S |
| 1120 | H | MeO | A2 | J32 | S |
| 1121 | H | MeO | A3 | J1 | S |
| 1122 | H | MeO | A3 | J2 | S |
| 1123 | H | MeO | A3 | J3 | S |
| 1124 | H | MeO | A3 | J4 | S |
| 1125 | H | MeO | A3 | J5 | S |
| 1126 | H | MeO | A3 | J6 | S |
| 1127 | H | MeO | A3 | J7 | S |
| 1128 | H | MeO | A3 | J8 | S |
| 1129 | H | MeO | A3 | J9 | S |
| 1130 | H | MeO | A3 | J10 | S |
| 1131 | H | MeO | A3 | J11 | S |
| 1132 | H | MeO | A3 | J12 | S |
| 1133 | H | MeO | A3 | J13 | S |
| 1134 | H | MeO | A3 | J14 | S |
| 1135 | H | MeO | A3 | J15 | S |
| 1136 | H | MeO | A3 | J16 | S |
| 1137 | H | MeO | A3 | J17 | S |
| 1138 | H | MeO | A3 | J18 | S |
| 1139 | H | MeO | A3 | J19 | S |
| 1140 | H | MeO | A3 | J20 | S |
| 1141 | H | MeO | A3 | J21 | S |
| 1142 | H | MeO | A3 | J22 | S |
| 1143 | H | MeO | A3 | J23 | S |

| | | | | | |
|---|---|---|---|---|---|
| 1144 | H | MeO | A3 | J24 | S |
| 1145 | H | MeO | A3 | J25 | S |
| 1146 | H | MeO | A3 | J26 | S |
| 1147 | H | MeO | A3 | J27 | S |
| 1148 | H | MeO | A3 | J28 | S |
| 1149 | H | MeO | A3 | J29 | S |
| 1150 | H | MeO | A3 | J30 | S |
| 1151 | H | MeO | A3 | J31 | S |
| 1152 | H | MeO | A3 | J32 | S |

The benzimidazole derivative (1) of the present invention can be produced by synthesis method (A) or synthesis method (B) shown below in the case E is $COOR^3$ and M is S:

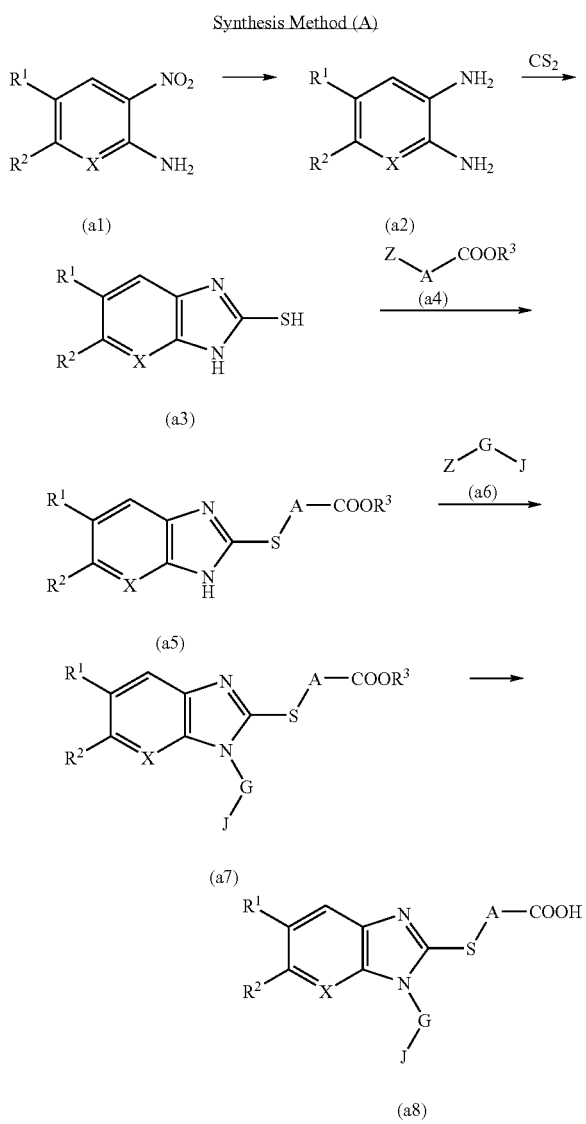

wherein, Z represents a halogen or ammonium group, and $R^1$, $R^2$, $R^3$, A, G, J and X are as defined above.

Namely, an orthophenylenediamine compound (a2) is obtained by reducing the nitro group of a 2-nitroaniline derivative (a1). After reacting this with $CS_2$ and obtaining compound (a3), it is reacted with a halide ester derivative (a4) to obtain (a5) followed by further reacting with a halide derivative or ammonium salt (a6) to be able to obtain the compound (a7) of the present invention. In addition, benzimidazole derivative (a8), in which $R^3$ is a hydrogen atom, can be obtained by hydrolyzing this as necessary.

Reduction of the nitro group can be carried out, in accordance with the conditions of an ordinary catalytic reduction, by reacting with hydrogen gas at a temperature of room temperature to 100° C. in the presence of a catalyst such as Pd—C under acidic, neutral or alkaline conditions. In addition, this can also be carried out by a method in which treatment is carried out using zinc or tin under acidic conditions, or by a method that uses zinc powder under neutral or alkaline conditions.

The reaction between orthophenylenediamine derivative (a2) and $CS_2$ can be carried out according to the method described in, for example, The Journal of Organic Chemistry (J. Org. Chem.), 1954, Vol. 19, pages 631–637 (pyridine solution) or in The Journal of Medical Chemistry (J. Med. Chem.), 1993, Vol. 36, pages 1175–1187 (ethanol solution).

The reaction between thiobenzimidazole compound (a3) and halide ester (a4) can be carried out by agitating at a temperature of 0° C.–200° C. in the presence of a base such as NaH, $Et_3N$, NaOH or $K_2CO_3$ in accordance with the conditions of an ordinary S-alkylation reaction.

The reaction between thiobenzimidazole compound (a5) and halide derivative or ammonium salt (a6) can be carried out by agitating at a temperature of 0° C.–200° C. in the presence of a base such as NaH, $Et_3N$, NaOH, $K_2CO_3$ or $Cs_2CO_3$ in accordance with the conditions of an ordinary N-alkylation or N-acylation reaction.

A hydrolysis method using an alkali such as lithium hydroxide or an acid such as hydrochloric acid or trifluoroacetic acid is preferably used for the elimination reaction of the carboxy protecting group $R^3$.

Synthesis Method (B)

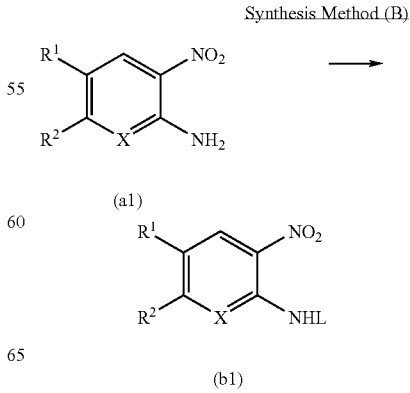

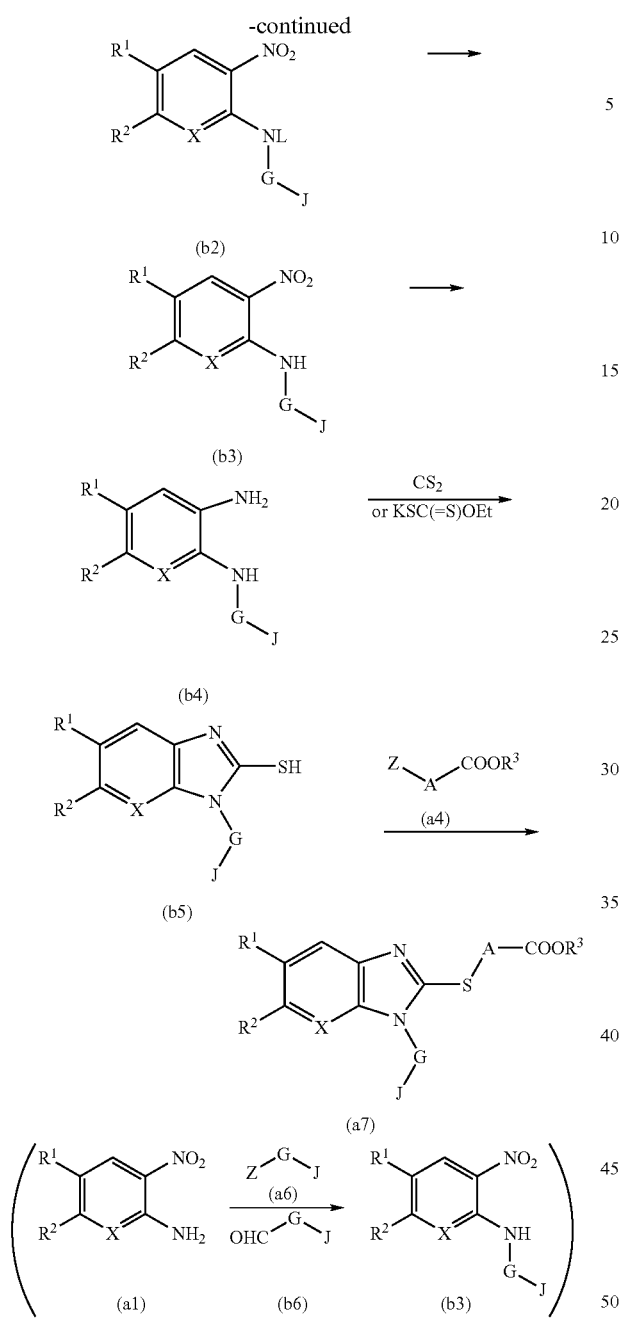

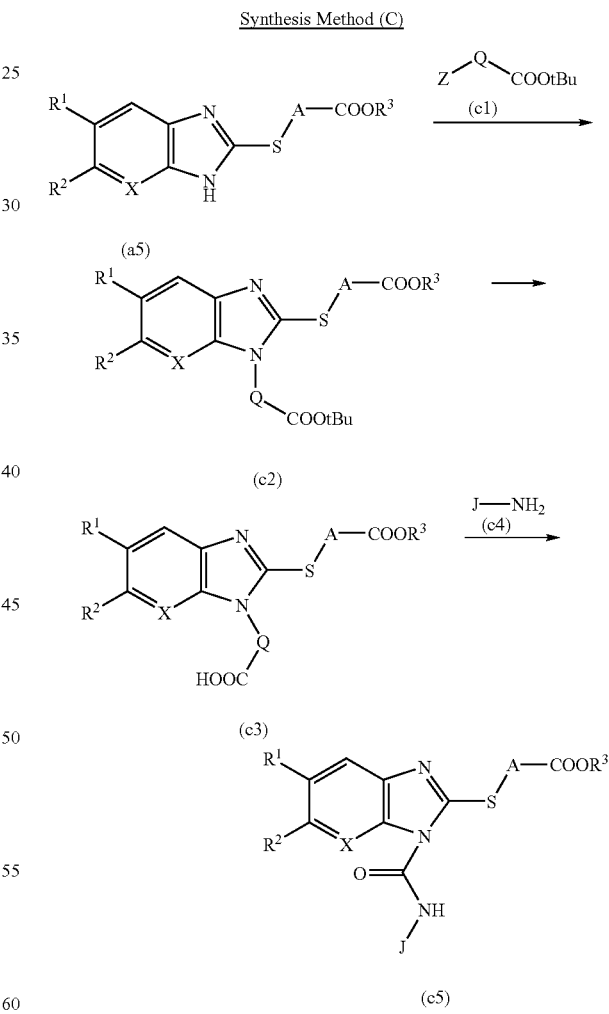

aldehyde derivative (b6) with the 2-nitroaniline derivative (a1). Examples of protecting group L include a trifluoroacetyl group, acetyl group, t-butoxycarbonyl group and benzyl group. The reaction between the 2-nitroaniline derivative (a1) and aldehyde derivative (b6) can be carried out by an ordinary reduction amination under temperature conditions of 0° C.–200° C. in a solvent such as ethanol, methanol or dichloromethane using a multiple hydrogen compound such as $LiAlH_4$, $NaBH_4$, $NaBH_3CN$ or NABH$(OAc)_3$ or a reducing agent such as diborane. In addition, the reaction between the orthophenylenediamine derivative (b4) and $CS_2$ can be carried out in the same manner as Synthesis Method (A), while the reaction with KSC(=S)Oet can be carried out according to the method described in, for example, Organic Synthesis (OS), 1963, Vol. 4, pages 569–570. Other reactions can be carried out in the same manner as Synthesis Method (A).

Benzimidazole derivative (1) of the present invention can be produced according to the following Synthesis Method (C) in the case E is $COOR^3$, M is S and G is an amide bond:

Namely, (b1) is obtained by protecting the amino group of 2-nitroaniline derivative (a1) with a suitable protecting group L. This is then reacted with a halide derivative or ammonium salt (a6) to obtain (b2), and (b3) is obtained by removing protecting group L. An orthophenylenediamine derivative (b4) is obtained by reducing the nitro group of (b3). After reacting this with $CS_2$ or KSC(=S)Oet and obtaining compound (b5), this is reacted with a halide ester derivative (a4) to be able to obtain the benzimidazole derivative (a7) of the present invention. In addition, this may then be hydrolyzed as necessary to obtain a benzimidazole derivative of the present invention in which $R^3$ is a hydrogen atom.

Compound (b3) can also be obtained directly by reacting an unprotected halide derivative, ammonium salt (a6) or aldehyde derivative (b6) with the 2-nitroaniline derivative (a1).

wherein, Q represents a methylene group, phenylene group, etc., Z represents a halogen, and $R^1$, $R^2$, $R^3$, A, J and X are as defined above, provided that $R^3$ is an inactive protecting group such as a methyl group or ethyl group under acidic conditions.

Namely, compound (c2) is obtained by reacting thiobenzimidazole compound (a5) with tert-butylesterhalide derivative (c1). This is then hydrolyzed under acidic conditions to obtain (c3). This is then condensed with amine derivative (c4) to be able to obtain compound (c5) of the present invention. In addition, this may be hydrolyzed as necessary to obtain the benzimidazole derivative of the present invention in which $R^3$ is a hydrogen atom.

A typical method using a condensation agent is used for the conditions of condensation amidation. Examples of condensation agents include DCC, DIPC, EDC=WSCI, WSCI.HCl, BOP and DPPA, and these may be used alone or as a combination with HONSu, HOBt or HOOBt. The reaction is carried out under temperature conditions of 0° C.–200° C. in a suitable solvent such as THF, chloroform or t-butanol. The other reactions can be carried out in the same manner as Synthesis Method (A).

The benzimidazole derivative (1) of the present invention can be produced according to the following Synthesis Method (D) in the case E is $COOR^3$, M is S and G has an ether bond:

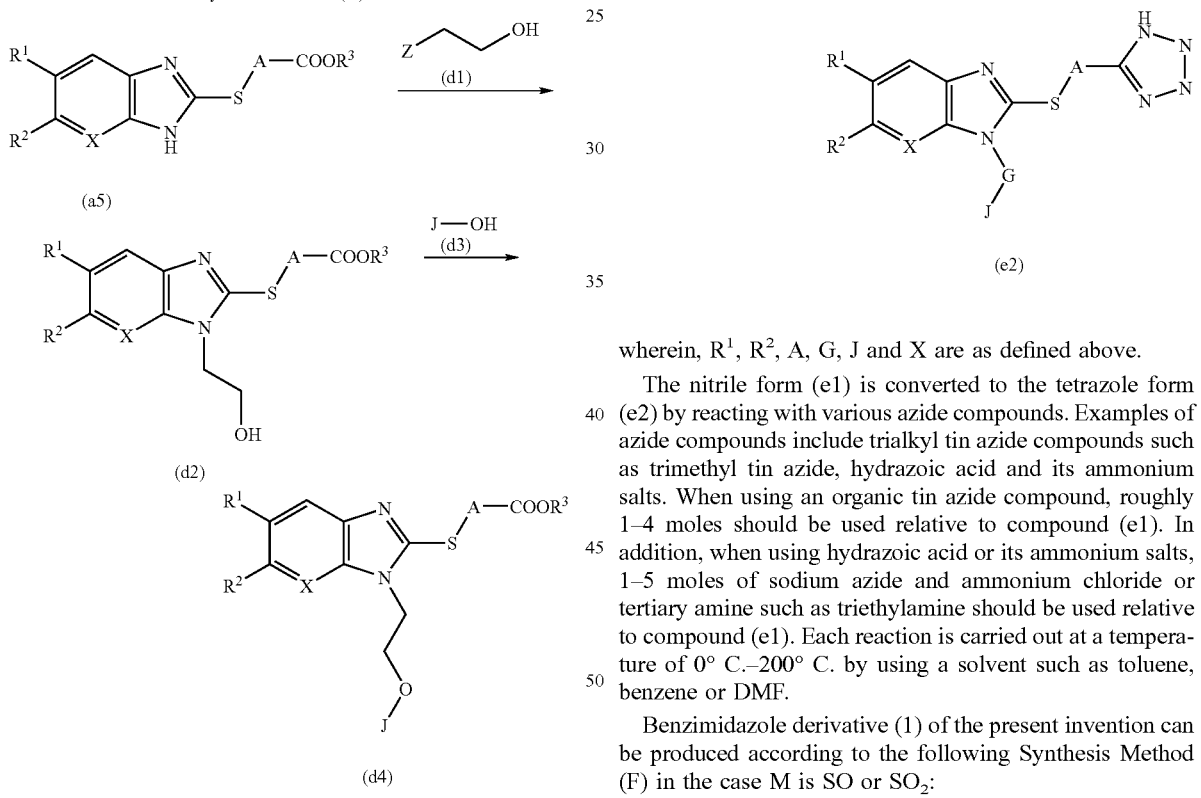

wherein, Z represents a halogen and $R^1$, $R^2$, $R^3$, A, J and X are as defined above.

Namely, compound (d2) is obtained by reacting, for example, halide alcohol derivative (d1) with thiobenzimidazole compound (a5). This is then reacted with phenol derivative (d3) to be able to obtain compound (d4) of the present invention. In addition, this may be hydrolyzed as necessary to obtain a benzimidazole derivative in which $R^3$ is a hydrogen atom.

The etherification reaction is carried out by Mitsunobu reaction and similar reactions under temperature conditions of 0° C.–200° C. in a suitable solvent such as N-methylmorpholine or THF using a phosphine compound such as triphenylphosphine or tributylphosphine and an azo compound such as DEAD or TMAD. The other reactions can be carried out in the same manner as Synthesis Method (A).

Benzimidazole derivative (1) of the present invention can be produced according to the following Synthesis Method (E) in the case E is tetrazole-5-yl and M is S:

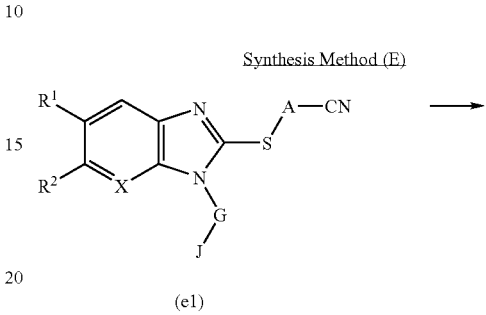

wherein, $R^1$, $R^2$, A, G, J and X are as defined above.

The nitrile form (e1) is converted to the tetrazole form (e2) by reacting with various azide compounds. Examples of azide compounds include trialkyl tin azide compounds such as trimethyl tin azide, hydrazoic acid and its ammonium salts. When using an organic tin azide compound, roughly 1–4 moles should be used relative to compound (e1). In addition, when using hydrazoic acid or its ammonium salts, 1–5 moles of sodium azide and ammonium chloride or tertiary amine such as triethylamine should be used relative to compound (e1). Each reaction is carried out at a temperature of 0° C.–200° C. by using a solvent such as toluene, benzene or DMF.

Benzimidazole derivative (1) of the present invention can be produced according to the following Synthesis Method (F) in the case M is SO or $SO_2$:

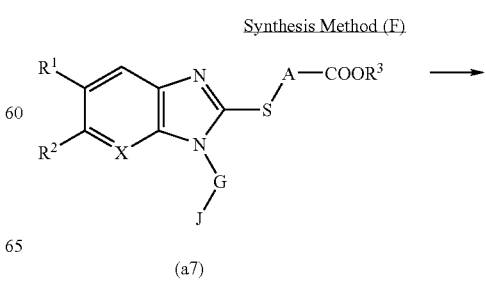

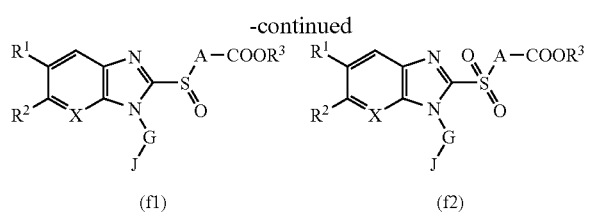

(f1)  (f2)

wherein, $R^1$, $R^2$, $R^3$, A, G, J and X are as defined above.

Namely, sulfoxide derivative (a7) and/or sulfone derivative (f2) are obtained by reacting benzimidazole derivative (a7) with a peroxide compound in a suitable solvent. Examples of peroxide compounds used include perbenzoic acid, m-chloroperbenzoic acid, peracetic acid and hydrogen peroxide, while examples of solvents used include chloroform and dichloromethane. There are no particular restrictions on the usage ratio of compound (a7) and a peroxide compound, and although the ratio should be suitably selected over a wide range, it is generally preferable to use about 1.2 to 5 moles. Each reaction is normally carried out at 0–50° C., and preferably from 0° C. to room temperature, and each reaction is typically completed in about 4–20 hours.

Benzimidazole derivative (1) of the present invention can be produced according to the following Synthesis Method (G) in the case M is a single bond:

Synthesis Method (G)

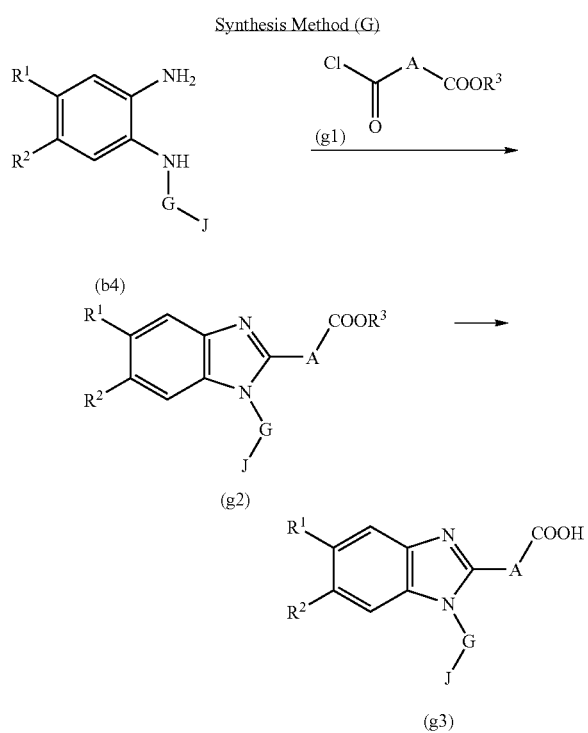

wherein, X, A, G, J and $R^3$ are as defined above.

Namely, benzimidazole derivative (g2) of the present invention can be obtained by reacting a known acid chloride derivative (g1) with a diamine compound (b4). In addition, hydrolyzing —$COOR^3$ of (g2) as necessary allows the obtaining of benzimidazole derivative (g3) in which $R^3$ is a hydrogen atom.

Furthermore, the cyclization reaction is described in the Journal of Medical Chemistry (J. Med. Chem.), 1993, Vol. 36, pages 1175–1187.

In addition, Z-G-J described in synthesis methods (A) through (F) can be synthesized by referring to a large number of publications.

For example, a benzothiophene halide derivative can be synthesized by referring to the following literature and patent specification.

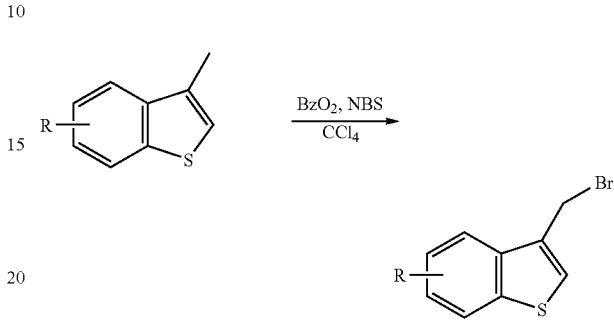

J. Chem. Soc. (1965), 774
J. Chem. Soc. Perkin Trans 1, (1972), 3011

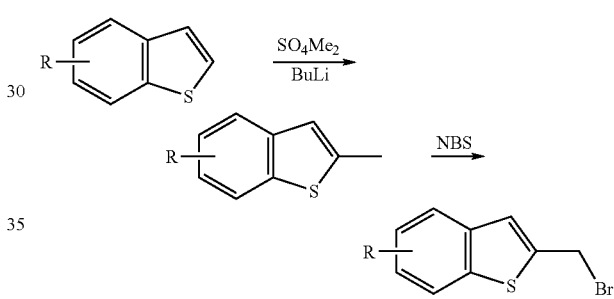

JACS, 74, 664, (1951); U.S. Pat. No. 4,282,227

These compounds can also be synthesized by referring to the following literature and patent specifications. Namely, these compounds can be synthesized not only by the reactions described in the following literature, but also by combining typical reactions such as oxidation-reduction or OH halogenation.

J Chem Soc, (1965), 774; Bull Chem Soc Jpn (1968), 41, 2215; Japanese Unexamined Patent Publication No. 10-298180; Sulfur Reports, (1999), Vol. 22, 1–47; J Chem Soc comm., (1988), 888: J. Heterocyclic Chem., 19, 859, (1982); Synthetic Communication, (1991), 21, 959; Tetrahedron Letters, (1992), Vol. 33, No. 49, 7499; Synthetic Communications, (1993), 23(6), 743; Japanese Unexamined Patent Publication No. 2000-239270; J. Med. Chem., (1985), 28, 1896; Arch Pharm, (1975), 308, 7, 513; Khim Gerotsikl Soedin, (1973), 8, 1026; Bull. Chem. Soc. Jpn., (1997), 70, 891; J. Chem. Soc. Perkin1, (1973), 750; J. Chem. Soc. Chem. Comm., (1974), 849; J. Chem. Soc. Comm. (1972), 83

In particular, the hydroxymethyl form at position 3 of benzothiophene can be synthesized easily by referring to J. Chem. Soc. Chem. Comm., (1974), 849.

With respect to iodides, the Cl and Br forms can be obtained by halogen exchange with NaI and so forth.

In addition, the quaternary ammonium salt derivative of benzothiophene can be synthesized by reacting a suitable amine such as dimethylamine with the previously mentioned benzothiophene halide derivative. In addition, it may also be synthesized in the following manner:

Synthesis Method (H)

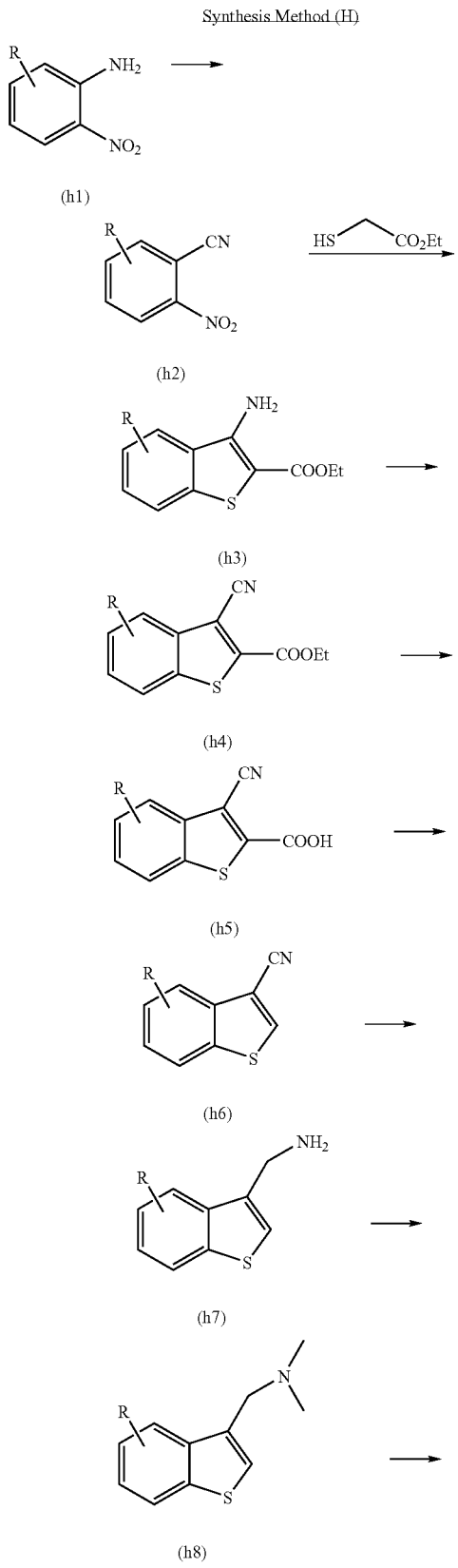

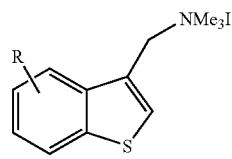

(h9)

wherein, R represents one or more substituents in the above-mentioned J, the number of substituents is optional, and the substituents may be independent substituents.

Namely, cyclic benzothiophene derivative (h3) is obtained by converting the amino group of 2-nitroaniline derivative (h1) to a cyano form (h2) and reacting with ethyl 2-mercaptoacetate. Moreover, carboxylic acid (h5) is obtained by cyanating the amino group to a cyano form (h4) followed by ester hydrolysis. The carboxylic acid is then decarboxylated to obtain (h6). Continuing, the cyano group is reduced to convert to an amino form (h7) followed by N-dimethylation to obtain (h8) and then followed by N-methylation to be able to obtain quaternary salt (h9).

Cyanation of the amino group of 2-nitroaniline derivative (h1) by converting the amino group to diazonium using, for example, hydrochloric acid or sodium sulfite, and then further reacting with copper (I) chloride and potassium cyanide to convert to the cyano form.

Reaction from cyano form (h2) to benzothiophene derivative (h3) can be carried out to obtain cyclic benzothiophene derivative (h3) by heating with ethyl 2-mercaptoacetate in a suitable solvent such as DMF in the presence of a suitable basic reagent by referring to the method described in, for example, Synthetic Communications, 23(6), 743–748 (1993); or Farmaco, Ed. Sci., 43, 1165 (1988).

With respect to the cyanation of (h3), (h3) can be converted to the cyano form (h4) by reacting copper cyanide and t-butyl sulfite in a suitable solvent such as DMSO under suitable temperature conditions.

Ester hydrolysis can be carried out by routinely used methods. For example, carboxylic acid (h5) can be obtained by ester hydrolysis in a suitable solvent such as THF-MeOH in the presence of a suitable basic reagent such as sodium hydroxide.

The carboxylic acid decarboxylation reaction can be carried out by heating in a suitable solvent such as quinoline solvent in the presence of a copper catalyst.

Reduction of the cyano group to an amino group can be carried out to obtain the amino form by, for example, reducing in a suitable solvent such as $Et_2O$-THF under suitable temperature conditions using a suitable reducing agent such as lithium aluminum hydride.

Methylation of the amino group can be carried out by heating in, for example, formic acid or aqueous formalin solution.

Conversion of the amino group to a quaternary salt can be carried out by, for example, reacting with methyl iodide in ethanol solvent.

Indole quaternary amine salt derivative can be synthesized according to, for example, the following method:

Synthesis Method (K)

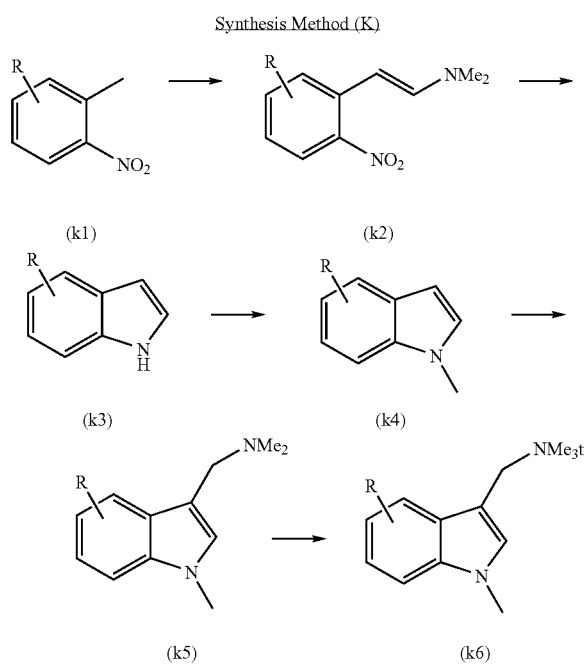

wherein, R represents one or more substituents in the above-mentioned J, the number of substituents is optional, and the substituents may be independent substituents.

Namely, nitro form (k1) is converted to an enamine (k2) by enanimation followed by converting to the indole form (k3) by indole cyclization according to the method of Reissert. Moreover, the $3^{rd}$ position dimethylaminomethyl form (k5) is obtained according to the Mannich reaction following N-dimethylation and this is followed by N-methylation to be able to obtain the quaternary amine salt (k6).

The enamination reaction can be carried out by, for example, heating the O-nitrotoluene derivative (k1) with N,N-dimethylformamide dimethylacetal and pyrrolidine in a suitable solvent such as DMF.

The indole cyclization reaction can be carried out by reacting at room temperature using hydrogen gas in the presence of Raney nickel in a suitable solvent such as toluene.

N-methylation can be carried out by, for example, heating in DMF solvent using t-butoxypotassium or dimethyl oxalate.

$3^{rd}$ position dimethylaminomethylation can be carried out by, for example, using the Mannich reaction and reacting at room temperature in dioxane-acetic acid solvent using aqueous formalin solution or aqueous dimethylamine solution.

In addition, the indole derivative can be synthesized by referring to the literature of Heterocycles, Vol. 22, No. 1, 195, (1984).

Moreover, benzothiophene, indole and other heterocyclic halides and quaternary salts can be synthesized by referring to other references in the literature such as Heterocyclic Compound Chemistry, (Kondansha Scientific, H. Yamanaka, ed.).

Benzimidazole derivative of the present invention can also be converted to a medically acceptable, non-toxic salt as necessary. Examples of such salts include salt of alkali metal ions such as $Na^+$ and $K^+$, alkaline earth metal ions such as $Mg^{2+}$ and $Ca^{2+}$ and metal ions such as $Al^{3+}$ and $Zn^{2+}$, as well as salt of organic bases such as ammonia, triethylamine, ethylenediamine, propanediamine, pyrrolidine, piperidine, piperazine, pyridine, lysine, choline, ethanolamine, N,N-dimethylethanolamine, 4-hydroxypiperidine, glucosamine and N-methylglucamine. In particular, $Na^+$, $K^+$, $Ca^{2+}$, lysine, choline, N,N-dimethylethanolamine and N-methylglucamine are preferable.

Benzimidazole derivative of the present invention strongly inhibits human chymase activity. More specifically, $IC_{50}$ is 1000 nM or less, preferably 0.01 nM or more to less than 1000 nM, and more preferably 0.05 nM or more to less than 500 nM. The benzimidazole derivative of the present invention having such superior human chymase inhibitory activity can be used as a preventive agent and/or therapeutic agent clinically applicable to various diseases.

Benzimidazole derivative of the present invention can be administered orally or non-orally as a pharmaceutical composition together with a pharmaceutically allowed carrier by forming said pharmaceutical composition into various drug forms. Examples of non-oral administration include intravenous, subcutaneous, intramuscular, transcutaneous, rectal, nasal and intraocular administration.

Examples of drug forms of said pharmaceutical composition include tablets, pills, granules, powders, liquids, suspensions, syrups and capsules in the case of oral preparations.

Here, for the method of forming tablets, tablets can be formed by an ordinary method using a pharmaceutically acceptable carrier such as a vehicle, binder or disintegration agent. Pills, granules and powders can be formed by an ordinary method using a vehicle and so forth in the same manner as tablets. Liquids, suspensions and syrups can be formed according to an ordinary method using glycerin esters, alcohols, water or vegetable oil. Capsules can be formed by filling granules, powders or liquids and so forth into capsules made of gelatin and so forth.

Non-oral preparations can be administered in the form of an injection preparation in the case of administration by intravenous, subcutaneous or intramuscular administration. Examples of injection preparations include the case in which a benzimidazole derivative of the present invention is dissolved in a water-soluble liquid agent such as physiological saline, or the case in which it is dissolved in a non-aqueous liquid agent composed of an organic ester such as vegetable oil.

In the case of percutaneous administration, a drug form such as an ointment or cream can be used. Ointments can be formed by mixing a benzimidazole derivative of the present invention with an oil or Vaseline and so forth, while creams can be formed by mixing a benzimidazole derivative of the present invention with an emulsifier.

In the case of rectal administration, administration can be performed in the form of a suppository using gelatin soft capsules and so forth.

In the case of nasal administration, a preparation can be used that is composed of a liquid or powder composition. Examples of bases of liquid preparations that are used include water, saline, phosphate buffer and acetate buffer, and may also contain surfactant, antioxidant, stabilizer, preservative or thickener. Examples of bases of powdered preparations include moisture absorbing bases such as water-soluble polyacrylates, cellulose lower alkyl ethers, polyethylene glycol polyvinyl pyrrolidone, amylose and plurane, or water-insoluble bases such as celluloses, starches, proteins, rubbers and cross-linked vinyl polymers, although water-soluble bases are preferable. In addition, these may also be used as a mixture. Moreover, antioxidant, colorant, preservative, antiseptic or polysaprobic agent may be added to powdered preparations. Said liquid preparations and powdered preparations can be administered using a sprayer and so forth.

In the case of intraocular administration, an aqueous or non-aqueous eye wash can be used. Aqueous eye washes can use sterile purified water or physiological saline for the solvent. In the case of using only sterile purified water for the solvent, it can be used in the form of an aqueous suspended eye wash by adding surfactant, polymer thickener and so forth. In addition, it can also be used in the form of a soluble eye wash by adding a solubilization agent such as non-ionic surfactant. Non-aqueous eye washes can use a non-aqueous solvent for injection for the solvent, and can also be used in the form of a non-aqueous suspended eye wash.

Examples of drug forms used in the case of administration to the eye other than as an eye wash include ophthalmic ointments, applied liquids, sprays and inserts.

In addition, in the case of inhaling through the nose or mouth, benzimidazole derivative of the present invention is inhaled using, for example, an aerosol spray for inhalation by combining with a typically used pharmaceutical vehicle in the form of a solution or suspension. In addition, benzimidazole derivative of the present invention can be administered in the form of a dry powder using an inhaler in direct contact with the lungs.

Pharmaceutically allowed carriers such as isotonic agents, preservatives, antiseptics, moisturizers, buffers, emulsifiers, dispersants and stabilizers can be added to these various preparations as necessary.

In addition, these various preparations can be sterilized by performing treatment such as blending with a disinfectant, filtering using a bacteria-trapping filter, heating or irradiating as necessary. Alternatively, a sterile solid preparation can be produced and used after dissolving or suspending in a suitable sterile liquid immediately prior to use.

Although the dosage of benzimidazole derivative of the present invention varies according to the type of disease, administration route and symptoms, age, sex and body weight, etc. of the patient, it is typically 1–500 mg/day/person, and preferably 10–300 mg/day/person, in the case of oral administration, and 0.1–100 mg/day/person, and preferably 0.3–30 mg/day/person, in non-oral administration such as intravenous, subcutaneous, intramuscular, percutaneous, rectal, nasal, intraocular or inhalation administration.

In addition, in the case of using benzimidazole derivative of the present invention as a preventive agent, it can be administered in accordance with previously known methods according to each symptom.

Examples of target diseases of the preventive agent and/or therapeutic agent of the present invention include respiratory diseases such as bronchial asthma, inflammatory and allergic diseases such as allergic rhinitis, atopic dermatitis and urticaria, cardiovascular diseases such as sclerosing vascular lesions, vasoconstriction, peripheral circulatory disorders, renal insufficiency and cardiac insufficiency, and bone and cartilage metabolic diseases such as rheumatoid arthritis and osteoarthritis.

EXAMPLES

The following provides a detailed explanation of the present invention according to its production examples, examples and test examples. However, the scope of the present invention is not restricted in any sense by these examples.

Reference Example 1

Production of 5,6-dimethylbenzimidazole-2-thiol

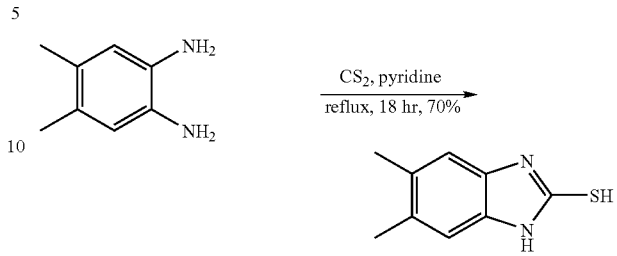

40 ml (0.66 mmol) of carbon disulfide were added to a pyridine solution (40 ml) of 4.5 g (33 mmol) of 5,6-dimethylorthophenylenediamine. After stirring the resulting solution for 18 hours while refluxing under heating, water was added followed by extraction with ethyl acetate. After drying the ethyl acetate phase with anhydrous magnesium sulfate, it was concentrated under reduced pressure and dried for 6 hours at 80° C. under reduced pressure to obtain 4.1 g of the target compound (yield: 70%).

$^1$H-NMR (270 MHz, DMSO-d$^6$) (ppm): 12.30 (br, 1H), 6.91 (s, 2H), 2.21 (s, 6H)

Reference Example 2

Production of 4-(5,6-dimethylbenzimidazole-2-ylthio)butanoate ethyl ester

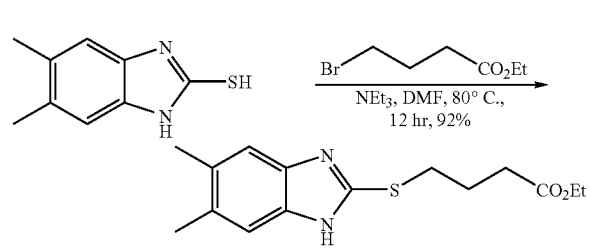

35 µl (0.25 mmol) of triethylamine and 36 µl (0.25 mmol) of 4-bromobutanoate ethyl ester were added to 36 mg (0.20 mmol) of 5,6-dimethylbenzimidazole-2-thiol. After stirring the resulting solution for 12 hours at 80° C., water was added followed by extraction with diethyl ether. After drying the diethyl ether phase with anhydrous magnesium sulfate, it was concentrated and residue was purified by silica gel column chromatography (hexane:ethyl acetate=4:1) to obtain 54 mg of the target compound (yield: 92%). Confirmation of the compound was carried out by identifying it from the molecular weight using LC-MS.

Calculated value M=292.12, Measured value (M+H)$^+$ =293.40

Reference Example 3

The following compounds were synthesized according to the same method as Reference Example 2. Confirmation of the compounds was carried out by identifying them from the molecular weight using LC-MS.

4-(benzimidazole-2-ylthio)butanoate ethyl ester

Calculated value M=264.09, Measured value (M+H)⁺=293.40

4-(5,6-difluorobenzimidazole-2-ylthio)butanoate ethyl ester

Calculated value M=300.07, Measured value (M+H)⁺=301.3

Reference Example 4

Production of 3-bromomethyl-5-methylbenzo[b]thiophene

Step 1

Production of 3-hydroxymethyl-p-nitrotoluene

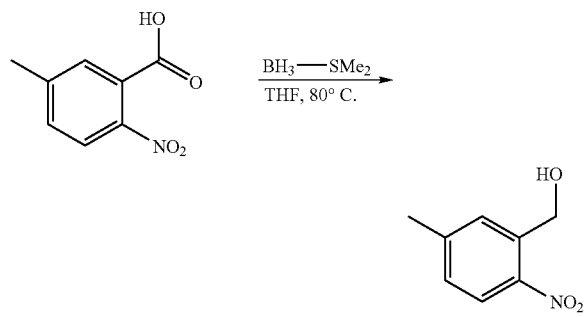

5.02 g (27.7 mmol) of 5-methyl-2-nitrobenzoic acid were dissolved in 20 ml of THF followed by dropping in 11.1 ml of 10.2 M borane dimethylsulfide complex and heating at 80° C. After 1.5 hours, 30 ml of 1 M hydrochloric acid were dropped into this reaction system while cooling with ice and stirring. The system was then concentrated under reduced pressure to obtain 100 ml of the aqueous phase followed by extraction with ethyl acetate (100 ml×2). After washing the ethyl acetate phase with saturated brine, the organic phase was dried with magnesium sulfate followed by concentration under reduced pressure and drying to obtain 3.91 g of the target compound (yield: 85%).

Step 2

Production of 3-formyl-p-nitrotoluene

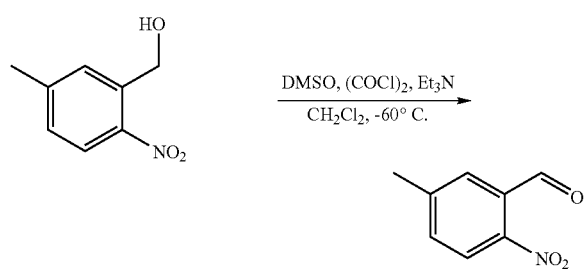

5.5 ml (63.2 mmol) of oxalyl chloride were added to 50 ml of dichloromethane and cooled to −60° C. After 20 minutes, 9.13 ml (138.6 mmol) of DMSO were added and stirred at −60° C. followed 15 minutes later by the addition of 3.91 g (23.3 mmol) of the 3-hydroxymethyl-p-nitrotoluene obtained in Step 1 at −60° C. and stirring. After 30 minutes, 45 ml of triethylamine were dropped in at −60° C. and then returned to room temperature. After concentrating under reduced pressure, 0.1 M hydrochloric acid was added to the residue followed by extraction with ethyl acetate (150 ml×2). The organic phase was then dried with magnesium sulfate and concentrated under reduced pressure to obtain 5.02 g of the target compound (crude yield: 130%).

Step 3

Production of 2-carboxyethyl-5-methylbenzo[b]thiophene

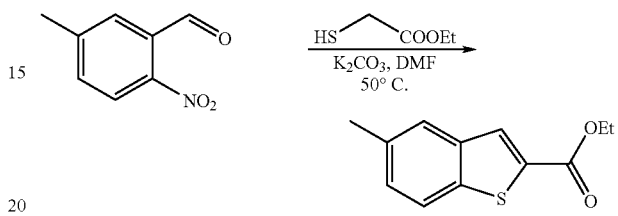

5.02 g (63.2 mmol) of the 3-formyl-p-nitrotoluene obtained in Step 2 were dissolved in 50 ml of DMF followed by the addition of 3.06 ml (28.1 mmol) of ethyl mercaptoacetate and 4.85 g (35.1 mmol) of potassium carbonate and stirring at 50° C. After 9.5 hours, the temperature was raised to 80° C. followed by additional heating for 100 minutes. Following completion of the reaction, 250 ml of water were added to the reaction solution followed by extraction with ethyl acetate (100 ml×3) and drying with magnesium sulfate. After concentrating the solvent under reduced pressure, the residue was purified by silica gel column chromatography (hexane:ethyl acetate=8:1) followed by additionally purifying by silica gel column chromatography (hexane:ethyl acetate=10:1) to obtain 2.48 g (11.2 mmol) of the target compound (yield: 48%).

¹H-NMR (400 MHz, CDCl₃) (ppm): 7.98 (s, 1H), 7.73 (d, 1H, J=8.28 Hz), 7.65 (s, 1H), 7.27 (d, 1H, J=8.32 Hz), 4.39 (q, 2H), 2.47 (s, 3H), 1.41 (s, 3H)

Step 4

Production of 2-carboxy-5-methylbenzo[b]thiophene

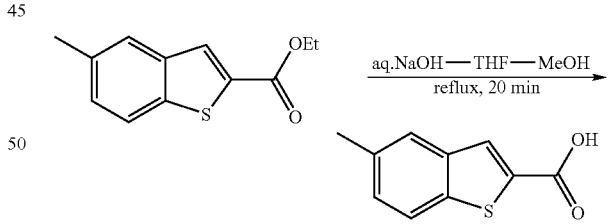

30 ml of a solution of methanol, THF and 2 M aqueous sodium hydroxide solution (1:1:1) were added to 2.17 g (9.87 mmol) of the 2-carboxyethyl-5-methylbenzo[b]thiophene obtained in Step 3 and refluxed. After 20 minutes, the solution was neutralized with acid followed by concentration under reduced pressure and recovery of the precipitate. This was then washed with 50 ml of water and dried to obtain 2.03 g (10.5 mmol) of the target compound (crude yield: 107%).

¹H-NMR (400 MHz, CDCl₃) (ppm): 7.94 (s, 1H), 7.74 (d, 1H, J=8.56 Hz), 7.69 (s, 1H), 7.27 (d, 1H, J=8.30 Hz), 2.47 (s, 3H)

Step 5
Production of 5-methylbenzo[b]thiophene

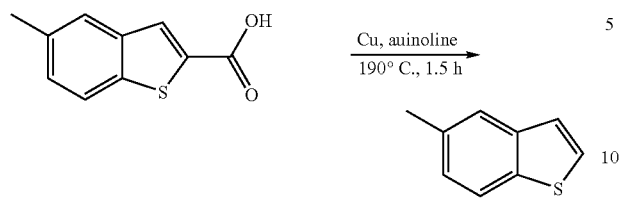

2.03 g (9.87 mmol) of the 2-carboxy-5-methylbenzo[b]thiophene obtained in Step 4 were dissolved in 10 ml of quinoline followed by the addition of 799.2 mg of copper powder and heating to 190° C. After 100 minutes, the solution was cooled followed by the addition of 40 ml of 0.5 M hydrochloric acid and extraction with ethyl acetate (40 ml×2). The organic phase was washed with 40 ml of water and then dried with magnesium sulfate. After concentrating the solvent under reduced pressure, it was purified by silica gel column chromatography (hexane:ethyl acetate=20:1) to obtain 1.41 g (9.51 mmol) of the target compound (yield of the two steps from Step 4: 96%).

$^1$H-NMR (270 MHz, CDCl$_3$) (ppm): 7.76 (d, 1H, J=8.24 Hz), 7.62 (s, 1H), 7.40 (d, 1H, J=5.44 Hz), 7.24 (m, 1H), 7.17 (d, 1H, J=8.24 Hz), 2.47 (s, 3H)

Step 6
Production of 3-chloromethylcarbonyl-5-methylbenzo[b]thiophene

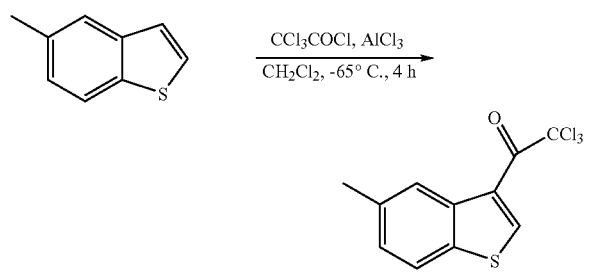

10 ml of dichloromethane were added to 1.33 g (9.97 mmol) of aluminum trichloride followed by cooling to −65° C. with dry ice and acetone. After 10 minutes, 1.12 ml (10.0 mmol) of trichloroacetylchloride were dropped in. After an additional 20 minutes, 10 ml of dichloromethane solution containing 1.41 g (9.51 mmol) of the 5-methylbenzo[b]thiophene obtained in Step 5 were dropped in and then stirred at about −65° C. After 1 hour and 40 minutes, the temperature was raised to −40° C. After an additional 1 hour and 10 minutes, the temperature was raised to 0° C. After another 1 hour and 40 minutes, 10 ml of 1 M hydrochloric acid were added and stirred. After adding 20 ml of water to the reaction system, removing the dichloromethane phase by a liquid separation procedure and then additionally extracting the aqueous phase with ethyl acetate, the aqueous phase was combined with the dichloromethane phase and then concentrated under reduced pressure. 3.2 g of the resulting residue were purified by silica gel column chromatography (silica gel: 120 g, hexane) to obtain 686.7 mg (2.34 mmol) of the target compound (yield: 24%).

$^1$H-NMR (400 MHz, CDCl$_3$) (ppm): 8.89 (s, 1H), 8.51 (s, 1H), 7.78 (d, 1H, J=8.28 Hz), 7.30 (d, 1H, J=8.32 Hz), 2.53 (s, 3H)

Step 7
Production of 3-carboxy-5-methylbenzo[b]thiophene

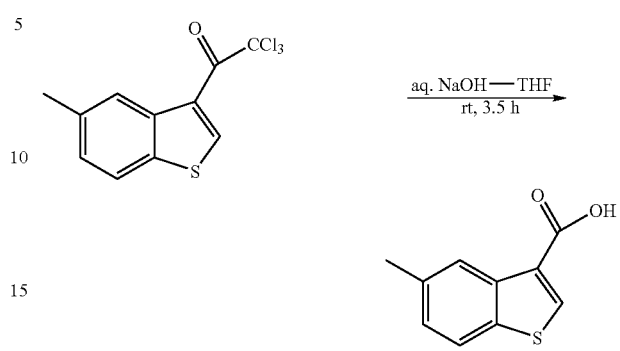

686.7 mg (2.34 mmol) of the 3-chloromethylcarbonyl-5-methylbenzo[b]thiophene obtained in Step 6 were dissolved in 2.0 ml of THF and 3.0 ml of MeOH followed by the addition of 2 ml of 2 M aqueous sodium hydroxide solution and stirring at room temperature. After 2 hours and 45 minutes, 5 ml of 2 M aqueous sodium hydroxide solution were added followed by heating to 60° C. After cooling 30 minutes later and adding 10 ml of 2 M hydrochloric acid and 30 ml of water, the solution was extracted with ethyl acetate followed by concentration under reduced pressure and drying to obtain 438.9 mg (2.28 mmol) of the target compound (yield: 97%).

$^1$H-NMR (400 MHz, CDCl$_3$) (ppm): 8.44 (s, 1H), 8.36 (s, 1H), 7.74 (d, 1H, J=8.04 Hz), 7.22 (d, 1H, J=8.28 Hz), 2.50 (s, 3H)

Step 8
Production of 3-hydroxymethyl-5-methylbenzo[b]thiophene

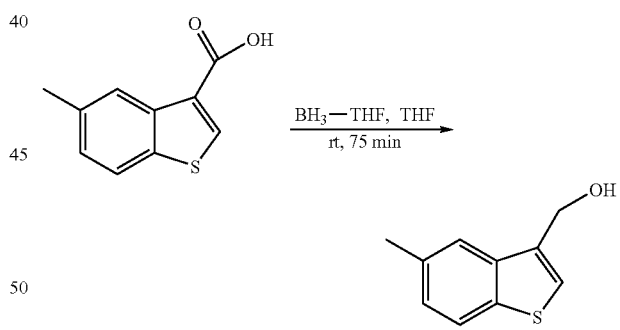

438.9 mg (2.28 mmol) of the 3-carboxy-5-methylbenzo[b]thiophene obtained in Step 7 were dissolved in 5 ml of THF followed by the addition of BH$_3$.THF complex solution and stirring at room temperature. After 1 hour and 15 minutes, 4 ml of 2 M hydrochloric acid were added and stirred followed by the addition of 50 ml of ethyl acetate. The organic phase was washed with 30 ml of water and dried with magnesium sulfate followed by concentration under reduced pressure. The resulting residue was purified with Biotage (hexane:ethyl acetate=4:1) to obtain 347.6 mg (1.95 mmol) of the target compound (yield: 86%).

$^1$H-NMR (400 MHz, CDCl$_3$) (ppm): 7.74 (d, 1H, J=8.04 Hz), 7.65 (s, 1H), 7.34 (s, 1H), 7.19 (d, 1H, J=8.28 Hz), 4.89 (s, 2H), 2.48 (s, 3H)

Step 9

Production of 3-bromomethyl-5-methylbenzo[b]thiophene

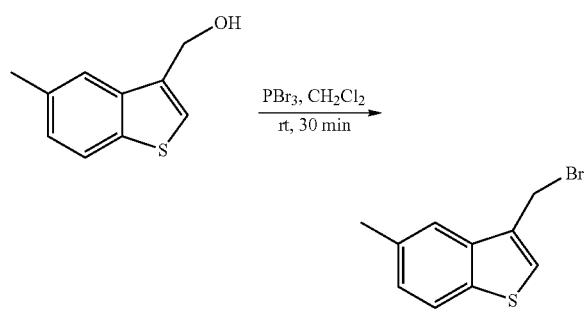

326 mg (1.83 mmol) of the 3-hydroxymethyl-5-methyl-benzo[b]thiophene obtained in Step 8 were dissolved in 10 ml of dichloromethane followed by the addition of 0.262 ml of phosphorous tribromide and stirring at room temperature. After 30 minutes, 30 ml of water were added followed by stirring for 10 minutes and extracting with dichloromethane (30 ml×2). The organic phase was then concentrated under reduced pressure and dried to obtain 397.5 mg (1.65 mmol) of the target compound (yield: 90%).

$^1$H-NMR (270 MHz, CDCl$_3$) (ppm): 7.74–7.67 (m, 2H), 7.46 (s, 1H), 7.22 (d, 1H, J=8.24 Hz), 4.74 (s, 2H), 2.51 (s, 3H)

Reference Example 5

Production of ((4-methylbenzo[b]thiophene-3-yl)methyl)trimethylammonium iodide

Step 1

Production of 2-cyano-3-nitrotoluene

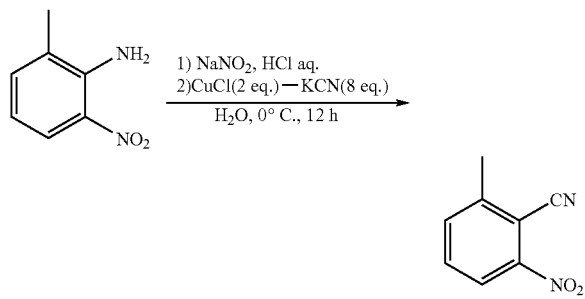

76.07 g (500 mmol) of 2-amino-3-nitrotoluene were added to 100 g (990 mmol) of 36% hydrochloric acid and 500 g of ice followed by stirring vigorously at 0° C. 80 ml of an aqueous solution containing 37.95 g (550 mmol) of sodium nitrite was then slowly dropped in while holding the temperature to 0–5° C. Following completion of dropping, 100 ml of toluene were added followed by stirring for 30 minutes at 0° C. The reaction solution was placed in an ice-NaCl bath followed by slowly adding sodium bicarbonate while stirring vigorously to neutralize the pH to about 6 (diazonium salt solution (1)).

An aqueous solution (550 ml) containing 260.5 g (4000 mmol) of potassium cyanide was slowly added at 0° C. to an aqueous solution (650 ml) containing 99.0 g (1000 mmol) of copper (I) chloride followed by stirring for 90 minutes and then adding 200 ml of ethyl acetate. The diazonium salt solution (1) prepared above was then dropped into this solution over the course of 30 minutes while holding the temperature to 0–5° C. The solution was then stirred for 12 hours in an ice bath and then warmed to room temperature. After extracting the reaction solution with ethyl acetate and washing the organic phase with water, it was dried with magnesium sulfate followed by concentrating the solvent under reduced pressure. The residue was then purified by silica gel column chromatography (hexane:ethyl acetate=20:1→10:1→7:1→5:1→3:1) to obtain 58.63 g (362 mmol) of the target compound (yield: 72%).

$^1$H-NMR (270 MHz, CDCl$_3$) (ppm): 7.68 (2H, m), 8.13 (1H, m), 2.715 (3H, s)

Step 2

Production of 3-amino-2-ethoxycarbonyl-4-methylbenzo[b]thiophene

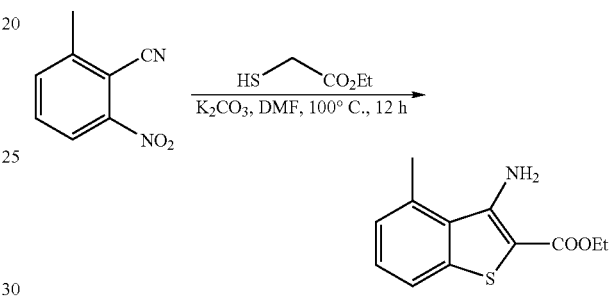

A DMF solution (250 ml) containing 58.63 g (362 mmol) of the 2-cyano-3-nitrotoluene obtained in Step 1, 47.5 g (395 mmol) of ethyl 2-mercaptoacetate and 57.5 g (416 mmol) of potassium carbonate was stirred for 12 hours at 100° C. The reaction solution was then concentrated, as is, under reduced pressure to remove the DMF to a certain degree. Water was added to dissolve inorganic substances followed by extraction with ethyl acetate. After washing the organic phase with water, it was dried with magnesium sulfate followed by concentration of the solvent under reduced pressure. The residue was then purified by silica gel column chromatography (hexane:ethyl acetate=10:1) to obtain 62.86 g (267 mmol) of the target compound (yield: 74%).

$^1$H-NMR (270 MHz, CDCl$_3$) (ppm): 7.54 (d, 1H,), 7.29 (t, 1H), 7.03 (d, 1H), 6.28 (s, 2H), 4.35 (q, 2H), 2.82 (s, 3H), 1.39 (t, 3H)

Step 3

Production of 3-cyano-2-ethoxycarbonyl-4-methylbenzo[b]thiophene

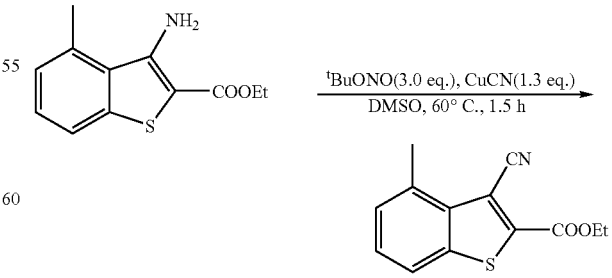

After replacing the reaction system with nitrogen, 82.0 g (795 mmol) of t-butyl nitrite and 30.9 g (345 mmol) of copper cyanide were added to 250 ml of DMSO and dissolved by stirring for 30 minutes at 55° C. Moreover, a DMSO solution (100 ml) containing 62.2 g (265 mmol) of the 3-amino-2-ethoxycarbonyl-4-methylbenzo[b]thiophene obtained in Step 2 was slowly dropped in over the course of 2 hours while holding the temperature at 55° C. After warming the reaction solution to 60° C. and stirring for 140 minutes, it was cooled to 0° C. followed by slowly adding water and stirring for 1 hour at 0° C. The reaction solution was then filtered with Celite to remove impurities, and after extracting with dichloromethane and washing the organic phase with water, it was dried with magnesium sulfate followed by concentrating the solvent under reduced pressure. The residue was then purified by silica gel column chromatography (hexane:ethyl acetate=20:1→15:1→10:1) to obtain 15.59 g (63.6 mmol) of the target compound (yield: 24%).

$^1$H-NMR (270 MHz, CDCl$_3$) (ppm): 7.73 (d, 1H), 7.44 (t, 1H), 7.30 (d, 1H), 4.50 (q, 2H), 2.95 (s, 3H), 1.47 (t, 3H)

Step 4

Production of 3-cyano-4-methylbenzo[b]thiophene

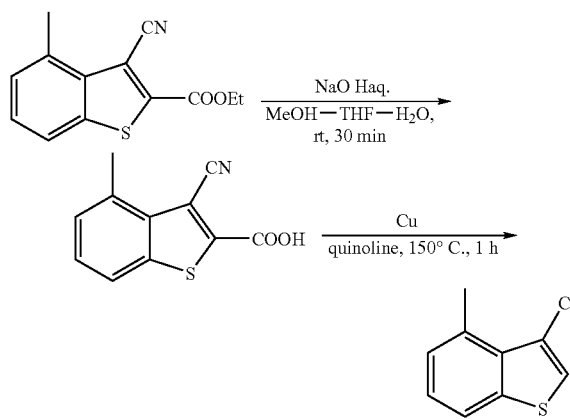

15.59 g (63.6 mmol) of the 3-cyano-2-ethoxycarbonyl-4-methylbenzo[b]thiophene obtained in Step 3 were dissolved in a mixture of methanol (150 ml), THF (150 ml) and water (150 ml) followed by the addition of 30 ml of 5 M aqueous sodium hydroxide solution and stirring for 2 hours at room temperature. After concentrating the solvent under reduced pressure, the pH was lowered to 4 by addition of 1 M hydrochloric acid and, after extracting with ethyl acetate and washing the organic phase with water, it was dried with magnesium sulfate. The solvent was then concentrated under reduced pressure to obtain 3-cyano-2-carboxy-4-methylbenzo[b]thiophene. This and 1.27 g (20 mmol) of copper powder were added to 18 ml of quinoline followed by stirring for 2 hours at 150° C. After cooling the reaction solution, it was filtered with Celite and the pH of the filtrate was lowered to 3 by addition of hydrochloric acid to transfer the quinoline as the solvent to the aqueous phase followed by extraction with ethyl acetate. After washing the organic phase with water, it was dried with magnesium sulfate and the solvent was concentrated under reduced pressure. The residue was then purified by silica gel column chromatography (hexane:ethyl acetate=20:1) to obtain 9.10 g (52.6 mmol) of the target compound (yield of the two steps: 83%).

$^1$H-NMR (270 MHz, CDCl$_3$) (ppm): 8.15 (s, 1H), 7.74 (d, 1H), 7.36 (t, 1H), 7.25 (d, 1H), 2.91 (s, 3H)

Step 5

Production of 3-((N,N-dimethylamino)methyl)-4-methylbenzo[b]thiophene

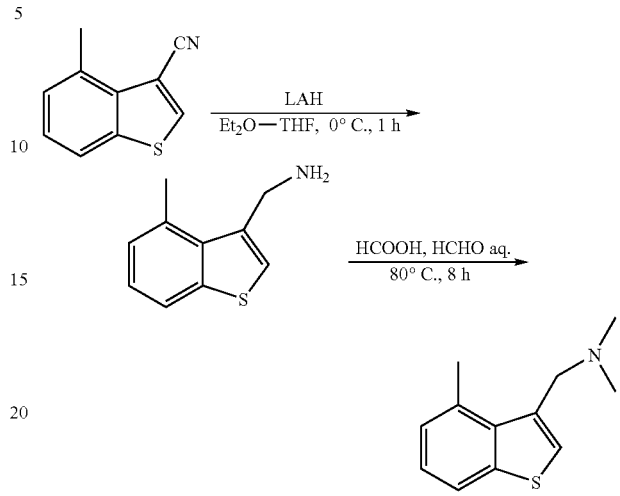

After dropping a diethyl ether (20 ml) and THF (20 ml) solution containing 9.10 g (52.6 mmol) of the 3-cyano-4-methylbenzo[b]thiophene obtained in Step 4 into 50 ml of a diethyl ether suspension of 2.0 g (53 mmol) of lithium aluminum hydride over the course of 15 minutes at 0° C., the solution was stirred for 30 minutes at room temperature. Following completion of the reaction, excess LAH in the reaction solution was treated with hydrochloric acid followed by the addition of aqueous sodium hydroxide solution to make alkaline. After saturating the aqueous phase with potassium carbonate, extracting with dichloromethane and washing the organic phase with water, it was dried with magnesium sulfate. The solvent was then concentrated under reduced pressure to obtain 3-aminomethyl-4-methylbenzo[b]thiophene. 11.5 (250 mmol) of formic acid and 10.0 g (123 mmol) of 37% aqueous formaldehyde solution were sequentially added to this followed by stirring for 5 hours at 80° C. Following completion of the reaction, after adding aqueous hydrochloric acid solution to the reaction solution, it was concentrated under reduced pressure to remove the formic acid and formaldehyde. Aqueous sodium hydroxide solution was then added to make the solution alkaline followed by extraction with dichloromethane. After washing the organic phase with water, it was dried with magnesium sulfate and the solvent was concentrated under reduced pressure. The residue was then purified by silica gel column chromatography (hexane:ethyl acetate=10:1) to obtain 2.61 g (12.8 mmol) of the target compound (yield of the two steps: 24%). Confirmation of the compound was carried out by identifying from $^1$H-NMR.

$^1$H-NMR (270 MHz, CDCl$_3$) (ppm): 7.66 (s, 1H), 7.26–7.09 (m, 3H), 3.65 (s, 2H), 2.85 (s, 3H), 2.27 (s, 6H)

Step 6

Production of ((4-methylbenzo[b]thiophene-3-yl)methyl)trimethylammonium iodide

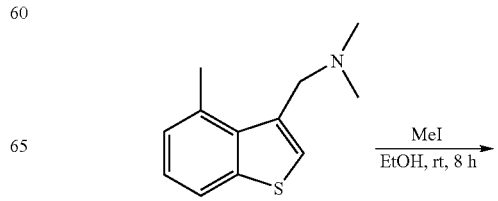

-continued

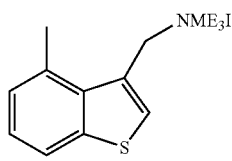

3.69 g (26 mmol) of methyl iodide were added to 20 ml of an ethanol solution containing 2.61 g (12.8 mmol) of the 3-((N,N-dimethylamino)methyl)-4-methylbenzo[b]thiophene obtained in Step 5 followed by stirring for 18 hours at room temperature. As this results in a white suspension, after filtering out the excess methyl iodide and solvent, it was washed with ethanol (10 ml×2) and diethyl ether (10 ml×3) to obtain 3.08 g (8.88 mmol) of the target compound in the form of a white solid (yield: 69%).

$^1$H-NMR (270 MHz, DMSO)(ppm): 8.19 (s, 1H), 7.93 (d, 1H), 7.36–7.25 (m, 2H), 4.91 (s, 2H), 3.05 (s, 9H), 2.77 (s, 3H)

Reference Example 6

Production ((1,4-dimethylindole-3-yl)methyl)methylammonium iodide
Step 1
Production of 4-methylindole

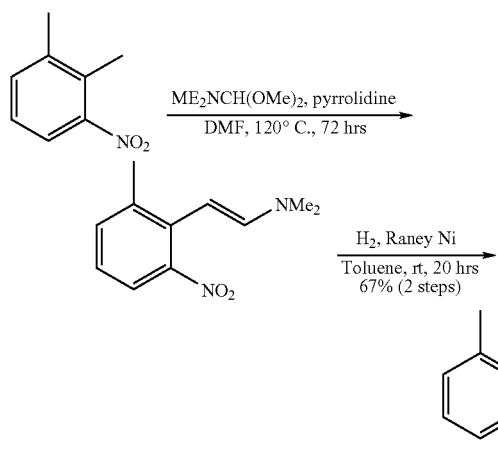

30.5 g (256 mmol) of N,N-dimethylformamidedimethylacetal and 10.9 g (153 mmol) of pyrrolidine were added to 150 ml of an N,N-dimethylformamide solution containing 19.4 g (128 mmol) of 2,3-dimethylnitrobenzene. After stirring the resulting solution for 72 hours at 120° C., it was concentrated as is. 100 ml of toluene were added to the resulting brown oily substance followed by the addition of 11 g of Raney nickel (50%, aqueous slurry, pH>9) and stirring. The inside of the reaction vessel was replaced with hydrogen gas followed by stirring for 20 hours at room temperature in a hydrogen gas atmosphere. After filtering the reaction solution with Celite, the filtrate was concentrated to obtain 30 g of a black solution. This was then purified by silica gel column chromatography (hexane:ethyl acetate=10:1) to obtain 11.33 g (86 mmol) of the target compound (yield of the two steps: 67%). Confirmation of the compound was carried out by identifying using $^1$H-NMR.

$^1$H-NMR (270 MHz, CDCl$_3$) (ppm): 7.28–7.07 (m, 3H), 6.93 (m, 1H), 6.57 (m, 1H), 2.57 (s, 3H)

Step 2
Production of 1,4-dimethylindole

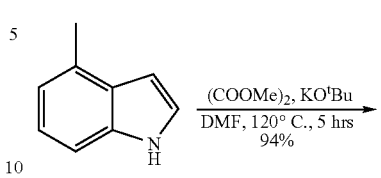

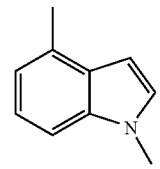

12.7 g (134 mmol) of t-butoxypotassium and 80 ml of N,N-dimethylformamide were added to a pre-dried reaction vessel. 8.9 g (67.9 mmol) of the 4-methylindole obtained in Step 1 were added followed by stirring for 35 minutes at room temperature. 15.8 g (134 mmol) of dimethyl oxalate were added to this followed by stirring for 5 hours and 30 minutes at 120° C. After concentrating under reduced pressure, 200 ml of water were added followed by treatment with 1 M hydrochloric acid to make acidic (pH=3) followed by extraction with ethyl acetate (200 ml×2) and drying with anhydrous magnesium sulfate. After distilling off the solvent under reduced pressure, it was purified by silica gel column chromatography (hexane:ethyl acetate=5:1) to obtain 9.24 g (53 mmol) of the target compound (yield: 94%). Confirmation of the compound was carried out by identifying using $^1$H-NMR.

$^1$H-NMR (270 MHz, CDCl$_3$) (ppm): 7.25–7.09 (m, 2H), 7.03 (m, 1H), 6.90 (m, 1H), 6.49 (m, 1H), 3.78 (s, 3H), 2.55 (s, 3H)

Step 3
Production of 1,4-dimethyl-3-(N,N-dimethylaminomethyl)indole

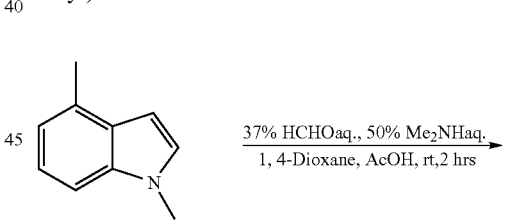

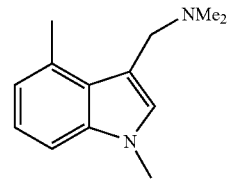

5.9 ml (72.0 mmol) of 37% aqueous formaldehyde solution and 7.08 ml (78 mmol) of 50% aqueous dimethylamine solution were sequentially added to a mixed system containing 25 ml each of 1,4-dioxane and acetic acid. After cooling to room temperature, as this reaction generates heat, 10 ml of a 1,4-dioxane solution containing 9.24 g (63.6 mmol) of the 1,4-dimethylindole obtained in Step 2 were added followed by stirring for 2 hours at room temperature. The reaction solution was then concentrated as is. 5 M aqueous sodium hydroxide solution were then added to the residue to make alkaline (pH=12) and bring to a total volume of 100 ml followed by extraction with ethyl acetate (100 ml×2). The organic phase was then dried with anhydrous magnesium sulfate and concentrated under reduced pressure to obtain 12.93 g (63.9 mmol) of the target compound (crude yield: 100.4%). Confirmation of the compound was carried out by identifying using ¹H-NMR.

¹H-NMR (270 MHz, CDCl₃) (ppm): 7.15–7.06 (m, 2H), 6.91 (m, 1H), 6.85 (m, 1H), 3.71 (s, 3H), 3.59 (s, 2H), 2.74 (s, 3H), 2.27 (s, 6H)

Step 4

Production of ((1,4-dimethylindole-3-yl)methyl)trimethylammonium iodide

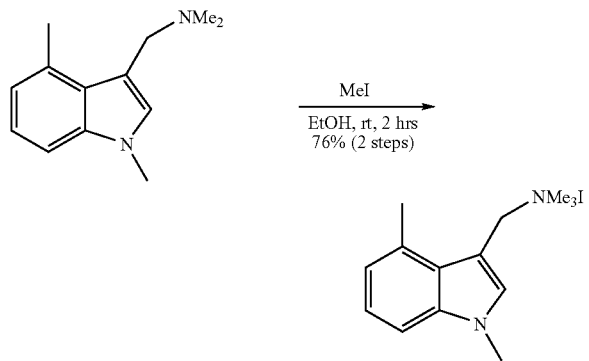

12.93 g (63.6 mmol) of the 1,4-dimethyl-3-(N,N-dimethylaminomethyl)indole obtained in Step 3 were dissolved in 60 ml of ethanol followed by the addition of 4.36 ml (70 mmol) of methyl iodide. A white precipitate formed after stirring for 2 hours at room temperature. This was then filtered, washed twice with 10 ml of ethanol and dried in a vacuum to obtain 16.66 g (48.4 mmol) of the target compound (yield of the two steps: 76%). Confirmation of the compound was carried out by identifying using ¹H-NMR.

¹H-NMR (270 MHz, DMSO) (ppm): 7.65 (s, 1H), 7.36 (d, 1H), 7.13 (t, 1H), 6.91 (d, 1H), 4.74 (s, 2H), 3.82 (s, 3H), 3.01 (s, 9H), 2.65 (s, 3H)

Reference Example 7

Production of 4-(5-methoxybenzimidazole-2-ylthio)butanoate ester hydrogen bromide salt

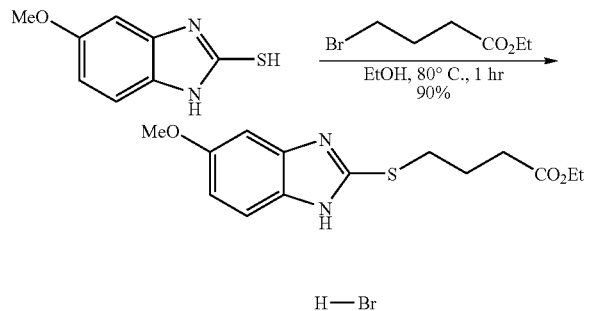

6.48 g (33.2 mmol) of 4-bromobutanoate ethyl ester were added to 10 ml of an ethanol solution containing 5.0 g (27.7 mmol) of 5-methoxybenzimidazole-2-thiol followed by stirring for 1 hour at 80° C. and adding 90 ml of ethyl acetate. The reaction solution was returned to room temperature and the formed crystals were filtered out followed by drying to obtain 9.34 g of the target compound (yield: 90%).

¹H-NMR (270 MHz, CDCl₃) (ppm): 7.65 (d, 1H, J=8.91 Hz), 7.24 (s, 1H), 7.00 (dd, 1H, J=2.43, 8.91 Hz), 4.21 (q, 2H, J=7.29 Hz), 3.83 (s, 3H), 3.74 (m, 2H), 2.61 (m, 2H), 2.10 (m, 2H), 1.30 (t, 3H, J=7.29 Hz)

Example 1

Production of Compound No. 39

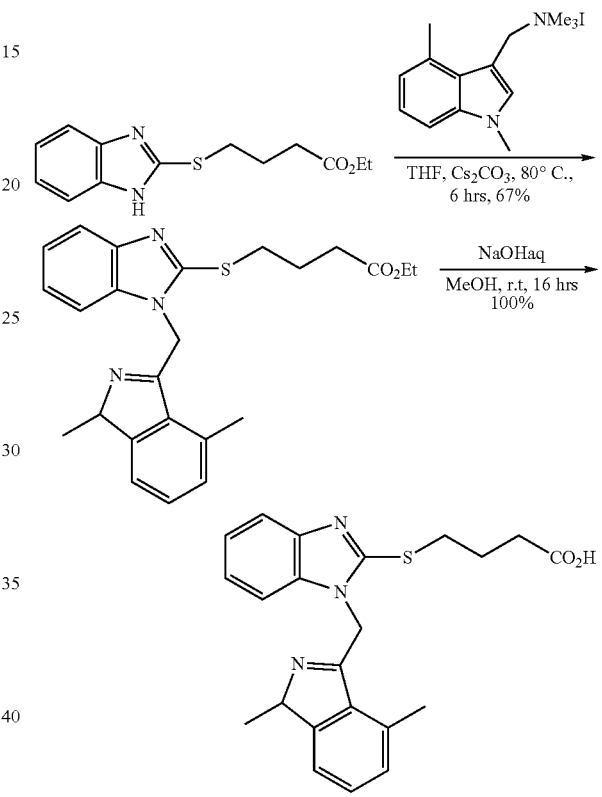

480 mg (2.49 mmol) and 10 ml of tetrahydrofuran were added to a pre-dried reaction vessel. 505 mg (1.91 mmol) of the 4-(benzimidazole-2ylthio)butanoate ethyl ester obtained in Reference Example 3 and 724 mg (2.10 mmol) of ((1,4-dimethylindole-3-yl)methyl)trimethylammonium iodide were added followed by stirring for 6 hours at 80° C. After filtering the solution by passing through Celite, it was concentrated under reduced pressure. The residue was then purified by silica gel column chromatography (dichloromethane:ethyl acetate=8:1) to obtain 540 mg (1.28 mmol) of 4-(1-((1,4-dimethylindole-3-yl)methyl)benzimidazole-2-ylthio)butanoate ethyl ester (yield: 67%).

2.0 ml of a 2M aqueous sodium hydroxide solution were then added to 6 ml of a methanol solution containing 540 mg (1.28 mmol) of the resulting 4-(1-((1,4-dimethylindole-3-yl) methyl)benzimidazole-2-ylthio)butanoate ethyl ester. After stirring for 16 hours at room temperature, 6 M hydrochloric acid was added to stop the reaction. The solvent was removed to a certain degree by concentration under reduced pressure followed by extraction with ethyl acetate. After washing the ethyl acetate phase with saturated brine, it was dried with anhydrous magnesium sulfate. After distilling off the solvent under reduced pressure, it was purified by silica gel column chromatography (dichloromethane:methanol=8:1) to obtain 502 mg (1.28 mmol) of the target compound (yield: 100%). Confirmation of the compound was carried out by identifying from its molecular weight using LC-MS.

Calculated value M=393.15, Measured value (M+H)$^+$ =394.2

Example 2

The following compounds and the compounds in the following table were synthesized according to the same method as Example 1 using the compounds indicated in Reference Example 2 or 3 as well as various quaternary ammonium salts or halide derivatives synthesized with reference to Reference Examples 4–6 and other references described in the text. Confirmation of the compounds was carried out by identifying from their molecular weights using LC-MS. However, some of the compounds were synthesized using conditions that somewhat differed from those of Example 1, including conditions such as the use of DMF and so forth for the solvent and the use of potassium carbonate for the base in coupling, the use of THF and EtOH for the solvent in hydrolysis, and the use of a temperature of room temperature to 50° C.

In addition, the following compounds were similarly synthesized.

4-(1-(2-(1-methylindole-3-yl)ethyl)benzimidazole-2-ylthio)butanoic acid (Compound No. 1153)

In this case however, a methanesulfonate ester of 2-(1-methylindole-3-yl)ethanol was used instead of quaternary ammonium salt and halide derivative. Identification of the compound was carried out using LC-MS. The yield was 19% (two steps of N-alkylation and ester hydrolysis).

Calculated value M=393.15, Measured value (M+H)$^+$ =394.0

4-[(1-(4-methyl-7-chlorobenzo[b]thiophene-3-yl)methyl) benzimidazole-2-ylthio)butanoic acid (Compound No. 1154)

Yield: 15% (two steps of N-alkylation and ester hydrolysis)

Calculated valve M=430.06, Measured value (M+H)$^+$ =431.2

$^1$H-NMR (270 MHz, DMSO-d6) (ppm): 12.17 (br, 1H), 7.63 (d, 1H, J=7.83 Hz), 7.47–7.40 (m, 2H), 7.26 (d, 1H, J=8.10 Hz), 7.22–7.11 (m, 2H), 6.46 (s, 1H), 5.86 (s, 2H), 3.34 (t, 2H, J=7.29 Hz), 2.84 (s, 3H), 2.34 (t, 2H, J=7.29 Hz), 1.94 (m, 2H)

4-(1-(4-methyl-7-bromobenzo[b]thiphene-3-yl)methyl) benzoimidazole-2-ylthio)butanoic acid (Compound No. 1155)

Yield: 56% (two steps of N-alkylation and ester hydrolysis)

Calculated value M=474.01, Measured value (M+H)+ =477.0

$^1$H-NMR (270 MHz, DMSO-d6) (ppm): 12.18 (br, 1H), 7.63 (d, 1H, J=7.56 Hz), 7.53 (d, 1H, J=7.56 Hz), 7.46 (d, 1H, J=7.56 Hz), 7.22–7.11 (m, 3H), 6.46 (s, 1H), 5.85 (s, 2H), 3.34 (t, 2H, J=7.29 Hz), 2.83 (s, 3H), 2.34 (t, 2H, J=7.29 Hz), 1.97 (m, 2H)

| Compound No. | Calculated value M | Measured value (M + H)$^+$ | Yield (two steps) % |
|---|---|---|---|
| 35 | 393.15 | 394.2 | 10 |
| 36 | 393.15 | 394.2 | 15 |
| 37 | 393.15 | 394.1 | 25 |
| 38 | 393.15 | 394.1 | 19 |
| 39 | 393.15 | 394.2 | 67 |
| 40 | 407.17 | 408.2 | 3 |
| 41 | 413.10 | 414.3 | 74 |
| 42 | 397.13 | 398.3 | 26 |
| 43 | 409.15 | 410.1 | 3 |
| 44 | 455.17 | 456.2 | 1 |
| 45 | 517.18 | 518.1 | 8 |
| 46 | 413.10 | 414.1 | 53 |
| 47 | 397.13 | 398.1 | 56 |
| 48 | 409.15 | 410.3 | 81 |
| 49 | 404.13 | 405.2 | 31 |
| 50 | 409.15 | 410.1 | 24 |
| 52 | 382.08 | 383.2 | 65 |
| 54 | 416.04 | 417.3 | 100 |
| 56 | 396.10 | 397.3 | 63 |
| 58 | 396.10 | 397.1 | 95 |
| 59 | 416.04 | 417.1 | 44 |
| 63 | 410.11 | 411.3 | 33 |
| 514 | 408.17 | 408.3 | 83 |
| 519 | 421.18 | 422.2 | 36 |
| 521 | 441.13 | 442.3 | 58 |
| 532 | 410.11 | 411.3 | 65 |
| 534 | 444.07 | 445.3 | 80 |
| 536 | 424.13 | 425.3 | 73 |
| 538 | 424.13 | 425.2 | 11 |
| 615 | 461.07 | 462.0 | 89 |
| 628 | 450.00 | 451.0 | 78 |

Example 3

Production of Compound No. 148

Step 1

Production of ((benzothiophene-3-yl)methyl)(4-methoxy-2-nitrophenyl)amine

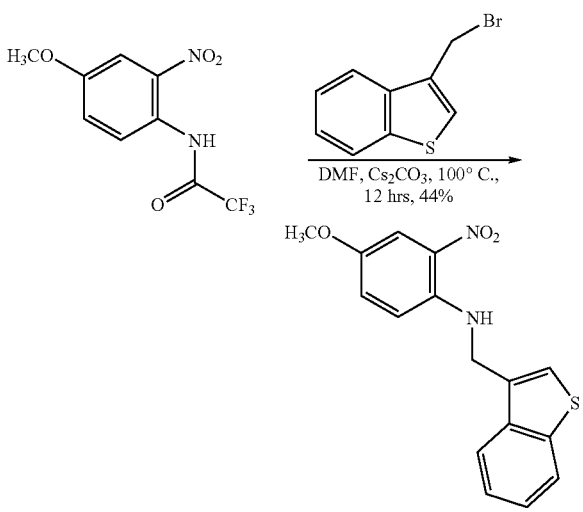

740 mg (2.8 mmol) of 4-methoxy-2-nitrotrifluoroanilide were dissolved in 5 ml of dimethylformamide followed by the sequential addition of 503 mg (3.64 mmol) of potassium carbonate and 773 mg (3.4 mmol) of 3-bromomethylbenzothiophene and heating to 100° C. After 12 hours, 5 ml of 5 M aqueous sodium hydroxide solution were added and refluxed, as is, for 1 hour. After 15 minutes, the solution was cooled to room temperature followed by the addition of 10 ml of water and extraction with chloroform. After washing the organic phase twice with 25 ml of saturated brine and drying with magnesium sulfate, it was concentrated and dried under reduced pressure. The residue was then purified by silica gel column chromatography (hexane:ethyl acetate=60:1) to obtain 400 mg of ((benzothiophene-3-yl)methyl)(4-methoxy-2-nitrophenyl)amine in the form of an orange powder (yield: 44%).

Step 2

Production of 1-((benzothiophene-3-yl)methyl)-5-methoxybenzoimidazole-2-thiol 4 ml of ethanol and 4 ml of 1,4-dioxane were added to 400 mg (1.23 mmol) of ((benzothiophene-3-yl)methyl)(4-methoxy-2-nitrophenyl)amine followed by the addition of 0.34 ml of 5 M aqueous sodium hydroxide solution and refluxing while heating. After 15 minutes, the reaction solution was removed from the oil bath followed by the divided addition of 320 mg (4.9 mmol) of zinc powder. The reaction solution was again refluxed while heating for 1 hour. After allowing to cool to room temperature, the zinc was filtered out and the filtrate was concentrated under reduced pressure followed by extraction with chloroform. The organic phase was washed twice with 5 ml of saturated brine followed by drying with magnesium sulfate, concentration under reduced pressure and drying to obtain 309 mg of a brown oil.

Continuing, the resulting brown oil was dissolved in 10 ml of ethanol followed by the addition of 2.5 ml (42 mmol) of carbon disulfide and refluxing. After 12 hours, the reaction solution was returned to room temperature and concentrated under reduced pressure followed by the addition of 2 ml of ethanol and irradiating with ultrasonic waves to break into fine fragments that were then filtered. The resulting powder was washed twice with 2 ml of ethanol and then dried to obtain 120 mg (0.37 mmol) of 1-((benzothiophene-3-yl)methyl)-5-methoxybenzimidazole-2-thiol (yield of the two steps: 30%).

Step 3

Production of 4-(1-((benzothiophene-3-yl)methyl)-5-methoxybenzimidazole-2-ylthio)butanoate ethyl ester

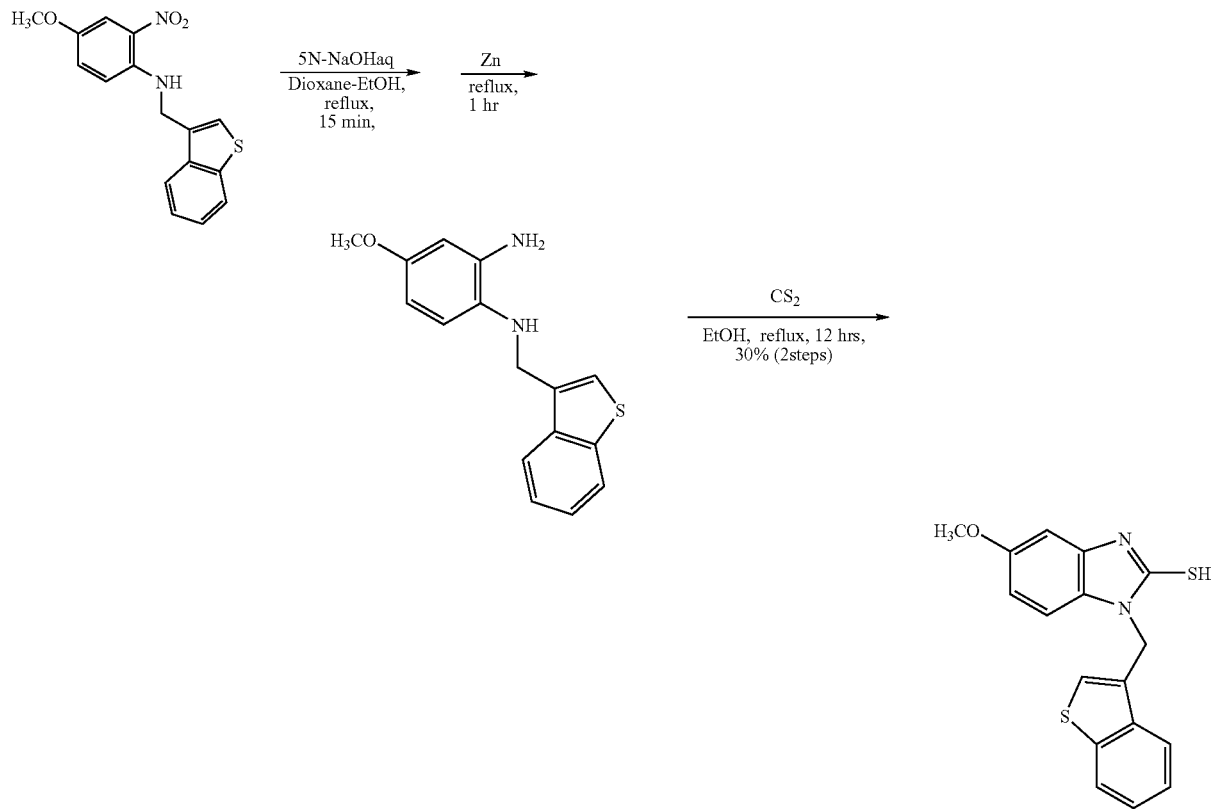

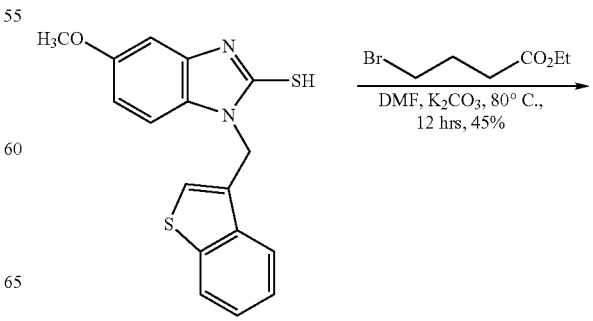

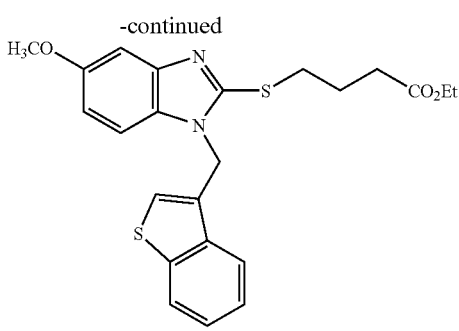

101 mg (0.30 mmol) of 1-((benzothiophene-3-yl)methyl)-5-methoxybenzimidazole-2-thiol were dissolved in 2 ml of dimethylformamide followed by the addition of 62 mg (0.45 mmol) of potassium carbonate and 53 mg (0.40 mmol) of 4-bromobutanoate ethyl ester and heating to 80° C. After 12 hours, the reaction solution was concentrated under reduced pressure and extracted with diethyl ether followed by washing twice with 10 ml of saturated brine and drying with magnesium sulfate. The solvent was then concentrated under reduced pressure and the residue was purified by silica gel column chromatography (hexane:ethyl acetate=1:1) to obtain 60 mg (0.136 mmol) of 4-(1-((benzothiophene-3-yl)methyl)-5-methoxybenzimidazole-2-ylthio)butanoate ethyl ester (yield: 45%).

Step 4

Production of 4-(1-((benzothiophene-3-yl)methyl)-5-methoxybenzimidazole-2-ylthio)butanoic acid

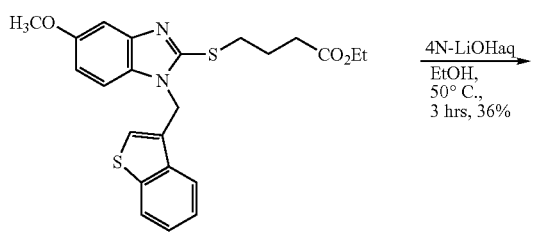

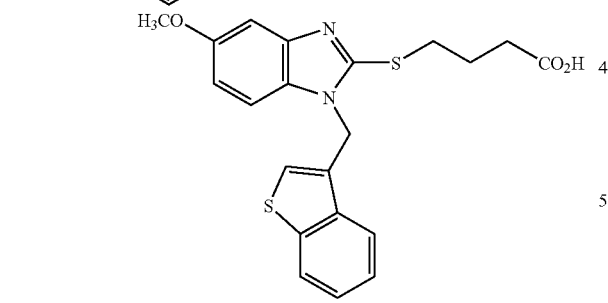

60 mg (0.136 mmol) of 4-(1-((benzothiophene-3-yl)methyl)-5-methoxybenzimidazole-2-ylthio)butanoate ethyl ester were dissolved in 2 ml of methanol followed by the addition of 0.5 ml of 4 M aqueous sodium hydroxide solution. After stirring for 3 hours at 50° C., 6 M hydrochloric acid was added to stop the reaction followed by concentrating under reduced pressure and extracting with chloroform. After washing the organic phase with saturated brine, it was dried with anhydrous magnesium sulfate. The solvent was concentrated under reduced pressure and the residue was purified by silica gel column chromatography (ethyl acetate) to obtain 20 mg (0.048 mmol) of the target compound (yield: 36%). Confirmation of the compound was carried out by identifying from the molecular weight using LC-MS.

Calculated value M=412.09, Measured value (M+H)$^+$ =413.1

Example 4

Production of Compound No. 135

The target compound was obtained according to the same method as Example 3.

However, ((1,4-dimethylindole-3-yl)methyl) trimethylammonium iodide was used in the reaction corresponding to Step 1.

Confirmation of the compound was carried out by identifying from the molecular weight using LC-MS.

Calculated value M=423.16, Measured value (M+H)$^+$ =424.3

Production of Compound No. 137

The target compound was obtained according to the same method as Example 3.

However, ((1-methyl-4-chloroindole-3-yl)methyl) trimethylammonium iodide was used in the reaction corresponding to Step 1.

Confirmation of the compound was carried out by identifying from the molecular weight using LC-MS.

Calculated value M=443.11, Measured value (M+H)$^+$ =444.3

Example 5

Production of Compound No. 244

The target compound was obtained using the same method as Example 3. However, 4-cyano-2-nitrotrifluoroacetonitrile was used as the reagent corresponding to Step 1. In addition, the step in which the 2-nitroaniline derivative is reduced to an orthophenylenediamine derivative, and the step in which this is cyclized to a benzimidazole-2-thiol derivative were carried out using the methods described below.

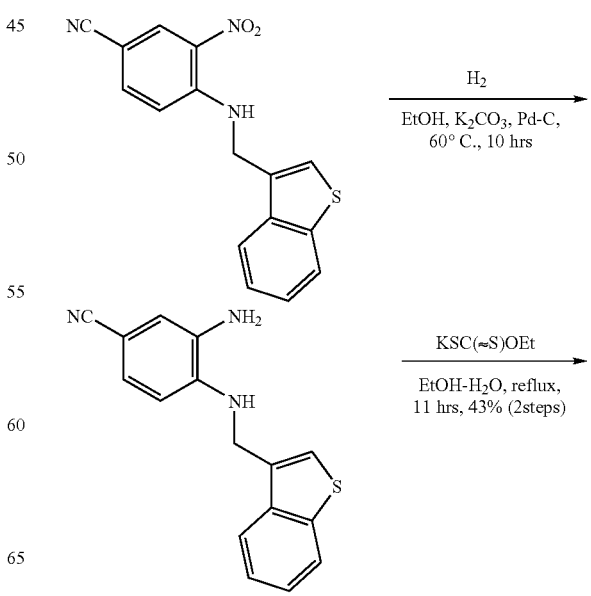

-continued

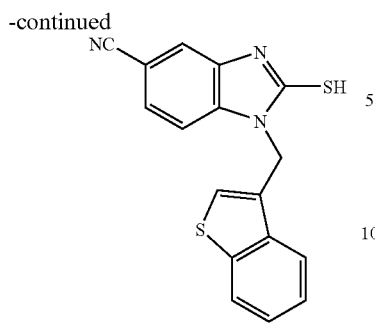

10 ml of ethanol were added to 1.1 g (3.56 mmol) of ((3-benzothiophenyl)methyl)(4-cyano-2-nitrophenyl)amine followed by the addition of 2.4 g (17.8 mmol) of potassium carbonate. After replacing the reaction system with nitrogen, 220 mg of 10% palladium-carbon were added followed by replacing the reaction system with hydrogen and heating to 60° C.

After 4 hours and 30 minutes, an additional 220 mg of 10% palladium-carbon were added followed by replacing the reaction system with hydrogen and heating to 60° C. 5 hours and 10 minutes after the start of the reaction, the reaction system was cooled to room temperature. The reaction solution was then filtered with Celite and concentrated under reduced pressure to obtain 0.93 g of a liquid residue. Continuing, 0.93 g (2.63 mmol) of ((2-benzothiophenyl)methyl)(2-amino-4-methylphenyl)amine were dissolved in 10 ml of ethanol and 2 ml of water followed by refluxing after adding 2.1 g (13.3 mmol) of potassium ethylxanthate. After 11 hours, 12.5 ml of 40% aqueous acetic acid solution were dropped in. After cooling to room temperature and concentrating under reduced pressure, the residue was purified by silica gel column chromatography (hexane:acetone=2:1) to obtain 491.7 mg of 1-((2-benzothiophenyl)methyl)-6-cyanobenzimidazole-2-thiol (yield of the two steps: 43%). Confirmation of compound no. 244 was carried out by identifying from the molecular weight using $^1$H-NMR and LC-MS.

Calculated value M=407.08, Measured value (M+H)$^+$= 408.2

$^1$H-NMR (400 MHz, CDCl$_3$) (ppm): 7.94 (s, 1H), 7.76 (dd, 1H), 7.52 (dd, 1H), 7.42 (m, 3H), 7.31 (d, 1H), 7.00 (s, 1H), 5.56 (s, 2H), 3.35 (t, 2H), 2.47 (t, 2H), 2.15 (p, 2H)

Example 6

The following target compounds were obtained using the same method as Example 5.

Production of Compound No. 340

4-methyl-2-nitrotrifluoroacetoanilide was used as the reagent corresponding to Step 1.

Confirmation of compound no. 340 was carried out by identifying from the molecular weight using LC-MS.

Calculated value M=396.10, Measured value (M+H)$^+$ =397.0

Production of Compound No. 436

5-methyl-2-nitrotrifluoroacetoanilide was used as the reagent corresponding to Step 1.

Confirmation of compound no. 436 was carried out by identifying from the molecular weight using LC-MS.

Calculated value M=396.10, Measured value (M+H)$^+$ =397.0

Example 7

Production of Compound No. 34

Step 1

Production of ((1-methylindole-3-yl)methyl)(2-aminophenyl)amine

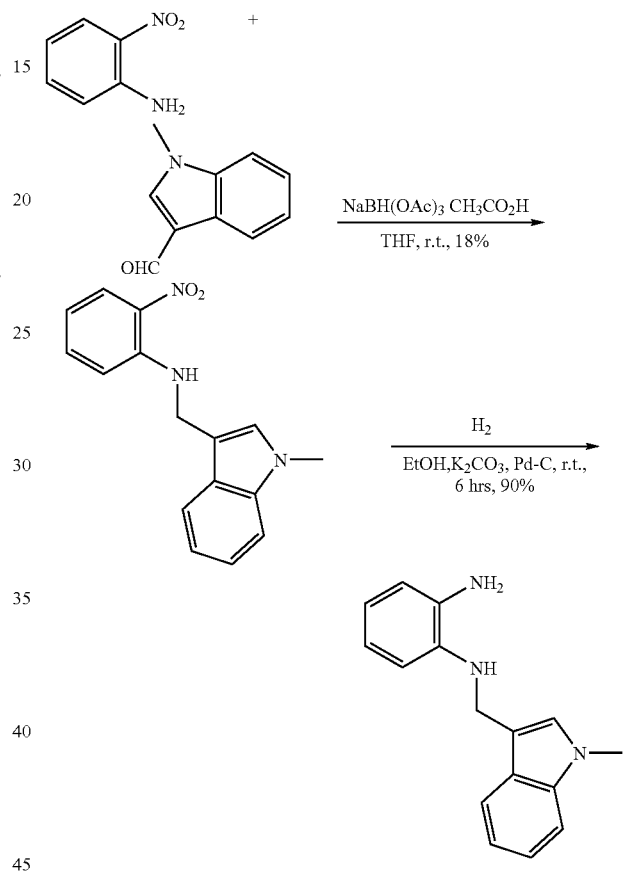

829 mg (6 mmol) of 2-nitroaniline and 1242 mg (7.8 mmol) of 1-methylindole carboxyaldehyde were dissolved in 20 ml of tetrahydrofuran followed by the sequential addition of 200 μl of acetic acid and 5087 mg (24 mmol) of NaBH(OAc)$_3$ and stirring overnight at room temperature. After adding saturated aqueous sodium bicarbonate solution, extracting with ethyl acetate and drying with anhydrous magnesium sulfate, the solvent was distilled off and the residue was purified by silica gel column chromatography (hexane:ethyl acetate=95:5) to obtain 264 mg of ((1-methylindole-3-yl)methyl)(2-nitrophenyl)amine (yield: 18%). 264 mg (0.939 mmol) of ((1-methylindole-3-yl)methyl)(2-nitrophenyl)amine were then dissolved in 10 ml of ethanol followed by the addition of 50 mg (0.047 mmol) of 10% Pd—C and stirring for 6 hours at room temperature in a hydrogen atmosphere. After completion of the reaction, the Pd—C was filtered out and the solvent was distilled off under reduced pressure to obtain 212 mg of ((1-methylindole-3-yl)methyl)(2-aminophenyl)amine (yield: 90%).

Step 2

Production of 1-((1-methylindole-3-yl)methyl)benzimidazole-2-thiol

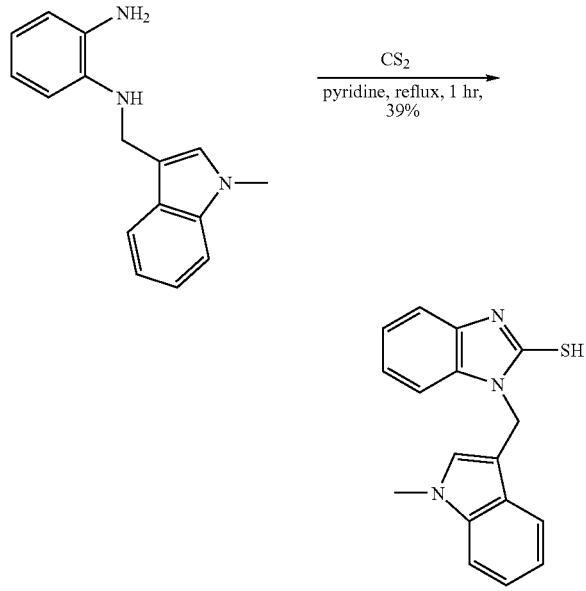

212 mg (0.845 mmol) of ((1-methylindole-3-yl)methyl)(2-aminophenyl)amine were dissolved in 1 ml of pyridine followed by the addition of 1 ml (16.9 mmol) of carbon disulfide and refluxing for 1 hour in a nitrogen atmosphere. The solvent was distilled off followed by purification by silica gel column chromatography (hexane:ethyl acetate=2:1) to obtain 96 mg of 1-((1-methylindole-3-yl)methyl)benzimidazole-2-thiol (yield: 39%).

Step 3

Production of 4-(1-((1-methylindole-3-yl)methyl)benzimidazole-2-ylthio)butanoic acid

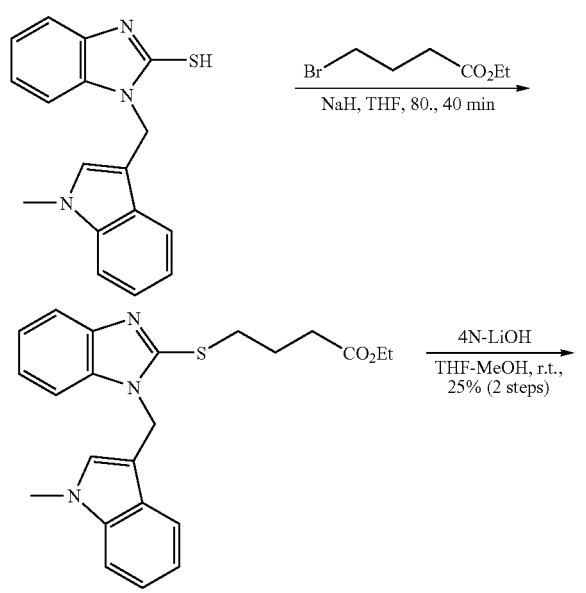

12 mg (0.342 mmol) of sodium hydride and 2 ml of tetrahydrofuran were added to a pre-dried reaction vessel. 50 mg (0.171 mmol) of 1-((1-methylindole-3-yl)methyl)benzimidazole-2-thiol and 34 μl (0.23 mmol) of 4-bromobutanoate ethyl ester were then added to the reaction vessel followed by stirring for 40 minutes at 60° C. Water was then added followed by extraction with ethyl acetate. After drying the ethyl acetate phase with anhydrous magnesium sulfate, the reaction solution was concentrated under reduced pressure and the resulting residue was purified by silica gel column chromatography (hexane:ethyl acetate=3:1) to obtain 4-(1-((1-methylindole-3-yl)methyl)(benzimidazole-2-ylthio)butanoate ethyl ester. Continuing, 0.25 ml of 4 M aqueous lithium hydroxide solution were added to 1 ml of tetrahydrofuran containing this 4-(1-((1-methylindole-3-yl)methyl)(benzimidazole-2-ylthio)butanoate ethyl ester and 0.5 ml of methanol. After stirring overnight at room temperature, 6 M hydrochloric acid was added to stop the reaction followed by extraction with ethyl acetate. After washing the ethyl acetate phase with saturated brine, it was dried with anhydrous magnesium sulfate. The solvent was then distilled off under reduced pressure to obtain 16 mg (0.042 mmol) of the target compound (yield: 25%).

Confirmation of the compound was carried out by identifying from the molecular weight using LC-MS.

Calculated value M=379.14, Measured value (M+H)$^+$ =380.2

Example 8

Production of 5-(1-((1,4-dimethylindole-3-yl)methyl)benzimidazole-2-yl)pentanoic acid Step 1

Production of 5-(benzimidazole-2-yl)pentanoate ethyl ester

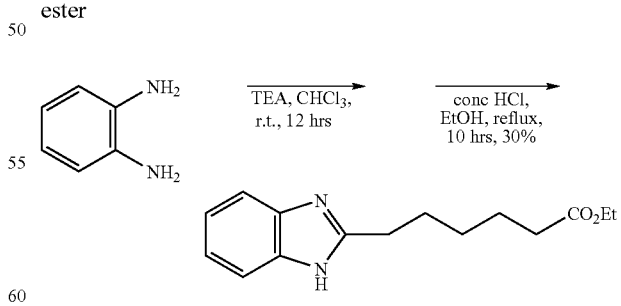

696 μl (5.0 mmol) of triethylamine and 893 mg (5.0 mmol) of methyladipochloride were dropped into 10 ml of a chloroform solution containing 540 mg (5.0 mmol) of orthophenylenediamine followed by stirring for 12 hours at room temperature. 20 ml of ethanol and 4 ml of concentrated hydrochloric acid were then added followed by stirring for 10 hours while heating and refluxing. The reaction solution was then neutralized using 5 M aqueous sodium hydroxide solution followed by extraction with ethyl acetate. After washing with water and concentrating under reduced pressure, the residue was purified by silica gel column chromatography (ethyl acetate only) to obtain 359 mg of 5-(benzimidazole-2-yl)pentanoate ethyl ester (yield: 30%).

Step 2

Production of 5-(1-((1,4-dimethylindole-3-yl)methyl) benzimidazole-2-yl)pentanoic acid

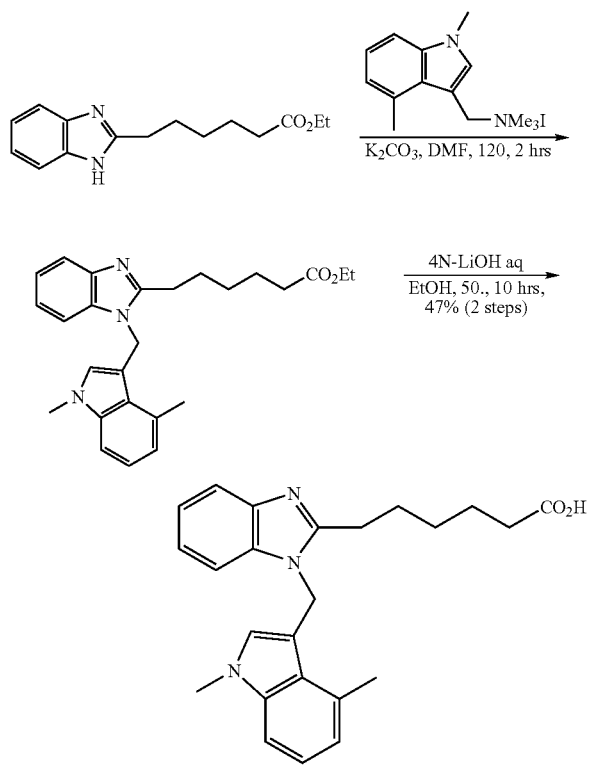

42 mg (0.3 mmol) of potassium carbonate and 103 mg (0.3 mmol) of ((1,4-dimethylindole-3-yl)methyl)trimethylammonium iodide were added to 2 ml of DMF solution containing 50 mg (0.2 mmol) of the resulting 5-(benzimidazole-2-yl)pentanoate ethyl ester followed by stirring for 2 hours at 120° C. The resulting solution was extracted with dichloromethane, washed with water and concentrated followed by purification of the residue by column chromatography (hexane:ethyl acetate=1:2). 5 ml of ethanol and 0.5 ml of 4 M aqueous sodium hydroxide solution were then added to this followed by stirring for 10 hours at 50° C. and then the addition of 6 M hydrochloric acid to stop the reaction. The solution was extracted with chloroform, and after washing with water and concentrating under reduced pressure, the residue was purified by silica gel column chromatography (chloroform:methanol=10:1) to obtain 35 mg of the target compound (yield of the two steps: 47%). Confirmation of the compound was carried out by identifying from the molecular weight using LC-MS.

Calculated value M=375.19, Measured value (M+H)$^+$=376.5

Example 9

Production of Sodium Salt of Compound No. 519

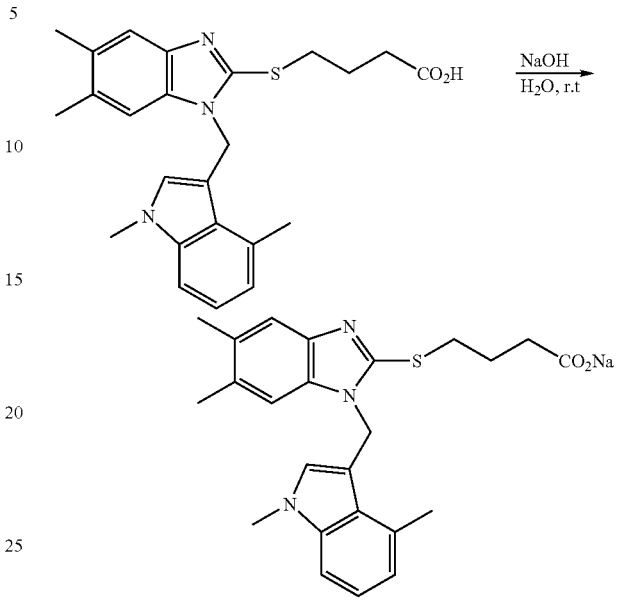

11.9 ml (1.19 mmol) of 0.1 M aqueous sodium hydroxide solution were added to 100 ml of an aqueous solution containing 503 mg (1.19 mmol) of the above compound no. 519 followed by stirring at room temperature. Subsequently, the reaction solution was freeze-dried to obtain 470 mg (1.05 mmol) of the sodium salt (yield: 89%).

$^1$H-NMR (400 MHz, DMSO-d6) (ppm): 7.37 (s, 1H), 7.19 (d, 1H, J=8.24 Hz), 7.09–7.01 (m, 2H), 6.80 (d, 1H, J=7.09 Hz), 6.32 (s, 1H), 5.66 (s, 2H), 3.59 (s, 3H), 3.26 (m, 2H), 2.66 (s, 3H), 2.27 (s, 3H), 2.21 (s, 3H), 1.95 (m, 2H), 1.81 (m, 2H)

Example 10

The compounds indicated below were synthesized using the respective corresponding substrates according to the same method as Example 9.

Sodium Salt of Compound No. 39

$^1$H-NMR (270 MHz, DMSO-d6) (ppm): 7.57 (d, 1H, J=Hz), 7.28 (d, 1H, J=7 Hz), 7.20 (d, 1H, J=8 Hz), 7.15–7.00 (m, 3H), 6.77 (d, 1H, J=7 Hz), 6.47 (s, 1H), 5.69 (s, 2H), 3.60 (s, 3H), 3.31 (t, 2H, J=7 Hz), 2.61 (s, 3H), 1.99 (t, 2H, J=7 Hz), 1.84 (p, 2H, J=7 Hz)

Sodium Salt of Compound No. 52

$^1$H-NMR (400 MHz, DMSO-d6) (ppm): 7.97 (d, 1H), 7.91 (d, 1H, J=6.76 Hz), 7.57 (d, 1H, J=7.75 Hz), 7.44–7.38 (m, 3H), 7.30 (s, 1H), 7.12 (m, 2H), 5.63 (s, 2H), 3.33 (m, 2H), 2.03 (m, 2H), 1.87 (m, 2H)

Sodium Salt of Compound No. 135

$^1$H-NMR (400 MHz, DMSO-d6) (ppm): 7.21–7.00 (m, 4H), 6.79 (d, 1H, J=7.29 Hz), 6.67 (dd, 1H, J=2.43, 8.91 Hz), 6.51 (s, 1H), 5.65 (s, 2H), 3.75 (s, 3H), 3.62 (s, 3H), 3.31 (m, 2H), 2.59 (s, 3H), 1.95 (m, 2H), 1.82 (m, 2H)

Sodium Salt of Compound No. 532

$^1$H-NMR (400 MHz, DMSO-d6) (ppm): 7.98 (d, 1H, J=7.42 Hz), 7.90 (d, 1H, J=6.43 Hz), 7.44–7.39 (m, 2H), 7.35 (s, 1H), 7.18 (m, 2H), 5.57 (s, 2H), 3.28 (m, 2H), 2.26 (s, 3H), 2.23 (s, 3H), 1.99 (m, 2H), 1.84 (m, 2H)

Example 10

Production of 4-(1-((4-methylbenzothiophene-3-yl]methyl)-5-methoxybenzimidazole-2-ylthio)butanoate ethyl ester and 4-(1-((4-methylbenzothiophene-3-yl)methyl)-6-methoxybenzimidazole-2-ylthio)butanoate ethyl ester

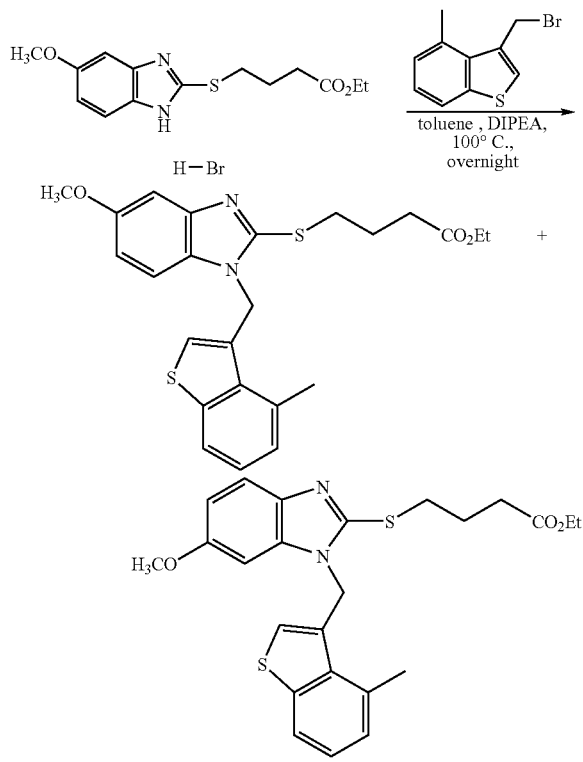

539 mg (1.44 mmol) of 4-(5-methoxybenzimidazole-2-ylthio)butanoate ethyl ester were suspended in 4 ml of toluene followed by the addition of 616 µl (3.60 mmol) of diisopropylethylamine and 384 mg (1.59 mmol) of 4-methyl-3-(bromomethyl)benzo[b]thiophene and heating at 100° C. After allowing to react overnight, saturated sodium bicarbonate solution was added followed by extraction with ethyl acetate. The organic phase was washed with water followed by drying with magnesium sulfate and concentrating the solvent under reduced pressure. The resulting residue was purified by silica gel column chromatography (hexane: ethyl acetate=4:1) to obtain 114 mg of 4-(1-((4-methylbenzothiophene-3-yl)methyl)-5-methoxybenzimidazole-2-ylthio)butanoate ethyl ester (yield: 17%) and 68 mg of 4-(1-((4-methylbenzothiophene-3-yl)methyl)-6-methoxybenzimidazole-2-ylthio)butanoate ethyl ester (yield: 10%).

4-(1-((4-methylbenzothiophene-3-yl)methyl)-5-methoxybenzimidazole-2-ylthio)butanoate ethyl ester $^1$H-NMR (270 MHz, CDCl$_3$) (ppm): 7.71 (d, 1H, J=7.56 Hz), 7.62 (d, 1H, J=8.64 Hz), 7.30–7.18 (m, 2H), 6.87 (dd, 1H, J=2.43, 8.64 Hz), 6.61 (d, 1H, J=2.43 Hz), 6.42 (s, 1H), 5.74 (s, 2H), 4.10 (q, 2H, J=7.29 Hz), 3.75 (s, 3H), 3.38 (t, 2H, J=7.29 Hz), 2.89 (s, 3H), 2.45 (t, 2H, J=7.29 Hz), 2.11 (m, 2H), 1.23 (t, 3H, J=7.29 Hz)

4-(1-((4-methylbenzothiophene-3-yl)methyl)-6-methoxybenzimidazole-2-ylthio)butanoate ethyl ester $^1$H-NMR (270 MHz, CDCl$_3$) (ppm): 7.70 (d, 1H, J=8.10 Hz), 7.29–7.17 (m, 3H), 7.02 (d, 1H, J=8.91 Hz), 6.80 (dd, 1H, J=2.43, 8.91 Hz), 6.40 (s, 1H), 5.74 (s, 2H), 4.11 (q, 2H, J=7.29 Hz), 3.87 (s, 3H), 3.42 (t, 2H, J=7.02 Hz), 2.88 (s, 3H), 2.46 (t, 2H, J=7.29 Hz), 2.10 (m, 2H), 1.23 (t, 3H, J=7.29 Hz)

Example 11

The following compounds were obtained according to the same method as Example 10.

4-(1-((5-methylbenzothiophene-3-yl)methyl)-5-methoxybenzimidazole-2-ylthio)butanoate ethyl ester (Yield: 24%)

$^1$H-NMR (270 MHz, CDCl$_3$) (ppm): 7.76 (d, 1H, J=8.10 Hz), 7.62 (s, 1H), 7.58 (d, 1H, J=8.64 Hz), 7.25 (1H), 6.84 (dd, 1H, J=2.43, 8.91 Hz), 6.81 (s, 1H), 6.65 (d, 1H, J=2.16 Hz), 5.47 (s, 2H), 4.11 (q, 2H, J=7.02 Hz), 3.74 (s, 3H), 3.39 (t, 2H, J=7.02 Hz), 2.51 (s, 3H), 2.47 (t, 2H, J=7.56 Hz), 2.11 (m, 2H), 1.24 (t, 3H, J=7.02 Hz)

4-(1-((5-methylbenzothiophene-3-yl)methyl)-6-methoxybenzimidazole-2-ylthio)butanoate ethyl ester (Yield: 18%)

$^1$H-NMR (270 MHz, CDCl$_3$) (ppm): 7.75 (d, 1H, J=8.10 Hz), 7.60 (s, 1H), 7.26–7.22 (m, 2H), 7.04 (d, 1H, J=8.91 Hz), 6.83 (s, 1H), 6.78 (dd, 1H, J=2.43, 8.91 Hz), 5.47 (s, 2H), 4.12 (q, 2H, J=7.02 Hz), 3.84 (s, 3H), 3.43 (t, 2H, J=7.29 Hz), 2.50 (s, 3H), 2.48 (t, 2H, J=7.29 Hz), 2.12 (m, 2H), 1.24 (t, 3H, J=7.02 Hz)

Example 12

Production of 4-(1-((4-methylbenzothiophene-3-yl)methyl)-5-methoxybenzimidazole-2-ylthio)butanoic acid (Compound No. 154)

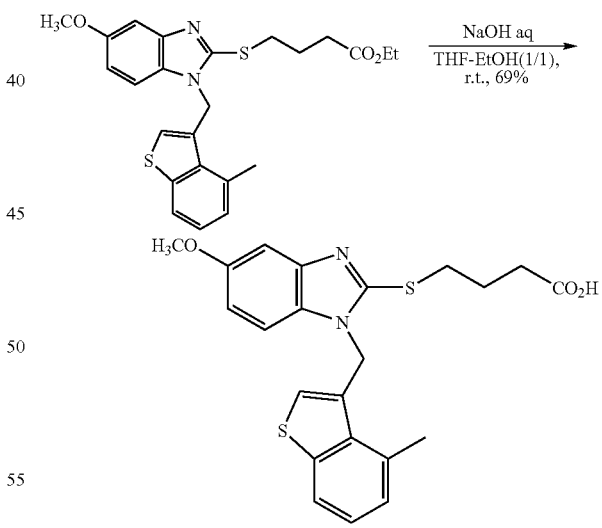

84.7 mg (0.186 mmol) of the 4-(1-((4-methylbenzothiophene-3-yl)methyl)-5-methoxybenzimidazole-2-ylthio)butanoate ethyl ester obtained in Example 10 were dissolved in a mixed solvent of 1 ml of THF and 1 ml of ethanol followed by the addition of 1 ml of 1 M aqueous sodium hydroxide solution and stirring for 1 hour at 40° C. Following completion of the reaction, 1.5 ml of 1 M hydrochloric acid were added followed by stirring for 30 minutes at room temperature. The resulting precipitate was filtered, washed with water, washed with ethanol and then dried to obtain 54.9 mg of the target compound (yield: 69%).

LC-MS:

Calculated value M=426.11, Measured value (M+H)$^+$ =427.2

$^1$H-NMR (270 MHz, DMSO-d6) (ppm): 7.80 (d, 1H, J=7.29 HZ), 7.60 (d, 1H, J=8.91 Hz), 7.31–7.20 (m, 3H), 6.95 (dd, 1H, J=2.16, 8.91 Hz), 6.53 (s, 1H), 5.94 (s, 2H), 3.73 (s, 3H), 3.37 (t, 2H, J=7.29 Hz), 2.86 (s, 3H), 2.34 (t, 2H, J=7.29 Hz), 1.90 (m, 2H)

Example 13

The following compounds were synthesized according to the same method as Example 12.

4-(1-((4-methylbenzothiophene-3-yl)methyl)-6-methoxy-benzimidazole-2-ylthio)butanoic acid (Compound No. 1114)

Yield: 60%

LC-MS:

Calculated value M=426.11, Measured value (M+H)$^+$ =427.2

$^1$H-NMR (270 MHz, DMSO-d6) (ppm): 7.78 (d, 1H, J=7.83 Hz), 7.52 (d, 1H, J=8.91 Hz), 7.34–7.17 (m, 3H), 6.77 (dd, 1H, J=2.34, 8.91 Hz), 6.37 (s, 1H), 5.83 (s, 2H), 3.78 (s, 3H), 3.32 (t, 2H, J=7.29 Hz), 2.82 (s, 3H), 2.34 (t, 2H, J=7.56 Hz), 1.93 (m, 2H)

In this case however, 1 M hydrochloric acid was added following completion of the reaction followed by extraction with chloroform and washing with water. Drying was then performed with magnesium sulfate followed by concentrating the solvent under reduced pressure and drying to obtain the target compound.

4-(1-((5-methylbenzothiophene-3-yl)methyl)-5-methoxy-benzimidazole-2-ylthio)butanoic acid (Compound No. 152)

Yield: 63%

LC-MS:

Calculated value M=426.11, Measured value (M+H)$^+$ =426.8

$^1$H-NMR (270 MHz, DMSO-d6) (ppm): 7.88 (d, 1H, J=8.64 Hz), 7.76 (s, 1H), 7.58 (d, 1H, J=8.64 Hz), 7.28–7.24 (m, 3H), 6.94 (dd, 1H, J=2.16, 8.64 Hz), 5.72 (s, 2H), 3.74 (s, 3H), 3.40 (t, 2H, J=7.29 Hz), 2.42 (s, 3H), 2.36 (t, 2H, J=7.29 Hz), 1.92 (m, 2H)

4-(1-((5-methylbenzothiophene-3-yl)methyl)-6-methoxy-benzimidazole-2-ylthio)butanoic acid (Compound No. 1112)

Yield: 79%

LC-MS:

Calculated value M=426.11, Measured value (M+H)$^+$ =427.0

$^1$H-NMR (270 MHz, DMSO-d6) (ppm): 7.87 (d, 1H, J=8.10 Hz), 7.71 (s, 1H), 7.47 (d, 1H, J=8.91 Hz), 7.24 (m, 2H), 7.17 (d, 1H, J=2.16 Hz), 6.84 (dd, 1), 5.64 (s, 2H), 3.77 (s, 3H), 3.38 (t, 2H, J=7.02 Hz), 2.41 (s, 3H), 2.37 (t, 2H, J=7.56 Hz), 1.95 (m, 2H)

Example 14

Production of HCl Salt of Compound No. 532

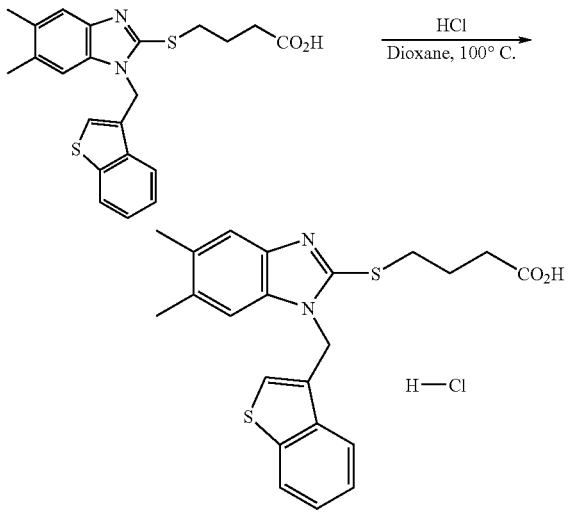

1.5 ml of 4 M hydrochloric acid/dioxane solution were added to 50 mg (0.122 mmol) of compound no. 532 followed by stirring at 100° C. Following completion of the reaction, the reaction solution was concentrated under reduced pressure to obtain 53 mg (1.05 mmol) of the target compound (yield: 97%).

$^1$H-NMR (270 MHz, DMSO-d6) (ppm): 8.00 (m, 1H), 7.89 (m, 1H), 7.52 (m, 2H), 7.45–7.42 (m, 2H), 7.32 (s, 1H), 5.78 (s, 2H), 3.48 (t, 2H, J=7.42 Hz), 2.37 (m, 2H), 2.34 (s, 3H), 2.30 (s, 3H), 1.92 (t, 2H, J=7.09 Hz)

Example 15

Production of HCl Salt of Compound No. 56

The target compound was obtained according to the same method as Example 14.

$^1$H-NMR (270 MHz, DMSO-d6) (ppm): 7.87 (d, 1H, J=8.08 Hz), 7.74 (s, 1H), 7.66 (d, 1H, J=6.76 Hz), 7.58 (d, 1H, J=8.74 Hz), 7.26 (m, 4H), 5.70 (s, 2H), 3.45 (t, 2H, J=7.26 Hz), 2.42 (s, 3H), 2.39 (t, 2H, J=7.26 Hz), 1.98 (m, 2H)

Example 16

Preparation of Recombinant Human Mast Cell Chymase

Recombinant human mast cell chymase was prepared in accordance with the report of Urata, et al. (Journal of Biological Chemistry, Vol. 266, p. 17173 (1991)). Namely, human mast cell chymase was purified by heparin sepharose (Pharmacia) from a culture supernatant of insect cells (Th5) infected with recombinant baculovirus containing cDNA coding for human mast cell chymase. Moreover, after activating in accordance with the report of Murakami, et al. (Journal of Biological Chemistry, Vol. 270, p. 2218 (1995)), the human mast cell chymase was purified with heparin sepharose to obtain active human mast cell chymase.

Example 17

Measurement of Inhibition of Enzyme Activity of Recombinant Human Mast Cell Chymase After adding 2 μl of DMSO solution containing a compound of the present invention to 50 μl of Buffer A (0.5–3.0 M NaCl, 50 mM Tris-HCl, pH 8.0) containing 1–5 ng of the active human mast cell chymase obtained in Example 16, 50 μl of Buffer A containing 0.5 mM succinyl-alanyl-histidyl-prolyl-phenylalanylparanitroanilide (Bacchem) as substrate were added and allowed to react for 5 minutes at room temperature. The changes over time in absorbance at 405 nm were measured to investigate inhibitory activity.

As a result, compound nos. 39, 56, 58, 59, 63, 148, 154, 519, 532, 534, 536, 538, 615, 1112 and 1114 were observed to demonstrate inhibitory activity of $IC_{50}=1$ nM to less than 10 nM, while compound nos. 34, 38, 41, 42, 52, 54, 135, 137, 152, 244, 340, 436, 514, 521 and 628 were observed to demonstrate inhibitory activity of $IC_{50}=10$ nM to 100 nM.

As has been shown above, the benzimidazole derivatives of the present invention exhibit potent chymase inhibitory activity. Thus, the benzimidazole derivatives of the present invention were clearly demonstrated to be human chymase activity inhibitors that can be applied clinically for use in the prevention and/or treatment of various diseases involving human chymase.

Example 18

Production of Tablets

Tablets were produced having the individual tablet composition shown below.

| | |
|---|---|
| Compound No. 39 | 50 mg |
| Lactose | 230 mg |
| Potato starch | 80 mg |
| Polyvinylpyrrolidone | 11 mg |
| Magnesium stearate | 5 mg |

The compound of the present invention (compound of the examples), lactose and potato starch were mixed followed by uniformly wetting with a 20% ethanol solution of polyvinylpyrrolidone, passing through a 20 mesh sieve, drying at 45° C. and again passing through a 15 mesh sieve. The granules obtained in this manner were then mixed with magnesium stearate and compressed into tablets.

Example 19

Measurement of Blood Concentration During Administration by Intragastric Forced Feeding to Rats The compounds indicated with the above compound nos. 39, 52 and 244 were administered by intragastric forced feeding to male SD rats while fasting at a dose of 30 mg/kg, after which blood samples were collected immediately after administration and at 30 minutes and 1, 2 and 4 hours after administration. Following collection of blood samples, where samples were immediately separated into serum components, the compound of the present invention was extracted by ordinary solid phase extraction methods, and the resulting samples were analyzed by HPLC using an ODS column (32% acetonitrile-water-0.05% TFA was used for the mobile phase for compound nos. 52 and 244, while 47% acetonitrile-water-10 mM ammonium acetate buffer (pH 4.0) was used for the mobile phase for compound no. 39) followed by measurement of the amount of the unchanged form. Those results are shown in the table below.

| Compound No. | After 30 min. (μg/ml) | After 4 hr. (μg/ml) |
|---|---|---|
| 52 | 60.5 | 12.7 |
| 244 | 16.5 | 8.9 |
| 39 | 16.1 | 6.3 |

On the basis of the above results, the compounds of the present invention were rapidly absorbed after administration, and blood concentrations of the unchanged form shown in the table were measured after 30 minutes. Moreover, although blood concentrations decreased gradually until 4 hours after administration, a considerable amount of the unchanged forms could still be confirmed even at 4 hours after administration. Thus, the compounds of the present invention were determined to be a group of compounds having superior pharmacokinetic properties. The pharmacokinetic properties of the group of compounds in which A is —$CH_2CH_2CH_2$— are particularly superior.

Example 20

In Vitro Metabolism Test Using Liver Microsomes (Ms) Measurement Method:

\* Reaction Solution Composition and Reaction Conditions

Composition and Procedure

| | Composition | Reagent name | Final conc. | Comments |
|---|---|---|---|---|
| Reconstruction system Composition | Buffer | Phosphate buffer (pH 7.4) | 0.1 M | Reaction solution volume: 0.5 mL |
| | Chelating agent | EDTA | 1.0 mM | |
| | NADPH generation system | Magnesium chloride | 3.0 mM | |
| | | G6P | 5.0 mM | |
| | | G6PDH | 1.0 IU | |
| | Enzyme | Liver microsomes | 1.0 mg/mL | |
| | Substrate | Substrate (evaluation compound) | 5.0 μM | |
| | Reaction initiator | NADPH | 1.0 mM | |
| Reaction conditions | | 37° C., incubation (water bath, shaking), reaction times: 0, 2, 5, 10 and 30 min. | | |
| Reaction terminator (extraction liquid) | | Acetonitrile | | Equal to 3 volumes of reaction solution |
| Deproteinization | | Sampling of supernatant after centrifuging for 10 min. at 3000 rpm, removal of solvent with evaporator | | |
| Redissolution liquid | | Redissolution with HPLC mobile phase used for analysis | | |
| Analysis | | Detection of peak of unchanged form by HPLC using UV detector | | |

\* MR Calculation Method

The metabolic rate was determined from the decrease in the amount of the unchanged form at each reaction time and the reaction time based on assigning a value of 100% to the amount of the unchanged form at the initial concentration (reaction time: 0 minutes), and the metabolic rate at the time the metabolic rate reached a maximum was evaluated as the MR value.

$M$=(substrate concentration at reaction time: 0 min.−substrate concentration after reaction)÷reaction time÷protein concentration (nmol/min./mg protein)

These methods were used to obtain the measurement results indicated below.

| Compound No. | MR | Percentage of substrate remaining after 30 min. (%) |
|---|---|---|
| 34 | 0.260 | 60.3 |
| 38 | 0.329 | 29.8 |
| 39 | 0 | 80.1 |
| 41 | 0.129 | 73.9 |
| 52 | 0.331 | 47.5 |
| 56 | 0.111 | 41.2 |
| 58 | 0.048 | 72.3 |
| 135 | 0.097 | 55.2 |
| 244 | 0.211 | 57.9 |
| 514 | 0.087 | 48.7 |
| 519 | 0.102 | 52.9 |
| 521 | 0.088 | 61.1 |
| 532 | 0.277 | 36.2 |
| 534 | 0.102 | 63.0 |
| 536 | 0.131 | 56.3 |
| 615 | 0.159 | 62.3 |

According to the above results, the compounds of the present invention are a group of metabolically stable compounds. The group of compounds in which A is —CH2CH2CH2— was determined to be a group of particularly metabolically stable compounds.

INDUSTRIAL APPLICABILITY

The benzimidazole derivatives of the present invention or their medically allowed salts exhibit potent human chymase inhibitory activity. Thus, said benzimidazole derivatives or their medically allowed salts can be used as preventive and/or therapeutic agents that can be applied clinically as human chymase inhibitors for inflammatory diseases, allergic diseases, respiratory diseases, cardiovascular diseases or bone and cartilage metabolic diseases.

The invention claimed is:

1. A benzimidazole compound or its medically acceptable salt represented by the following formula:

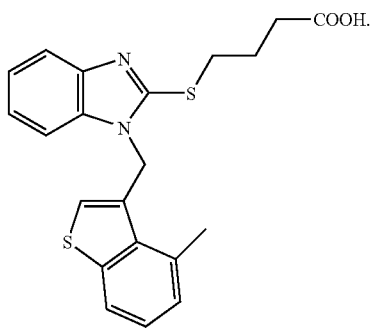

2. A benzimidazole compound or its medically acceptable salt represented by the following formula:

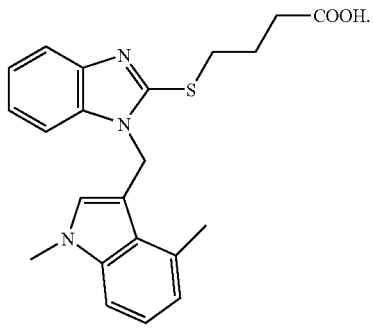

* * * * *